(12) United States Patent
Zhang et al.

(10) Patent No.: US 7,893,022 B2
(45) Date of Patent: *Feb. 22, 2011

(54) ANTI-ANGIOGENIC METHODS AND COMPOSITIONS

(75) Inventors: H. Steve Zhang, Richmond, CA (US); Philip D. Gregory, Orinda, CA (US); Edward J. Rebar, El Cerrito, CA (US)

(73) Assignee: Sangamo Biosciences, Inc., Richmond, CA (US)

( * ) Notice: Subject to any disclaimer, the term of this patent is extended or adjusted under 35 U.S.C. 154(b) by 123 days.

This patent is subject to a terminal disclaimer.

(21) Appl. No.: 11/981,386

(22) Filed: Oct. 31, 2007

(65) Prior Publication Data

US 2008/0118469 A1    May 22, 2008

Related U.S. Application Data

(62) Division of application No. 11/365,390, filed on Feb. 28, 2006, now Pat. No. 7,358,085.

(60) Provisional application No. 60/657,224, filed on Feb. 28, 2005, provisional application No. 60/677,584, filed on May 3, 2005, provisional application No. 60/715,326, filed on Sep. 8, 2005.

(51) Int. Cl.
*A61K 38/16* (2006.01)
*A61K 48/00* (2006.01)

(52) U.S. Cl. .......................... 514/2; 514/44 R
(58) Field of Classification Search .............. 514/2, 514/44 R
See application file for complete search history.

(56) References Cited

U.S. PATENT DOCUMENTS

| | | | |
|---|---|---|---|
| 4,186,183 A | 1/1980 | Steck et al. |
| 4,217,344 A | 8/1980 | Vanlerberghe et al. |
| 4,235,871 A | 11/1980 | Papahadjopoulos et al. |
| 4,261,975 A | 4/1981 | Fullerton et al. |
| 4,485,054 A | 11/1984 | Mezei et al. |
| 4,501,728 A | 2/1985 | Geho et al. |
| 4,603,044 A | 7/1986 | Geho et al. |
| 4,774,085 A | 9/1988 | Fidler |
| 4,797,368 A | 1/1989 | Carter et al. |
| 4,837,028 A | 6/1989 | Allen |
| 4,897,355 A | 1/1990 | Eppstein et al. |
| 4,946,787 A | 8/1990 | Eppstein et al. |
| 4,957,773 A | 9/1990 | Spencer et al. |
| 5,049,386 A | 9/1991 | Eppstein et al. |
| 5,173,414 A | 12/1992 | Lebkowski et al. |
| 5,176,996 A | 1/1993 | Hogan et al. |
| 5,210,015 A | 5/1993 | Gelfand et al. |
| 5,422,251 A | 6/1995 | Fresco |
| 5,538,848 A | 7/1996 | Livak et al. |
| 5,585,245 A | 12/1996 | Johnsson et al. |
| 5,607,918 A | 3/1997 | Eriksson et al. |
| 5,776,755 A | 7/1998 | Alitalo et al. |
| 5,789,538 A | 8/1998 | Rebar et al. |
| 5,840,686 A | 11/1998 | Chader et al. |
| 5,840,693 A | 11/1998 | Eriksson et al. |
| 5,863,736 A | 1/1999 | Haaland |
| 5,928,939 A | 7/1999 | Eriksson et al. |
| 5,932,540 A | 8/1999 | Hu et al. |
| 5,935,820 A | 8/1999 | Hu et al. |
| 5,994,300 A | 11/1999 | Bayne et al. |
| 6,007,988 A | 12/1999 | Choo et al. |
| 6,013,453 A | 1/2000 | Choo et al. |
| 6,040,157 A | 3/2000 | Hu et al. |
| 6,130,071 A | 10/2000 | Alitalo et al. |
| 6,140,081 A | 10/2000 | Barbas |
| 6,140,466 A | 10/2000 | Barbas et al. |
| 6,242,568 B1 | 6/2001 | Barbas et al. |
| 6,288,024 B1 | 9/2001 | Bouck et al. |
| 6,319,687 B1 | 11/2001 | Chader et al. |
| 6,391,850 B2 | 5/2002 | Bouck et al. |
| 6,410,248 B1 | 6/2002 | Greisman et al. |
| 6,451,763 B1 | 9/2002 | Tombran-Tink et al. |
| 6,453,242 B1 | 9/2002 | Eisenberg et al. |
| 6,479,626 B1 | 11/2002 | Kim et al. |
| 6,534,261 B1 | 3/2003 | Cox et al. |
| 6,573,092 B1 | 6/2003 | Kovesoli et al. |
| 6,607,882 B1 | 8/2003 | Cox et al. |
| 6,670,333 B2 | 12/2003 | Bouck et al. |
| 6,746,838 B1 | 6/2004 | Choo et al. |
| 6,785,613 B2 | 8/2004 | Eisenberg et al. |
| 6,790,941 B2 | 9/2004 | Barbas, III et al. |
| 6,794,136 B1 | 9/2004 | Eisenberg et al. |

(Continued)

FOREIGN PATENT DOCUMENTS

EP    0 476 983 B1    3/1992

(Continued)

OTHER PUBLICATIONS

Wang et al. (2004) IOVS, vol. 45 ( Suppl. 1 ), 1898-B709.*

(Continued)

*Primary Examiner*—Anne Marie S Wehbe
(74) *Attorney, Agent, or Firm*—Dahna S. Pasternak; Robins & Pasternak LLP

(57) ABSTRACT

Disclosed herein are methods and compositions for treatment of conditions requiring inhibition of angiogenesis. Such conditions include those characterized by neovascularization, such as retinopathies, macular degeneration and various malignancies.

17 Claims, 4 Drawing Sheets

U.S. PATENT DOCUMENTS

| | | |
|---|---|---|
| 6,797,691 B1 | 9/2004 | Bouck et al. |
| 6,824,978 B1 | 11/2004 | Cox, III et al. |
| 2002/0064802 A1 | 5/2002 | Raschke et al. |
| 2003/0119023 A1 | 6/2003 | Choo et al. |
| 2006/0182736 A1* | 8/2006 | Kim et al. ............... 424/94.65 |

FOREIGN PATENT DOCUMENTS

| | | |
|---|---|---|
| WO | WO 91/16024 A1 | 10/1991 |
| WO | WO 91/17424 A1 | 11/1991 |
| WO | WO 93/24641 A2 | 2/1993 |
| WO | WO 95/19431 A1 | 7/1995 |
| WO | WO 95/24473 A1 | 9/1995 |
| WO | WO 96/06166 A1 | 2/1996 |
| WO | WO 96/26736 A1 | 9/1996 |
| WO | WO 96/27007 A1 | 9/1996 |
| WO | WO 96/39515 A1 | 12/1996 |
| WO | WO 97/05250 A2 | 2/1997 |
| WO | WO 97/09427 A1 | 3/1997 |
| WO | WO 97/17442 A1 | 5/1997 |
| WO | WO 98/07832 A1 | 2/1998 |
| WO | WO 98/33917 A1 | 2/1998 |
| WO | WO 98/24811 A2 | 6/1998 |
| WO | WO 98/44350 A1 | 10/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 99/33485 A1 | 7/1999 |
| WO | WO 99/46364 A1 | 9/1999 |
| WO | WO 00/09148 A1 | 2/2000 |
| WO | WO 00/23464 A2 | 4/2000 |
| WO | WO 00/27878 A1 | 5/2000 |
| WO | WO 00/41566 A1 | 7/2000 |
| WO | WO 00/42219 A1 | 7/2000 |
| WO | WO 00/45835 A1 | 8/2000 |
| WO | WO 01/83732 A2 | 11/2001 |
| WO | WO 01/83793 A2 | 11/2001 |
| WO | WO 02/46412 A2 | 6/2002 |
| WO | WO 02/077227 A2 | 10/2002 |
| WO | WO 03/080648 A2 | 10/2003 |
| WO | WO 2004/108883 * | 12/2004 |
| WO | WO 2004/108883 A2 | 12/2004 |

OTHER PUBLICATIONS

Reich et al. (2003) Molecular Vision, vol. 9, 210-216.*
Mori et al. (2002) IOVS, vol. 43(6), 1994-2000.*
Tan et al. (2003) PNAS, vol. 100(21), 11997-12002.*
Greisman et al. (1997) Science, vol. 275, 657-661.*
Abe, et al., "Overexpression of Pigment Epithelium-Derived Factor Decreases Angiogenesis and Inhibits the Growth of Human Malignant Melanoma Cells In Vivo," *Am J Pathol* 164:1225-1232 (2004).
Ahmad, et al., "Antibody-Mediated Specific Binding and Cytotoxicity of Liposome-Entrapped Doxorubicin to Lung Cancer Cells In Vitro," *Cancer Res* 52(17):4817-4820 (1992).
Altschul, et al., "Basic Local Alignment Search Tool," *J. Mol. Biol.* 215:403-410 (1990).
Alvarez et al. "A Phase 1 Study of Recombinant Adenovirus Vector-Mediated Intraperitoneal Delivery of Herpes Simplex Virus Thymidine Kinase (HSV-TK) Gene and Intravenous Ganciclovir for Previously Treated Ovarian and Extraovarian Cancer Patients," *Hum. Gene Ther.* 8(5):597-613 (1997).
Beaucage et al., "Deoxynucleoside Phosphoramidites—A New Class of Key Intermediates for Deoxypolynucleotides," *Tetrahedron Letters* 22:1859-1862 (1981).
Behr et al., "Gene Transfer With Synthetic Cationic Amphiphiles: Prospects for Gene Therapy," *Bioconjug. Chem.* 5(5):382-389 (1994).
Berg and Shi, "The Galvanization of Biology: A Growing Appreciation for the Roles of Zinc," *Science* 271:1081-1085 (1996).

Bird et al., "Methylation-Induced Repression—Belts, Braces, and Chromatin," *Cell* 99(5):451-454 (1999).
Bitko & Barik, "Persistent Activation of Rela by Respiratory Syncytial Virus Involves Protein Kinase C, Underphosphorylated Ikappabbeta, and Sequestration of Protein Phosphatase 2A by the Viral Phosphoprotein," *J. Virol.* 72(7):5610-5618 (1998).
Blaese et al., "Vectors in Cancer Therapy: How Will They Deliver?" *Cancer Gene Therapy* 2:291-297 (1995).
Blaese et al., "T Lymphocyte-Directed Gene Therapy for ADA-SCID: Initial Trial Results After 4 Years," *Science* 270(5235):475-480 (1995).
Buchscachher et al., "Human Immunodeficiency Virus Vectors for Inducible Expression of Foreign Genes," *J Virol* 66(5):2731-2739 (1992).
Carbonetti et al., "Use of Purtussis Toxin Vaccine Molecule PT9K/129G to Deliver Peptide Epitopes for Simulation of a Cytotoxic T Lymphocyte Response," *Abstr. Annu. Meet. Am. Soc. Microbiol.* 95:295 (1995).
Chern et al., "The Regulator of MAT2 (ROM2) Protein Binds to Early Maturation Promoters and Represses PVALF-Activated Transcription," *Plant Cell* 8(2):305-321 (1996).
Cho et al., "Analysis of the C-Terminal Region of *Arabidopsis thaliana* Apetalai as a Transcription Activation Domain," *Plant Mol. Biol.* 40(3):419-429 (1999).
Choo et al., "Toward a Code for the Interactions of Zinc Fingers With DNA: Selection of Randomized Fingers Displayed on Phage," *PNAS* 91:11163-11167 (1994).
Choo et al., "Selection of DNA Binding Sites for Zinc Fingers Using Randomized DNAS Reveals Coded Interactions," *PNAS* 91:11168-11172 (1994).
Cirillo et al., "Binding of the Winged-Helix Transcription Factor HNF3 to a Linker Histone Site on the Nucleosome," *EMBO J.* 17:244-254 (1998).
Clarke-Curtiss & Curtiss, "Analysis of Recombinant Dna Using *Escherichia Coli* Minicells," *Methods in Enzymology* 101:347-362 (1983).
Colley, et al., "Conversion of a Golgi Apparatus Sialyltransferase to a Secretory Protein by Replacement of the NH2-Terminal Signal Anchor With a Signal Peptide," *J. Biol. Chem.* 264(30):17619-17622 (1989).
Collingwood, et al., "Nuclear Receptors: Coactivators, Corepressors and Chromatin Remodeling in the Control of Transcription," *J. Mol. Endocrinol.* 23(3):255-275 (1999).
Conn, et al., "Amino Acid and cDNA Sequences of a Vascular Endothelial Cell Mitogen That Is Homologous to Platelet-Derived Growth Factor," *PNAS USA* 87:2628-2632 (1990).
Cordingley, et al., "Steroid-Dependent Interaction of Transcription Factors With the Inducible Promoter of Mouse Mammary Tumor Virus In Vivo," *Cell* 48:261-270 (1987).
Crystal, "Transfer of Genes to Humans: Early Lessons and Obstacles to Success," *Science* 270(5235):404-410 (1995).
Damm, et al., "Protein Encoded by V-ERBA Functions as a Thyroid-Hormone Receptor Antagonist," *Nature* 339:593-597 (1989).
Dawson, et al., "Pigment Epithelium-Derived Factor: A Potent Inhibitor of Angiogenesis," *Science* 285:245-248 (1999).
Deamer & Bangham, "Large Volume Liposomes by an Ether Vaporization Method," Biochim. Biophys. Acta 443(3):629-634 (1976).
Derossi, et al., "The Third Helix of the Antennapedia Homeodomain Translocates Through Biological Membranes," *J. Biol. Chem.* 269(14):10444-10450 (1994).
Desjarlais, et al., "Length-Encoded Multiplex Binding Site Determination: Application to Zinc Finger Proteins," *PNAS* 91:11099-11103 (1994).
Desjarlais, et al., "Toward Rules Relating Zinc Finger Protein Sequences and DNA Binding Site Preferences," *PNAS* 89:7345-7349 (1992).
DesjarlaisM et al., "Use of a Zinc-Finger Consensus Sequences Framework and Specificity Rules to Design Specific DNA Binding, Proteins" *PNAS* 90:2256-2260 (1993).
Donelly, et al., "Targeted Delivery of Peptide Epitopes to Class I Major Histocompatibility Molecules by a Modified Pseudomonas Exotoxin," *PNAS* 90(8):3530-3534 (1993).

Doyle & Hunt, "Reduced Nuclear Factor Kappab (P65) Expression in Rat Primary Sensory Neurons After Peripheral Nerve Injury," *Neuroreport* 8(13):2937-2942 (1997).

Dranoff, et al., "A Phase I Study of Vaccination With Autologous, Irradiated Melanoma Cells Engineered to Secrete Human Granulocyte-Macrophage Colony Stimulating Factor," *Hum Gene Ther.* 8(1):111-112 (1997).

Dunbar, et al., "Retrovirally Marked CD34-Enriched Peripheral Blood and Bone Marrow Cells Contribute to Long-Term Engraftment After Autologous Transplantation," *Blood* 85(11):3048-3057 (1995).

Eisenberg, et al., "Promoter Domains Required for Expression of Plasmid-Borne Copies of the Herpes Simplex Virus Thymidine Kinase Gene in Virus-Infected Mouse Fibroblasts and Microinjected Frog Oocytes," *Mol. Cell. Biol.* 5:1940-1947 (1985).

Ellem, et al., "A Case Report: Immune Responses and Clinical Course of the First Human Use of Granulocyte/Macrophage-Colony-Stimulating-Factor-Transduced Autologous Melanoma Cells for Immunotherapy," *Cancer. Immunol Immunother.* 44(1):10-20 (1997).

Elliott & O'Hare, "Intercellular Trafficking and Protein Delivery by a Herpesvirus Structural Protein," *Cell* 88(3):223-233 (1997).

Evans, "The V-ERBA Oncogene is a Thyroid Hormone Receptor Antagonist," *Int. J. Cancer Suppl.* 4:26-28 (1989).

Fahraeus, et al., "Inhibition of PRB Phosphorylation and Cell-Cycle Progression by a 20-Residue Peptide Derived From P16CDKN2/INK4A," *Current Biology* 6:84 (1996).

Fields, et al., "A Novel Genetic System to Detect Protein-Protein Interactions," *Nature* 340:245-246 (1989).

Fink, et al., "Identification of a Tightly Regulated Hypdxia-Response Element in the Promoter of Human Plasminogen Activator Inhibitor-1," *Blood* 99:2077-2083 (2002).

Fraley, et al., "Entrapment of a Bacterial Plasmid in Phospholipid Vesicles: Potential for Gene Transfer," *PNAS* 76:3348-3352 (1979).

Gao, et al., "Cationic Liposome-Mediated Gene Transfer," *Gene Therapy* 2:710-722 (1995).

Garcia, et al., "Inhibition of Xenografted Human Melanoma Growth and Prevention If Metastasis Development by Dual Antiangiogenic/Antitumor Activities of Pigment Epithelium-Derived Factor," *Cancer Res* 64:5632-5642 (2004).

Gibson, et al., "A Novel Method for Real Time Quantitative RT-PCR," *Genome Research* 6:995-1001 (1996).

Goff, et al., "Identification of Functional Domains in the Maize Transcriptional Activator C1: Comparison of Wild-Type and Dominant Inhibitor Proteins," *Genes Dev.* 5(2):298-309 (1991).

Gong, et al., "A Constitutively Expressed MYC-Like Gene Involved in Anthocyanin Biosynthesis From *Perilla frutescens*: Molecular Characterization, Heterologous Expression in Transgenic Plants and Transactivation in Yeast Cells," *Plant Mol. Biol.* 41(1):33-44 (1999).

Gossen & Bujard, "Tight Control of Gene Expression in Mammalian Cells by Tetracycline-Responsive Promoters," *PNAS USA* 89:5547 (1992).

Greisman, et al., "A General Strategy for Selecting High-Affinity Zinc Finger Proteins for Diverse DNA Target Sites," *Science* 275:657-661 (1997).

Hagmann, et al., "The VP16 Paradox: Herpes Simplex Virus VP16 Contains a Long-Range Activation Domain But Within the Natural Multiprotein Complex Activates Only From Promoter-Proximal Positions," *J. Virol.* 71:5952-5962 (1997).

Halin, et al., "Decreased Pigment Epithelium-Derived Factor Is Associated With Metastic Phenotype in Human and Rat Prostate Tumors," *Cancer Res* 64:5664-5671 (2004).

Han, et al., "Ligand-Directed Retroviral Targeting of Human Breast Cancer Cells," *PNAS USA* 92:9747-9751 (1995).

Hanahan, et al., "Fourteenth Annual Pezcoller Symposium : The Novel Dichotomy of Immune Interactions With Tumors," *Cancer Res* 63:3005-3008 (2003).

Hansen, et al., "Adeno-Associated Virus Encoding Green Flourescent Protein as a Label for Retinal Pigment Epithelium," *Invest Opthalmol Vis Sci* 44:772-780 (2003).

Heid, et al., "Real Time Quantitative PCR," *Genome Research* 6:986-994 (1996).

Hendrich. et al., "Genomic Structure and Chromosomal Mapping of the Murine and Human MBD1, MBD2, MBD3, and MBD4 Genes," *Mamm Genome* 10:906-912 (1999).

Henikoff, et al., "Amino Acid Substitution Matrices From Protein Blocks," *PNAS USA* 89:10915 (1989).

Hermonat, et al., "Use of Adeno-Associated Virus as a Mammalian DNA Cloning Vector: Transduction of Neomycin Resistance Into Mammalian Tissue Culture Cells," *PNAS* 81:6466-6470 (1984).

Hobo, et al., "A BZIP Factor, TRAB1, Interacts With VPI and Mediates Abscisic Acid-Induced Transcription," *PNAS USA* 96:15,348-15,353 (1999).

Holland, et al., "Detection of Specific Polymerase Chain Reaction Product by Utilizing the 5'→3' Exonuclease Activity of Thermus Aquaticus DNA Polymerase," *PNAS USA* 88:7276-7280 (1991).

Hope, et al., "Production of Large Unilamellar Vesicles by a Rapid Extrusion Procedure. Characterization of Size Distribution, Trapped Volume and Ability to Maintain a Memgrane Potential," *Biochim. Biophys. Acta* 812:55-65 (1985).

Hope, et al., "Generation of Multilamellar and Unilamellar Phospholipid Vesicles," *Chem. Phys. Lip.* 40:89-107 (1986).

Inaba, et al., "Generation of Large Numbers of Dendritic Cells From Mouse Bone Marrow Cultures Supplemented With Granulocyte/Macrophage Colony-Stimulating Factor," *J Exp Med* 176:1693-1702 (1992).

Jamieson, et al., "In Vitro Selection of Zinc Fingers With Altered DNA-Binding Specificity," *Biochemistry* 33:5689-5695 (1994).

Jamieson, et al., "A Zinc Finger Directory for High-Affinity DNA Recognition," *PNAS USA* 93:12834-12839 (1996).

Johann, et al., "GLVRI, A Receptor for Gibbon Ape Leukemia Virus, Is Homologous to a Phosphate Permease of Neurospora Crassa and Is Expressed At High Levels in the Brain and Thymus," *J Virol* 66:1635-1640 (1992).

Joukov, et al., "A Novel Vascular Endothelial Growth Factor, VEGF-C, Is a Ligand for the Flt4 (VEGFR-3) and KDR (VEGFR-2) Receptor Tyrosine Kinases," *EMBO J.* 15:290-298 (1996).

Karlin, et al., "Applications and Statistics for Multiple High-Scoring Segments in Modular Sequences," *PNAS* 90:5873-5887 (1993).

Kearns, et al., "Recombinant Adeno-Associated Virus (AAV-CFTR) Vectors Do Not Integrate in a Site-Specific Fashion in an Immortalized Epithelial Cell Line," *Gene Ther.* 9:748-755 (1996).

Keck, et al., "Vascular Permeability Factor, An Endothelial Cell Mitogen Related to PDGF," *Science* 246:1309-1312 (1989).

Kim, et al., "Hybrid Restriction Enzymes: Zinc Finger Fusions FOK 1 Cleavage Domain," *PNAS* 93:1156-1160(1996).

Kim, et al., "Getting a Handhold on DNA: Design of Poly-Zinc Finger Proteins With Femtomolar Dissociation Constants," *PNAS USA* 95:2812-2817 (1998).

Klimpel, et al., "Anthrax Toxin Protective Antigen Is Activated by a Cell Surface Protease With the Sequence Specificity and Catalytic Properties of Furin," *PNAS USA* 89:10277-10281 (1992).

Knoepfler, et al., "Sin Meets Nurd and Other Tails of Repression," *Cell* 99:447-450 (1999).

Kohn, et al., "Engraftment of Gene-Modified Umbilical Cord Blood Cells in Neonates With Adenosine Deaminase Deficiency," *Nat Med* 1:1017-1102 (1995).

Kotin, "Prospects for the Use of Adeno-Associated Virus as a Vector for Human Gene Therapy," *Hum. Gene Ther.* 5:793-801 (1994).

Lee, et al., "Vascular Endothelial Growth Factor-Related Protein: A Ligand and Specific Activator of the Tyrosine Kinase Receptor Flt4," *PNAS USA* 93:1988-1992 (1996).

Lemon, et al., "Nuclear Receptor Cofactors as Chromatin Remodelers," *Curr. Opin. Genet. Dev.* 9:499-504 (1999).

Leo, et al., "The SRC Family of Nuclear Receptor Coactivators," *Gene* 245:1-11 (2000).

Leonnetti, et al., "Antibody-Targeted Liposomes Containing Oligodeoxyribonucleotides Complementary to Viral RNA Selectively Inhibit Viral Replication," *PNAS* 87:2448-2451 (1990).

Leung, et al., "Vascular Endothelial Growth Factor is a Secreted Angiogenic Mitogen," *Science* 246:1306-1309 (1989).

Lin, et al., "Inhibition of Nuclear Translocation of Transcription Factor NF-Kappa B by a Synthetic Peptide Containing a Cell Membrane-Permeable Motif and Nuclear Localization Sequence," *J. Biol. Chem.* 270:14255-14258 (1995).

Liu, et al., "Suppression of Growth and Transformation and Induction of Apoptosis by EGR-1," *Cancer Gene Ther.* 5:3-28 (1998).

Liu et al., "Design of Polydactyl Zinc-Finger Proteins for Unique Addressing Within Complex Genomes," *PNAS* 94: 5525-5530 (1997).

Lu et al., "Evaluation of Tumor-Specific Promoter Activities in Melanoma," *Gene Therapy* 12:330-338 (2005).

Malech, et al., "Prolonged Production of Nadph Oxidase-Corrected Granulocytes After Gene Therapy of Chronic Granulomatous Disease," *PNAS* 94(22):12133-12138 (1997).

Malik, et al., "Transcriptional Regulation Through Mediator-Like Coactivators in Yeast and Metazoan Cells," *Trends Biochem. Sci.* 25:277-283 (2000).

Manteuffel-Cymborowska, "Nuclear Receptors, Their Coactivators and Modulation of Transcription," *Acta Biochim. Pol.* 46:77-89 (1999).

Mapp, et al., "Activation of Gene Expression by Small Molecule Transcriptopn Factors," *PNAS USA* 97:3930-3935 (2000).

Margolin, et al., "Kruppel-Associated Boxes Are Potent Transcriptional Repression Domains," *PNAS USA* 91:4509-4513 (1994).

Martin, et al., "Gene Delivery to the Eye Using Adeno-Associated Viral Vectors," *Methods* 28:267-275 (2002).

Matsumoto, et al., "Antiangiogenic Property of Pigment Epithelium-Derived Factor in Hepatocellular Carcinoma," *Hepatology* 40:252-259 (2004).

Mayer, et al., "Vesicles of Variable Sizes Produced by a Rapid Extrusion Procedure," *Biochim. Biophys. Acta* 858:161-168 (1986).

McKenna, et al., "Nuclear Receptor Coactivators: Multiple Enzymes, Multiple Complexes, Multiple Functions," *J. Steroid Biochem. Mol. Biol.* 69:3-12 (1999).

Miller, et al., "Construction and Properties of Retrovirus Packaging Cells Based on Gibbon Ape Leukemia Virus," *J. Virol.* 65:2220-2224 (1991).

Mistili & Spector, "Applications of the Green Flourescent Protein in Cell Biology and Biotechnology," *Nature Biotechnology* 15:961-964 (1997).

Mori, et al., "AAV-Mediated Gene Transfer of Pigment Epithelium-Derived Factor Inhibits Choroidal Neovascularization," *Invest Opthalmol Vis Sci* 43:1994-2000 (2002).

Morrison, "Transformation in *Escherichia coli*: Cryogenic Preservation of Competent Cells," *J. Bact.* 132:349-351 (1977).

Muzyczka, "Adeno-Associated Virus (AAV) Vectors: Will They Work?," *J Clin Invest* 94:1351 (1994).

Needham-Van Devanter, et al., "Characterization of an Adduct Between CC-1065 and a Defined Oligonucleotide Duplex," *Nucleic Acids Research* 12:6159-6168 (1984).

Needleman, et al., "A General Method Applicable to the Search for Similarities in the Amino Acid Sequence of Two Proteins," *J. Mol. Biol.* 48:443-453 (1970).

Neering, et al., "Transduction of Primitive Human Hematopoietic Cells With Recombinant Adenovirus Vectors," *Blood* 88:1147-1155 (1996).

Novak, et al., "Functional Characterization of Protease-Treated *Bacillus anthracis* Protective Antigen," *J. Biol. Chem.* 267:17186-17193 (1992).

Ogawa, et al., "Rice Gibberellin-Insensitive Gene Homolog, Osgai, Encodes a Nuclear-Localized Protein Capable of Gene Activation At Transcriptional Level," *Gene* 245:21-29 (2000).

Ohno-Matsui et al., "Vascular Endothelial Growth Factor Upregulates Pigment Epithelium-Derived Factor Expression Via VEGFR-1 in Human Retinal Pigment Epithelial Cells," *Biochemical and Biophysical Res Comm* 303:962-967 (2003).

Okanami, et al., "Half-1, a Bzip-Type Protein, Interacting With the Wheat Transcription Factor HBP-1A Contains a Novel Transcriptional Activation Domain," *Genes Cells* 1:87-99 (1996).

Oligino, et al., "Drug Inducible Transgene Expression in Brain Using a Herpes Simplex Virus Vector," *Gene Ther.* 5:491-496 (1998).

Pain, et al., "The Carbonic Anhydrase II Gene, a Gene Regulated by Thyroid Hormone and Erythropoietin, is Repressed by the V-ERBA Oncogene in Erythrocytic Cells," *New Biol.* 2:284-294 (1990).

Palva, et al., "Secretion of Interferon by *Bacillus subtilis*," *Gene* 22:229-235 (1983).

Passoth, et al., "Analysis of the Hypoxia-Induced ADH2 Promoter of the Respiratory Yeast *Pichia stipitis* Reveals a New Mechanism for Sensing of Oxygen Limitation in Yeast," *Yeast* 20:39-51 (2003).

Pearson, et al., "Improved Tools for Biological Sequence Comparison," *PNAS USA* 85:2444-2448 (1988).

Pengue, et al., "Repression of Transcriptional Activity at a Distance by the Evolutionarily Conserved Krab Domain Present in a Subfamily of Zinc Finger Proteins," *Nucl. Acids Res.* 22:2908-2914 (1994).

Perelle, et al., "Characterization of *Clostridium perfringens* Iota-Toxin Genes and Expression in *Escherichia coli*," *Infect. Immun.* 61:5147-5156 (1993).

Pina, et al., "Nucleosome Positioning Modulates Accessibility of Regulatory Proteins to the Mouse Mammary Tumor Virus Promoter," *Cell* 60:719-731 (1990).

Pomerantz, et al., "Analysis of Homeodomain Function by Structure-Based Design of a Transcription Factor," *PNAS* 92: 9752-9756 (1995).

Pomerantz, et al., "Structure-Based Design of Transcription Factors," *Science* 267:93-96 (1995).

Prochiantz, "Getting Hydrophilic Compounds Into Cells: Lessons From Homeopeptides," *Current Opinion in Neurobiology* 6:629-634 (1996).

Rebar, et al, "Zinc Finger Phage: Affinity Selection of Fingers With New DNA-Binding Specifities," *Science* 263:671-673 (1994).

Remy, et al., "Gene Transfer With a Series of Lipophilic DNA-Binding Molecules," *Bioconjugate Chem* 5:647-654 (1994).

Rendahl, et al., "Regulation of Gene Expression In Vivo Following Transduction by Two Separate RAAV Vectors," *Nat. Biotechnol* 16:757-761 (1998).

Renneisen, et al., "Inhibition of Expression of Human Immunodeficiency Virus-1 In Vitro by Antibody-Targeted Liposomes Containing Antisense RNA to the ENV Region," *J. Biol. Chem.* 265:16337-16342 (1990).

Rhodes, et al., "Zinc Fingers: They Play a Key Part in Regulating the Activity of Genes in Many Species, From Yeast to Humans, Fewer Than 10 Years Ago No One Knew They Existed," *Scientific American* 268:56-65 (1993).

Robertson, et al., "DNMT1 Forms a Complex With RB, E2F1 and HDAC1 and Represses Transcription From E2F-Responsive Promoters," *Nature Genet.* 25:338-342 (2000).

Robyr, et al., "Nuclear Hormone Receptor Coregulators in Action: Diversity for Shared Tasks," *Mol. Endocrinol* 14:329-347 (2000).

Rosenecker, et al., "Adenovirus Infection in Cystic Fibrosis Patients: Implications for the Use of Adenoviral Vectors for Gene Transfer," *Infection* 24:5-8 (1996).

Samulski, et al., "Helper-Free Stocks of Recombinant Adeno-Associated Viruses: Normal Integration Does Not Require Viral Gene Expression," *J. Virol.* 63:3822-3828 (1989).

Sap, et al., "Repression of Transcription Mediated at a Thyroid Hormone Response Element by the V-ERB-A Oncogene Product," *Nature* 340:242-244 (1989).

Sebo, et al., "Cell-Invasive Activity of Epitope-Tagged Adenylate Cyclase of *Bordetella pertussis* Allows In Vitro Presentation of a Foreign Epitope to CD8+ Cytotoxic T Cells," *Infect Immun* 63:3851-3857 (1995).

Seipel, et al., "Different Activation Domains Simulate Transcription From Remote ('Enhancer') and Proximal ('Promoter') Positions," *EMBO J.* 11:4961-4968 (1996).

Smith and Waterman, "Comparison of Biosequences," *Advances in Applied Mathematics* 2:482-489 (1981).

Sommerfelt, et al., "Receptor Interference Groups of 20 Retroviruses Plating on Human Cells," *Virol.* 176:58-59 (1990).

Sprenger-Haussels, et al., "Transactivation Properties of Parsley Proline-Rich BZIP Transcription Factors," *Plant J.* 22:1-8 (2000).

Steele, et al., "Pigment Epithelium-Derived Factor: Neurotrophic Activity and Identification as a Member of the Serine Protease Inhibitor Gene Family," *PNAS USA* 90:1526-1530 (1992).

Stellmach, et al., "Prevention of Ischemia-Induced Retinopathy by the Natural Ocular Antiangiogenic Agent Pigment Epithelium-Derived Factor," *PNAS USA* 98:2593-2597 (2001).

Stenmark, et al., "Peptides Fused to the Amino-Terminal End of Diphtheria Toxin are Translocated to the Cytosol," . *Cell. Biol.* 113:1025-1032 (1991).

Sterman, et al., "Adenovirus-Mediated Herpes Simplex Virus Thymidine Kinase/Ganciclovir Gene Therapy in Patients With Localized Malignancy: Results of a Phase I Clinical Trial in Malignant Mesothelioma," *Hum. Gene Ther.* 7:1083-1089 (1998).

Studeny, et al., "Mesenchymal Stem Cells: Potential Precursors for Tumor Stroma and Targeted-Delivery Vehicles for Anticancer Agents," *J. Natl Cancer Inst* 96:1593-1603 (2004).

Szoka, et al., "Comparative Properties and Methods of Preparation of Lipid Vesicles (Liposomes)," *Ann Rev. Biophys. Bioeng.* 9:467-508 (1980).

Tai, et el., "Concurrent Delivery of GM-CSF and Endostatin Genes by a Single Adenoviral Vector Provides a Synergistic Effect on the Treatment of Orthotopic Liver Tumors," *J. Gene Medicine* 5:386-398 (2003).

Thiesen, "Multiple Genes Encoding Zinc Finger Domains are Expressed in Human T Cells," *New Biologist* 2:363-374 (1990).

Tombran-Tink, et al., "Therapeutic Prospects for PEDF: More Than a Promising Angiogenesis Inhibitor," *Trends Mol Med* 9:224-250 (2003).

Topf, et al., "Regional 'Pro-Drug' Gene Therapy: Intravenous Administration of an Adenoviral Vector Expressing the *E. coli* Cytosine Deaminase Gene and Systemic Administration of 5-Fluorocytosine Suppresses Growth of Hepatic Metastasis of Colon Carcinoma," *Gene Ther* 5:507-513 (1998).

Torchia, et al., "Co-Activators and Co-Repressors in the Integration of Transcriptional Responses," *Curr. Opin. Cell. Biol.* 10:373-383 (1998).

Tratschin, et al., "Adeno-Associated Virus Vector for High-Frequency Integration, Expression, and Rescue of Genes in Mammalian Cells," *Mol. Cell. Biol.* 5:3251-3260 (1985).

Tratschin, et al., "A Human Parvovirus, Adeno-Associated Virus, as a Eucaryotic Vector: Transient Expression and Encapsidation of the Procaryotic Gene for Chloramphenicol Acetyltransferase," *Mol. Cell Biol.* 4:2072-2081 (1984).

Tyler, et al., "The "Dark Side" of Chromatin Remodeling: Repressive Effects on Transcription," *Cell* 99:443-446 (1999).

Ulmasov, et al., "Activation and Repression of Transcription by Auxin-Response Factors" *PNAS USA* 96:5844-5849 (1999).

Utley, et al., "Transcriptional Activators Direct Histone Acetyltransferase Complexes to Nucleosomes," *Nature* 394:498-502 (1998).

Wagner, et al., "Efficient and Persistent Gene Transfer of AAV-CFTR in Maxillary Sinus," *Lancet* 351:1702-1703 (1998).

Wallace, et al., "A Set of Synthetic Oligodeoxyribonucleotide Primers for DNA Sequencing in the Plasmid Vector pBR322," *Gene* 16:21-26 (1981).

Wang, et al., "Positive and Negative Regulation of Gene Expression in Eukaryotic Cells With an Inducible Transcriptional Regulator," *Gene Ther.* 4:432-441 (1997).

Wang, et al., "PH-Sensitive Immunoliposomes Mediate Target-Cell-Specific Delivery and Controlled Expression of a Foreign Gene in Mouse," *PNAS USA* 84:7851-7855 (1987).

Wang, et al., "Supression of Angiogenesis and Tumor Growth by Adenoviral-Mediated Gene Transfer of Pigment Epithelium-Derived Factor," *Molecular Therapy* 8:72-79 (2003).

Welsh, et al., "Adenovirus-Mediated Gene Transfer for Cystic Fibrosis: Part A. Safety of Dose and Repeat Administration in the Nasal Epithelium. Part B. Clinical Efficacy in the Maxillary Sinus," *Hum. Gene Ther.* 2:205-218 (1995).

West, et al., "Gene Expression in Adeno-Associated Virus Vectors: The Effects of Chimeric MBNA Structure, Helper Virus, and Adenovirus VA1 RNA," *Virology* 160:38-47 (1987).

Williams, et al., "Low Density Lipoprotein Receptor-Independent Hepatic Uptake of a Synthetic, Cholesterol-Scavenging Lipoprotein: Implications for the Treatment of Receptor-Deficient Atherosclerosis," *PNAS* 85:242-246 (1988).

Wilson, et al., "Formation of Infectious Hybrid Virions With Gibbon Ape Leukemia Virus and Human T-Cell Leukemia Virus Retroviral Envelope Glycoproteins and the GAG and POL Proteins of Moloney Murine Leukemia Virus," *J Virol* 63:2374-2378 (1989).

Witzgall, et al., "The Kruppel-Associated Box-A (KRAB-A) Domain of Zinc Finger Proteins Mediates Transcriptional Repression," *PNAS USA* 91:4514-4518 (1994).

Wu, et at, "Building Zinc Fingers by Selection: Toward a Therapeutic Application," *PNAS* 92:344-348 (1995).

Wu, et al., "Functional Analysis of HD2 Histone Deacetylase Homologues in *Arabidopsis thaliana,*" *Plant J.* 22:19-27 (2000).

Zenke, et al., "V-ERBA Specifically Suppresses Transcription of the Avian Erythrocyte Anion Transporter (Band 3) Gene," *Cell* 52:107-119 (1988).

Zenke, et al., "V-ERBA Oncogene Activation Entails the Loss of Hormone-Dependent Regulator Activity of C-ERBA," *Cell* 61:1035-1049 (1990).

Zhang, et al., "Synthetic Zinc Finger Transcription Factor Action at an Endogenous Chromosomal Site. Activation of the Human Erythropoietin Gene," *Journal of Biological Chemistry* 275(43): 33850-33860 (2000).

\* cited by examiner

FIGURE 3
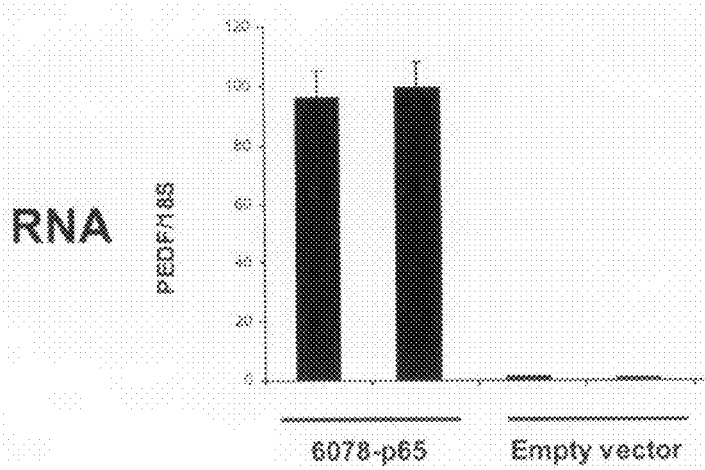
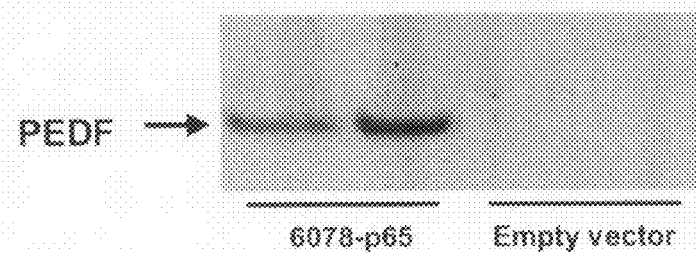
FIGURE 4

ANTI-ANGIOGENIC METHODS AND COMPOSITIONS

CROSS-REFERENCE TO RELATED APPLICATIONS AND INCORPORATION BY REFERENCE

The present application is a divisional application of U.S. patent application Ser. No. 11/365,390, filed Feb. 28, 2006 now U.S. Pat. No. 7,358,085, which claims the benefit, under 35 U.S.C. §119(e), of the following U.S. provisional patent applications: 60/657,224 (filed Feb. 28, 2005), 60/677,584 (filed May 3, 2005) and 60/715,326 (filed Sep. 8, 2005). The disclosures of all of the aforementioned applications are incorporated by reference in their entireties for all purposes.

STATEMENT OF RIGHTS TO INVENTIONS MADE UNDER FEDERALLY SPONSORED RESEARCH

Not applicable.

TECHNICAL FIELD

The present disclosure is in the field of anti-angiogenic treatments.

BACKGROUND

Abnormal or excessive angiogenesis is responsible for or associated with a wide range of diseases, including cancer (particularly solid tumors), blindness, arthritis and many others; therefore it is thought that anti-angiogenesis therapies are potentially effective for treating such diseases. Current anti-angiogenic therapies focus mainly on antagonizing the activity of angiogenic factors, such as vascular endothelial growth factor (VEGF). While such therapeutic agents (e.g. anti-VEGF antibodies) have been shown to be effective in certain situations, repeated administration is required to maintain the inhibition of angiogenesis. Moreover, because angiogenesis is a complex process regulated by a large number of pro-angiogenic and anti-angiogenic factors, agents that target only the activity of a single angiogenic factor may not be sufficient to prevent angiogenesis in many situations. Thus, because current approaches in which activity of a single angiogenic factor is inhibited are often ineffective, there is a need for more effective anti-angiogenic therapies. Therapies that are able to inhibit angiogenesis by modulating the activities of multiple angiogenic factors, and those able to confer long-term effect without repeated treatment, are more desirable.

Pigment epithelium derived factor (PEDF) is a 50 kDa (403 amino acid) glycoprotein. It was initially found to be secreted by retinal pigment epithelial (RPE) cells and is a potent natural anti-angiogenic factor of the eye. Reduced levels of PEDF have been reported in cases of age-related macular degeneration (AMD), and overexpression of PEDF cDNA inhibited neovascularization in a mouse model of AMD. See, for example, Dawson, D. W. et al. (1999) Pigment epithelium-derived factor: a potent inhibitor of angiogenesis. *Science* 285(5425):245-248; Stellmach, V. et al. (2001) Prevention of ischemia-induced retinopathy by the natural ocular antiangiogenic agent pigment epithelium-derived factor. *Proc. Natl. Acad. Sci. USA* 98(5):2593-2597 and Mori, K. et al. (2002) AAV-mediated gene transfer of pigment epithelium-derived factor inhibits choroidal neovascularization. *Invest. Opthalmol. Vis. Sci.* 43(6):1994-2000.

The anti-angiogenic function of PEDF has also been implicated in various cancers. Reduced PEDF level has been found to correlate with the metastatic phenotype of certain cancers, such as prostate cancer; and overexpression of PEDF inhibited tumor growth in xenograft models. See, for example, Halin S. et al. (2004) Decreased pigment epithelium-derived factor is associated with metastatic phenotype in human and rat prostate tumors. *Cancer Res.* 64(16):5664-71 and Abe R et al. (2004) Overexpression of pigment epithelium-derived factor decreases angiogenesis and inhibits the growth of human malignant melanoma cells in vivo. *Am. J. Pathol.* 164(4):1225-1232.

Because PEDF functions by inducing apoptosis of replicating endothelial cells, it is able to antagonize the activities of a number of different angiogenic factors that promote the proliferation of vascular endothelial cells, such as vascular endothelial growth factors (VEGFs), fibroblast growth factors (FGFs), and insulin-like growth factors (IGFs). Tombran-Tink, J. et al. (2003) Therapeutic prospects for PEDF: more than a promising angiogenesis inhibitor. *Trends Mol. Med.* 9(6):244-250. PEDF-based anti-angiogenesis therapy (i.e. activation of PEDF expression) is therefore likely to be more widely applicable, and more effective, than therapies in which expression of a single pro-angiogenic factor is inhibited (such as, e.g. VEGF antibody therapy).

SUMMARY

The disclosure relates, in part, to compositions, particularly engineered zinc finger proteins, that modulate expression of a PEDF gene. These compositions are useful in treating a wide variety of conditions, including conditions characterized by neovascularization and/or excessive angiogenesis. Also provided are methods for modulating vascularization, and treating neovascularization, by regulating the expression of, inter alia, a PEDF gene.

In one aspect, provided herein is an engineered zinc finger protein that binds to and regulates expression of the gene encoding pigment epithelium-derived factor (PEDF) wherein the protein comprises six zinc fingers and the amino acid sequence of the recognition region of the zinc fingers is as follows: F1: RSDALSR (SEQ ID NO: 14); F2: QSGDLTR (SEQ ID NO:15); F3: QSGDLTR (SEQ ID NO:15); F4: TSGHLSR (SEQ ID NO:16); F5: RSDHLSN (SEQ ID NO:17); F6: QSATRIT (SEQ ID NO:18). Any of the engineered zinc finger proteins described herein may further comprise one or more functional domains, for example one or more activation domains (e.g., VP16 and/or p65 activation domains) or one or more repression domains. In certain embodiments, the engineered zinc finger protein comprises two p65 activation domains.

In another aspect, provided herein are polynucleotides encoding any of the engineered zinc finger proteins that bind to and regulate expression of a gene encoding PEDF. The polynucleotides may further comprise sequences encoding additional proteins, for instance, sequences encoding additional zinc finger proteins, for example engineered zinc finger proteins that bind to and regulate expression of one or more genes involved in angiogenesis (e.g., one or more VEGF genes) and/or cancer (e.g., one or more cytokine-encoding genes).

Thus, in certain embodiments, provided herein are polynucleotides encoding two engineered zinc finger proteins, wherein the first zinc finger protein comprises six zinc fingers and the amino acid sequence of the recognition region of the zinc fingers is as follows: F1: RSDALSR (SEQ ID NO:14); F2: QSGDLTR (SEQ ID NO:15); F3: QSGDLTR (SEQ ID NO:15); F4: TSGHLSR (SEQ ID NO:16); F5: RSDHLSN (SEQ ID NO: 17); F6: QSATRIT (SEQ ID NO: 18); and wherein the second zinc finger protein comprises three zinc fingers and the amino acid sequence of the recognition region of the zinc fingers is as follows: F1: DRSNLTR (SEQ ID NO: 83); F2: TSGHLSR (SEQ ID NO: 16); F3: RSDHLSR (SEQ ID NO: 84).

In other embodiments, provided herein are polynucleotides encoding two engineered zinc finger proteins, wherein the first zinc finger protein comprises six zinc fingers and the amino acid sequence of the recognition region of the zinc fingers is as follows: F1: RSDALSR (SEQ ID NO:14); F2: QSGDLTR (SEQ ID NO:15); F3: QSGDLTR (SEQ ID NO:15); F4: TSGHLSR (SEQ ID NO:16); F5: RSDHLSN (SEQ ID NO:17); F6: QSATRIT (SEQ ID NO:18); and wherein the second zinc finger protein comprises six zinc fingers and the amino acid sequence of the recognition region of each zinc fingers is as follows: F1: RSDALSE (SEQ ID NO:65); F2: DSSHRTR (SEQ ID NO:60); F3: RSDHLSA (SEQ ID NO:61); F4: ANSNRIK (SEQ ID NO:62); F5: QSSDLSR (SEQ ID NO:58); F6: RSDALAR (SEQ ID NO:32).

The polynucleotides encoding two zinc finger proteins may further comprise an internal ribosome entry site (IRES), or a sequence encoding a 2A peptide, disposed between the sequences encoding the first and second zinc finger proteins. In addition, the sequences encoding one or both the engineered zinc finger proteins may be operably linked to inducible or tissue-specific promoters. For example, the sequences encoding the first and/or second zinc finger proteins may operably linked to a tumor-specific promoter (e.g., an E2F promoter, a survivin promoter, a human telomerase reverse transcriptase (hTERT) promoter, a COX-2 promoter, an EGD-2 promoter or an ELF-1 promoter) or a hypoxia-specific promoter.

In another aspect, methods of modulating angiogenesis in an organism by regulating expression of the endogenous PEDF gene are provided. In certain embodiments, the endogenous PEDF gene is regulated by an engineered zinc finger protein as described herein. The PEDF gene may be activated, for example when the engineered zinc finger protein comprises one or more activation domains, or may be repressed, for example when the engineered zinc finger protein comprises one or more repressor domains.

In another aspect, provided herein are methods for the treatment of ocular neovascularization in an organism, wherein the methods comprise activating expression of the endogenous PEDF gene in one or more cells of the organism. In a preferred embodiment, expression of the endogenous PEDF gene is activated using any of the engineered zinc finger proteins described herein, wherein the engineered zinc finger protein(s) bind to a target site in the PEDF gene. In certain embodiments, the method further comprises inhibiting the expression of an endogenous gene encoding a vascular endothelial growth factor (VEGF), for example VEGF-A, in one or more cells of the organism. Inhibition of the VEGF gene may be achieved by binding of a second engineered zinc finger protein to a target site in the endogenous VEGF (e.g., VEGF-A) gene. In certain embodiments, the second zinc finger protein comprises three zinc fingers and the amino acid sequence of the recognition region of each zinc fingers is as follows: F1: DRSNLTR (SEQ ID NO: 83); F2: TSGHLSR (SEQ ID NO: 16); and F3: RSDHLSR (SEQ ID NO: 84). The second zinc finger protein may further comprise a repression domain, for example a v-erbA repression domain and/or a KOX repression domain. In any of these methods, the ocular neovascularization be age-related macular degeneration (AMD, diabetic retinopathy (DR) and/or retinopathy of prematurity.

In yet another aspect, provided herein are methods for the treatment of a malignancy in an organism, wherein the methods comprise activating expression of the endogenous PEDF gene in one or more cells of the organism. In certain embodiments, expression of the endogenous PEDF gene is activated by binding of a first engineered zinc finger protein to a target site in the endogenous PEDF gene, for example any of the engineered zinc finger proteins as described herein. Any of these methods may further comprise the step of activating the expression of an endogenous gene encoding a cytokine (e.g., GM-CSF) in one or more cells of the organism, e.g., by binding of a second engineered zinc finger protein to a target site in the endogenous GM-CSF gene. In certain embodiments, the second zinc finger protein comprises six zinc fingers and the amino acid sequence of the recognition region of each zinc fingers is as follows: F1: RSDALSE (SEQ ID NO:65); F2: DSSHRTR (SEQ ID NO:60); F3: RSDHLSA (SEQ ID NO:61); F4: ANSNRIK (SEQ ID NO:62); F5: QSSDLSR (SEQ ID NO:58); F6: RSDALAR (SEQ ID NO:32). The second zinc finger protein may further comprise a functional domain, for example, an activation domain such as p65 and/or VP16. Any malignancy may be treated, including, for example, head and neck cancer, glioblastoma, prostate cancer and pancreatic cancer.

In any of the methods described herein, the zinc finger proteins may be introduced in protein and/or polynucleotide forms. Further, the proteins and/or polynucleotides may be introduced in any manner, for example into one or more retinal epithelial cells or directly into a tumor. Introduction may also be ex vivo, for example to endothelial or mesenchymal stem cell and the stem cell, which stem cells are subsequently introduced into the organism.

Polynucleotides encoding engineered zinc finger proteins may be introduced encapsidated in a viral vector, for example an adeno-associated virus (AAV, e.g., AAV Type 2, AAV Type 4), replicating Adenovirus, nonreplicating Adenovirus (e.g., Adenovirus Type 5), lentivirus, and Herpes simplex virus. In certain embodiments, the viral vector replicates preferentially in tumor cells.

In any of the methods described herein, the organism may a mammal, for example a human.

The present invention thus includes, but is not limited to, the following numbered embodiments:

1. An engineered zinc finger protein that binds to and regulates expression of the gene encoding pigment epithelium-derived factor (PEDF) wherein the protein comprises six zinc fingers and the amino acid sequence of the recognition region of the zinc fingers is as follows:

| F1: | RSDALSR | (SEQ ID NO:14) |
|---|---|---|
| F2: | QSGDLTR | (SEQ ID NO:15) |
| F3: | QSGDLTR | (SEQ ID NO:15) |
| F4: | TSGHLSR | (SEQ ID NO:16) |
| F5: | RSDHLSN | (SEQ ID NO:17) |
| F6: | QSATRIT | (SEQ ID NO:18). |

2. An engineered zinc finger protein according to 1, further comprising a functional domain.

3. An engineered zinc finger protein according to 2, wherein the functional domain is an activation domain.

4. An engineered zinc finger protein according to 3, wherein the activation domain is selected from the group consisting of the VP16 activation domain, the VP64 activation domain and the p65 activation domain.

5. An engineered zinc finger protein according to 4, comprising two p65 activation domains.

6. An engineered zinc finger protein according to 2, wherein the functional domain is a repression domain.

6A. A polynucleotide encoding an engineered zinc finger protein according to any of 1-6.

6B. A cell comprising an engineered zinc finger protein of any of 1-6 or a polynucleotide of 6A.

7. A method for modulating angiogenesis in an organism by regulating expression of the endogenous PEDF gene.

8. The method of 7, wherein expression of the endogenous PEDF gene is regulated by an engineered zinc finger protein.

9. The method of 8 wherein the zinc finger protein is any of 1 to 6.

10. The method of 7, wherein expression of the PEDF gene is activated.

11. The method of 10, wherein the zinc finger protein is the protein of 4.

12. The method of 10, wherein the zinc finger protein is the protein of 5.

13. The method of 7, wherein expression of the PEDF gene is repressed.

14. The method of 7, wherein the organism is a mammal.

15. The method of 14, wherein the mammal is a human.

16. A method for the treatment of ocular neovascularization in an organism, wherein the method comprises activating expression of the endogenous PEDF gene in one or more cells of the organism.

17. The method of 16, wherein expression of the endogenous PEDF gene is activated by binding of a first engineered zinc finger protein to a target site in the endogenous PEDF gene.

18. The method of 17, wherein the zinc finger protein is the protein of any of 1 to 6.

19. The method of 17, wherein the zinc finger protein is the protein of 4.

20. The method of 17, wherein the zinc finger protein is the protein of 5.

21. The method of 16, wherein the method further comprises inhibiting the expression of an endogenous gene encoding a vascular endothelial growth factor (VEGF) in one or more cells of the organism.

22. The method of 21, wherein the endogenous gene encoding a VEGF encodes vascular endothelial growth factor A (VEGF-A).

23. The method of 22, wherein expression of the endogenous VEGF-A gene is inhibited by binding of a second engineered zinc finger protein to a target site in the endogenous VEGF-A gene.

24. The method of 23, wherein the second zinc finger protein comprises three zinc fingers and the amino acid sequence of the recognition region of each zinc fingers is as follows:

```
F1:     DRSNLTR      (SEQ ID NO:83)
F2:     TSGHLSR      (SEQ ID NO:16)
F3:     RSDHLSR      (SEQ ID NO:84).
```

25. The method of 24, wherein the second zinc finger protein further comprises a repression domain.

26. The method of 25, wherein the repression domain is selected from the group consisting of the v-erbA repression domain and the KOX repression domain.

27. The method of 16, wherein the ocular neovascularization occurs in a disease selected from the group consisting of age-related macular degeneration (AMD, diabetic retinopathy (DR) and retinopathy of prematurity.

28. A polynucleotide encoding two engineered zinc finger proteins, wherein the first zinc finger protein comprises six zinc fingers and the amino acid sequence of the recognition region of the zinc fingers is as follows:

```
F1:     RSDALSR      (SEQ ID NO:14)
F2:     QSGDLTR      (SEQ ID NO:15)
F3:     QSGDLTR      (SEQ ID NO:15)
F4:     TSGHLSR      (SEQ ID NO:16)
F5:     RSDHLSN      (SEQ ID NO:17)
F6:     QSATRIT      (SEQ ID NO:18); and
``` wherein the second zinc finger protein comprises three zinc fingers and the amino acid sequence of the recognition region of the zinc fingers is as follows:

```
F1:     DRSNLTR      (SEQ ID NO:83)
F2:     TSGHLSR      (SEQ ID NO:16)
F3:     RSDHLSR      (SEQ ID NO:84).
```

29. The polynucleotide of 28, further comprising an internal ribosome entry site (IRES) disposed between the sequences encoding the first and second zinc finger proteins.

30. The polynucleotide of 28, further comprising a sequence encoding a 2A peptide disposed between the sequences encoding the first and second zinc finger proteins.

31. A method for the treatment of ocular neovascularization in an organism, wherein the method comprises introducing the polynucleotide of any of 28, 29 or 30 into one or more cells of the organism.

32. The method of 31, in which the polynucleotide is introduced into one or more retinal epithelial cells.

33. The method of 31, in which the polynucleotide is encapsidated in a viral vector selected from the group consisting of adeno-associated virus (AAV), Adenovirus and lentivirus.

34. The method of 33, in which the viral vector is an adeno-associated virus (AAV).

35. The method of 34, in which the viral vector is AAV Type 2 or AAV Type 4.

36. The method of 31, wherein the organism is a mammal.

37. The method of 36, wherein the mammal is a human.

38. A method for the treatment of a malignancy in an organism, wherein the method comprises activating expression of the endogenous PEDF gene in one or more cells of the organism.

39. The method of 38, wherein expression of the endogenous PEDF gene is activated by binding of a first engineered zinc finger protein to a target site in the endogenous PEDF gene.

40. The method of 39 wherein the zinc finger protein is the protein of any of 1 to 6.

41. The method of 39 wherein the zinc finger protein is the protein of 4.

42. The method of 39 wherein the zinc finger protein is the protein of 5.

43. The method of 38, wherein the method further comprises activating the expression of an endogenous gene encoding a cytokine in one or more cells of the organism.

44. The method of 43, wherein the cytokine is granulocyte-macrophage colony-stimulating factor (GM-CSF).

45. The method of 44, wherein expression of the endogenous GM-CSF gene is activated by binding of a second engineered zinc finger protein to a target site in the endogenous GM-CSF gene.

46. The method of 45, wherein the second zinc finger protein comprises six zinc fingers and the amino acid sequence of the recognition region of each zinc fingers is as follows:

```
F1:     RSDALSE     (SEQ ID NO:65)
F2:     DSSHRTR     (SEQ ID NO:60)
F3:     RSDHLSA     (SEQ ID NO:61)
F4:     ANSNRIK     (SEQ ID NO:62)
F5:     QSSDLSR     (SEQ ID NO:58)
F6:     RSDALAR     (SEQ ID NO:32).
```

47. The method of 46, wherein the second zinc finger protein further comprises an activation domain.

48. The method of 47, wherein the activation domain is selected from the group consisting of the p65 activation domain and the VP16 activation domain.

49. The method of 38, wherein the malignancy occurs in a disease selected from the group consisting of head and neck cancer, glioblastoma, prostate cancer and pancreatic cancer.

50. A polynucleotide encoding two engineered zinc finger proteins, wherein the first zinc finger protein comprises six zinc fingers and the amino acid sequence of the recognition region of the zinc fingers is as follows:

```
F1:     RSDALSR     (SEQ ID NO:14)
F2:     QSGDLTR     (SEQ ID NO:15)
F3:     QSGDLTR     (SEQ ID NO:15)
F4:     TSGHLSR     (SEQ ID NO:16)
F5:     RSDHLSN     (SEQ ID NO:17)
F6:     QSATRIT     (SEQ ID NO:18); and
``` wherein the second zinc finger protein comprises six zinc fingers and the amino acid sequence of the recognition region of each zinc fingers is as follows:

```
F1:     RSDALSE     (SEQ ID NO:65)
F2:     DSSHRTR     (SEQ ID NO:60)
F3:     RSDHLSA     (SEQ ID NO:61)
F4:     ANSNRIK     (SEQ ID NO:62)
F5:     QSSDLSR     (SEQ ID NO:58)
F6:     RSDALAR     (SEQ ID NO:32).
```

51. The polynucleotide of 50, further comprising an internal ribosome entry site (IRES) disposed between the sequences encoding the first and second zinc finger proteins.

52. The polynucleotide of 50, further comprising a sequence encoding a 2A peptide disposed between the sequences encoding the first and second zinc finger proteins.

53. The polynucleotide of 50, wherein sequences encoding the first zinc finger protein are operably linked to a tumor-specific promoter.

54. The polynucleotide of 50, wherein sequences encoding the second zinc finger protein are operably linked to a tumor-specific promoter.

55. The polynucleotide of 50, wherein sequences encoding the first and second zinc finger proteins are operably linked to a tumor-specific promoter.

56. The polynucleotide of any of 53, 54 or 55 wherein the tumor specific promoter is selected from the group consisting of the E2F promoter, the survivin promoter, the human telomerase reverse transcriptase (hTERT) promoter, the COX-2 promoter, the EGD-2 promoter and the ELF-1 promoter.

57. The polynucleotide of 56, wherein the tumor-specific promoter is the E2F promoter.

58. The polynucleotide of 50, wherein sequences encoding the first zinc finger protein are operably linked to a hypoxia-specific promoter.

59. The polynucleotide of 50, wherein sequences encoding the second zinc finger protein are operably linked to a hypoxia-specific promoter.

60. The polynucleotide of 50, wherein sequences encoding the first zinc finger protein are operably linked to a tissue-specific promoter.

61. The polynucleotide of 50, wherein sequences encoding the second zinc finger protein are operably linked to a tissue-specific promoter.

62. A method for the treatment of a malignancy in an organism, wherein the method comprises introducing the polynucleotide according to any of 50 to 56 into one or more cells of the organism.

63. A method for the treatment of a malignancy in an organism, wherein the method comprises introducing the polynucleotide of 57 into one or more cells of the organism.

64. The method of 62, in which the polynucleotide is introduced into a tumor.

65. The method of 62, in which the polynucleotide is introduced into an endothelial or mesenchymal stem cell and the stem cell is subsequently introduced into the organism.

66. The method of 62, in which the polynucleotide is encapsidated in a viral vector selected from the group consisting of adeno-associated virus (AAV), Adenovirus and Herpes simplex virus.

67. The method of 66, in which the viral vector is an Adenovirus.

68. The method of 67, wherein the adenovirus vector replicates preferentially in tumor cells.

69. The method of 67, in which the adenovirus vector is a non-replicating adenovirus vector.

70. The method of 69, in which the viral vector is Adenovirus Type 5.

71. The method of 62, wherein the organism is a human.

72. The method of 62, wherein the malignancy occurs in a disease selected from the group consisting of head and neck cancer, glioblastoma, prostate cancer and pancreatic cancer.

73. A polynucleotide encoding the engineered zinc finger protein of any of 1-6.

BRIEF DESCRIPTION OF THE DRAWINGS

FIG. 3 is a graph depicting levels of PEDF RNA (normalized to 18S RNA levels) in mouse Neuro2A cells transfected with expression vectors encoding ZFP No. 6078 or empty vector, as measured by Taqman™ analysis. ZFP No. 6078 increased levels of PEDF expression in mouse Neuro2a cells.

FIG. 4 is a reproduction of a protein blot and depicts levels of secreted PEDF in mouse neuro2a cells. ZFP 6078 increased levels of secreted PEDF as compared to controls.

DETAILED DESCRIPTION

Figure 1:
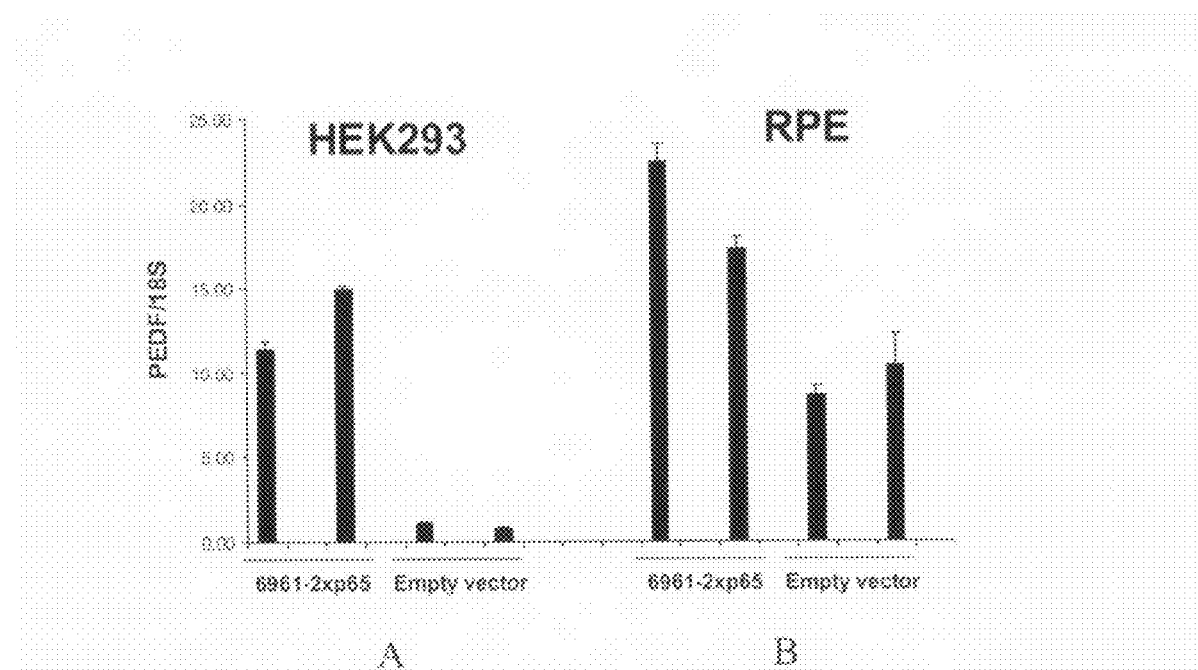
FIGS. 1A and 1B are graphs depicting levels of PEDF mRNA (normalized to 18S RNA levels) in cells transfected with expression vectors encoding ZFP No. 6961 or empty vector, as measured by Taqman™ analysis. ZFP No. 6961 increased levels of PEDF expression in HEK293 cells (FIG. 1A) and in ARPE-19 (RPE) cells (FIG. 1B), as compared to levels seen with empty vector control transfections.

Disclosed herein are compositions that modulate expression of a PEDF gene. PEDF is normally expressed in a variety of cell types and acts to inhibit abnormal neovascularization and angiogenesis. Therefore, compositions described herein that activate PEDF expression are useful in treating a variety of conditions that are associated with, or exhibit, excessive angiogenesis, including but not limited to, age-related macular degeneration and malignant tumors (e.g., head and neck cancer, glioblastoma, prostate cancer and pancreatic cancer).

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

DEFINITIONS

The term "zinc finger protein" or "ZFP" refers to a protein having DNA binding domains that are stabilized by zinc. The individual DNA binding domains are typically referred to as "fingers" A ZFP has least one finger, typically two, three, four, five, six or more fingers. Individual fingers are also referred to as F1, F2, etc. Each finger binds from two to four base pairs of DNA, typically three or four base pairs of DNA. A ZFP binds to a nucleic acid sequence called a target site or target segment. Each finger typically comprises an approximately 30 amino acid, zinc-chelating, DNA-binding subdomain. An exemplary motif characterizing one class of these proteins ($C_2H_2$ class) is -Cys-(X)2-4-Cys-(X)12-His-(X)3-5-His (where X is any amino acid) (SEQ ID NO:1). Additional classes of zinc finger proteins are known and are useful in the practice of the methods, and in the manufacture and use of the compositions disclosed herein (see, e.g., Rhodes et al. (1993) Scientific American 268:56-65). Studies have demonstrated that a single zinc finger of this class consists of an alpha helix containing the two invariant histidine residues coordinated with zinc along with the two cysteine residues of a single beta turn (see, e.g., Berg & Shi, Science 271:1081-1085 (1996)).

A "target site" is the nucleic acid sequence recognized by a ZFP. A single target site typically has about four to about ten base pairs. Typically, a two-fingered ZFP recognizes a four to seven base pair target site, a three-fingered ZFP recognizes a six to ten base pair target site, and a six-fingered ZFP recognizes two adjacent nine to ten base pair target sites.

A "target subsite" or "subsite" is the portion of a DNA target site that is bound by a single zinc finger, excluding cross-strand interactions. Thus, in the absence of cross-strand interactions, a subsite is generally three nucleotides in length. In cases in which a cross-strand interaction occurs (i.e., a "D-able subsite," see co-owned WO 00/42219) a subsite is four nucleotides in length and overlaps with another 3- or 4-nucleotide subsite.

"Kd" refers to the dissociation constant for a binding molecule, i.e., the concentration of a compound (e.g., a zinc finger protein) that gives half maximal binding of the compound to its target (i.e., half of the compound molecules are bound to the target) under given conditions (i.e., when [target]<<Kd), as measured using a given assay system (see, e.g., U.S. Pat. No. 5,789,538). The assay system used to measure the Kd should be chosen so that it gives the most accurate measure of the actual Kd of the ZFP. Any assay system can be used, as long is it gives an accurate measurement of the actual Kd of the ZFP. In one embodiment, the Kd for a ZFP is measured using an electrophoretic mobility shift assay ("EMSA"). Unless an adjustment is made for ZFP purity or activity, the Kd calculations may result in an overestimate of the true Kd of a given ZFP. Preferably, the Kd of a ZFP used to modulate transcription of a gene is less than about 100 nM, more preferably less than about 75 nM, more preferably less than about 50 nM, most preferably less than about 25 nM.

A "gene," for the purposes of the present disclosure, includes a DNA region encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

The term "PEDF gene" refers generally to any member of the PEDF family of genes or collection of genes from the PEDF family having a native PEDF nucleotide sequence, as well as variants and modified forms regardless of origin or mode of preparation. The PEDF genes can be from any source. Typically, the PEDF genes refer to PEDF genes in mammals, particularly humans. A PEDF gene having a native nucleotide sequence is a gene having the same nucleotide sequence as a PEDF gene as obtained from nature (i.e., a naturally occurring PEDF gene). The term also includes variants of specific isoforms. The term also encompasses allelic variants, other isoforms resulting from alternative exon splicing, forms that are functionally equivalent to native sequences, and nucleic acids that are substantially identical to a native PEDF gene.

The term "VEGF gene" refers generally to any member of the VEGF family of genes or collection of genes from the VEGF family having a native VEGF nucleotide sequence, as well as variants and modified forms regardless of origin or mode of preparation. The VEGF genes can be from any source. Typically, the VEGF genes refer to VEGF genes in mammals, particularly humans. A VEGF gene having a native nucleotide sequence is a gene having the same nucleotide sequence as a VEGF gene as obtained from nature (i.e., a naturally occurring VEGF gene). More specifically, the term includes VEGF-A (including the isoforms VEGF-A121, VEGF-A145, VEGF-A165, VEGF-A189, and VEGF-A206, see, Leung, et al. (1989) Science 246:1306-1309; Keck, et al. (1989) Science 246:1309-1312; Conn et al. (1990) Proc. Natl. Acad. Sci. USA 87:2628-2632; U.S. Pat. Nos. 5,240,848; 5,194,596; 5,219,739; and 5,332,671); VEGF-B (including the isoforms VEGF-B167, and VEGF-B186, see, PCT Publication WO 96/26736, WO 96/27007, WO 00/09148 and U.S. Pat. Nos. 5,840,693, 5,607,918, and 5,928,939); VEGF-C (see, Joukov et al., (1996) EMBO J. 15:290-298; Lee et al. (1996) Proc. Natl. Acad. Sci. USA 93:1988-1992; U.S. Pat. Nos. 5,935,820; 6,130,071; 5,776,755; 5,932,540; 5,994,300 and 6,040,157; as well as PCT Publications WO 95/24473; WO 96/39515; WO 97/05250; WO 97/09427; WO 97/17442; WO 98/33917; WO 00/45835 and WO 99/46364, EP 0 476 983 B1); VEGF-D (see, PCT Publications WO 98/07832, WO 98/24811; and WO 99/33485); VEGF-E (various VEGF-like proteins from orf virus strains as described for example in WO 99/4767); VEGF-H; VEGF-R; VEGF-X; VEGF-138; and P1GF (both P1GF-1 and P1GF-2). The term also includes variants of specific isoforms. For example, the term includes not only the isoform VEGF-145, but also VEGF-145-I, VEGF-145-II, and VEGF-145-III. The term also encompasses allelic variants, other isoforms resulting from alternative exon splicing, forms that are functionally equivalent to native sequences, and nucleic acids that are substantially identical to a native VEGF gene.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Gene activation" and "up-regulation" refer to any process that results in an increase in production of a gene product. A gene product can be either RNA (including, but not limited to, mRNA, rRNA, tRNA, and structural RNA) or protein. Accordingly, gene activation includes those processes that increase transcription of a gene and/or translation of a mRNA. Examples of gene activation processes that increase transcription include, but are not limited to, those that facilitate formation of a transcription initiation complex, those that increase transcription initiation rate, those that increase transcription elongation rate, those that increase processivity of transcription and those that relieve transcriptional repression (by, for example, blocking the binding of a transcriptional repressor). Gene activation can constitute, for example, inhibition of repression as well as stimulation of expression above an existing level. Examples of gene activation processes which increase translation include those that increase translational initiation, those that increase translational elongation and those that increase mRNA stability. In general, gene activation comprises any detectable increase in the production of a gene product, in some instances an increase in production of a gene product by about 2-fold, in other instances from about 2- to about 5-fold or any integer therebetween, in still other instances between about 5- and about 10-fold or any integer therebetween, in yet other instances between about 10- and about 20-fold or any integer therebetween, sometimes between about 20- and about 50-fold or any integer therebetween, in other instances between about 50- and about 100-fold or any integer therebetween, and in yet other instances between 100-fold or more.

"Gene repression," "inhibition of gene expression" and "down-regulation" refer to any process which results in a decrease in production of a gene product. A gene product can be either RNA (including, but not limited to, mRNA, rRNA, tRNA, and structural RNA) or protein. Accordingly, gene repression includes those processes which decrease transcription of a gene and/or translation of a mRNA. Examples of gene repression processes which decrease transcription include, but are not limited to, those which inhibit formation of a transcription initiation complex, those which decrease transcription initiation rate, those which decrease transcription elongation rate, those which decrease processivity of transcription and those which antagonize transcriptional activation (by, for example, blocking the binding of a transcriptional activator). Gene repression can constitute, for example, prevention of activation as well as inhibition of expression below an existing level. Examples of gene repression processes which decrease translation include those which decrease translational initiation, those which decrease translational elongation and those which decrease mRNA stability. Transcriptional repression includes both reversible and irreversible inactivation of gene transcription. In general, gene repression comprises any detectable decrease in the production of a gene product, in some instances a decrease in production of a gene product by about 2-fold, in other instances from about 2- to about 5-fold or any integer therebetween, in yet other instances between about 5- and about 10-fold or any integer therebetween, in still other instances between about 10- and about 20-fold or any integer therebetween, sometimes between about 20- and about 50-fold or any integer therebetween, in other instances between about 50- and about 100-fold or any integer therebetween, in still other instances 100-fold or more. In yet other instances, gene repression results in complete inhibition of gene expression, such that no gene product is detectable.

"Modulation" refers to a change in the level or magnitude of an activity or process. The change can be either an increase or a decrease. For example, modulation of gene expression includes both gene activation and gene repression. Modulation can be assayed by determining any parameter that is indirectly or directly affected by the expression of the target gene. Such parameters include, e.g., changes in RNA or protein levels, changes in protein activity, changes in product levels, changes in downstream gene expression, changes in reporter gene transcription (luciferase, CAT, β-galactosidase, β-glucuronidase, green fluorescent protein (see, e.g., Mistili & Spector, Nature Biotechnology 15:961-964 (1997)); changes in signal transduction, phosphorylation and dephosphorylation, receptor-ligand interactions, second messenger concentrations (e.g., cGMP, cAMP, IP3, and Ca2+), cell growth, and neovascularization. These assays can be in vitro, in vivo, and ex vivo. Such functional effects can be measured by any means known to those skilled in the art, e.g., measurement of RNA or protein levels, measurement of RNA stability, identification of downstream or reporter gene expression, e.g., via chemiluminescence, fluorescence, colorimetric reactions, antibody binding, inducible markers, ligand binding assays; changes in intracellular second messengers such as cGMP and inositol triphosphate (IP3); changes in intracellular calcium levels; cytokine release, and the like.

The terms "identical" or percent "identity," in the context of two or more nucleic acids or polypeptides, refer to two or more sequences or subsequences that are the same or have a specified percentage of nucleotides or amino acid residues that are the same, when compared and aligned for maximum correspondence, as measured using a sequence comparison algorithm such as those described below for example, or by visual inspection.

The phrase "substantially identical," in the context of two nucleic acids or polypeptides, refers to two or more sequences or subsequences that have at least 75%, preferably at least 85%, more preferably at least 90%, 95% or higher or any integral value therebetween nucleotide or amino acid residue identity, when compared and aligned for maximum correspondence, as measured using a sequence comparison algorithm such as those described below for example, or by visual inspection. Preferably, the substantial identity exists over a region of the sequences that is at least about 10, preferably about 20, more preferable about 40-60 residues in length or any integral value therebetween, preferably over a longer region than 60-80 residues, more preferably at least about 90-100 residues, and most preferably the sequences are substantially identical over the full length of the sequences being compared, such as the coding region of a nucleotide sequence for example.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection [see generally, Current Protocols in Molecular Biology, (Ausubel, F. M. et al., eds.) John Wiley & Sons, Inc., New York (1987-1999, including supplements such as supplement 46 (April 1999)]. Use of these programs to conduct sequence comparisons are typically conducted using the default parameters specific for each program.

Another example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. This is referred to as the neighborhood word score threshold (Altschul et al, supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For determining sequence similarity the default parameters of the BLAST programs are suitable. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix. The TBLATN program (using protein sequence for nucleotide sequence) uses as defaults a word length (W) of 3, an expectation (E) of 10, and a BLOSUM 62 scoring matrix. (see Henikoff & Henikoff, Proc. Natl. Acad. Sci. USA 89:10915 (1989)). 11171 In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another indication that two nucleic acid sequences are substantially identical is that the two molecules hybridize to each other under stringent conditions. "Hybridizes substantially" refers to complementary hybridization between a probe nucleic acid and a target nucleic acid and embraces minor mismatches that can be accommodated by reducing the stringency of the hybridization media to achieve the desired detection of the target polynucleotide sequence. The phrase "hybridizing specifically to", refers to the binding, duplexing, or hybridizing of a molecule only to a particular nucleotide sequence under stringent conditions when that sequence is present in a complex mixture (e.g., total cellular) DNA or RNA.

A further indication that two nucleic acid sequences or polypeptides are substantially identical is that the polypeptide encoded by the first nucleic acid is immunologically cross reactive with the polypeptide encoded by the second nucleic acid, as described below.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every polynucleotide sequence described herein which encodes a polypeptide also describes every possible silent variation, except where otherwise noted. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence.

A polypeptide is typically substantially identical to a second polypeptide, for example, where the two peptides differ only by conservative substitutions. A "conservative substitution," when describing a protein, refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well-known in the art. See, e.g., Creighton (1984) Proteins, W.H. Freeman and Company. In addition, individual substitutions, deletions or additions which alter, add or delete a single amino acid or a small percentage of amino acids in an encoded sequence are also "conservatively modified variations."

"Functional fragment" or "functional equivalent" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid, binding to a regulatory molecule) are well-known in the art. Similarly, methods for determining protein function are well-known. For example, the DNA-binding function of a polypeptide can be determined, for example, by filter-binding, electrophoretic mobility-shift, or immunoprecipitation assays. See Ausubel et al., supra. The ability of a protein to interact with another protein can be determined, for example, by co-immunoprecipitation, two-hybrid assays or complementation, both genetic and biochemical. See, for example, Fields et al. (1989) Nature 340: 245-246; U.S. Pat. No. 5,585,245 and PCT WO 98/44350.

The terms "nucleic acid," "polynucleotide," and "oligonucleotide" are used interchangeably and refer to a deoxyribonucleotide or ribonucleotide polymer in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties. In general, an analogue of a particular nucleotide has the same base-pairing specificity; i.e., an analogue of A will base-pair with T. Thus, the term polynucleotide sequence is the alphabetical representation of a polynucleotide molecule. This alphabetical representation can be input into databases in a computer having a central processing unit and used for bioinformatics applications such as functional genomics and homology searching. The terms additionally encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs). The nucleotide sequences are displayed herein in the conventional 5'-3' orientation.

An "exogenous molecule" is a molecule that is not normally present in a cell, but can be introduced into a cell by one or more genetic, biochemical or other methods. Normal presence in the cell is determined with respect to the particular developmental stage and environmental conditions of the cell. Thus, for example, a molecule that is present only during embryonic development of muscle is an exogenous molecule with respect to an adult muscle cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., protein or nucleic acid (i.e., an exogenous gene), providing it has a sequence that is different from an endogenous molecule. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous molecule" is one that is normally present in a particular cell at a particular developmental stage under particular environmental conditions.

The phrase "adjacent to a transcription initiation site" refers to a target site that is within about 50 bases either upstream or downstream of a transcription initiation site. "Upstream" of a transcription initiation site refers to a target site that is more than about 50 bases 5' of the transcription initiation site (i.e., in the non-transcribed region of the gene). "Downstream" of a transcription initiation site refers to a target site that is more than about 50 bases 3' of the transcription initiation site.

A "fusion molecule" is a molecule in which two or more subunit molecules are linked, typically covalently. The subunit molecules can be the same chemical type of molecule, or can be different chemical types of molecules. Examples of the first type of fusion molecule include, but are not limited to, fusion polypeptides (for example, a fusion between a ZFP DNA-binding domain and a transcriptional activation domain) and fusion nucleic acids (for example, a nucleic acid encoding the fusion polypeptide described supra). Examples of the second type of fusion molecule include, but are not limited to, a fusion between a triplex-forming nucleic acid and a polypeptide, and a fusion between a minor groove binder and a nucleic acid.

A "regulatory domain" or "functional domain" refers to a protein or a protein domain that has transcriptional modulation activity when tethered to a DNA binding domain, i.e., a ZFP. Typically, a regulatory domain is covalently or non-covalently linked to a ZFP (e.g., to form a fusion molecule) to effect transcription modulation. Regulatory domains can be activation domains or repression domains. Activation domains include, but are not limited to, VP16, VP64 and the p65 subunit of nuclear factor Kappa-B. Repression domains include, but are not limited to, KRAB MBD2B and v-ErbA. Additional regulatory domains include, e.g., transcription factors and co-factors (e.g., MAD, ERD, SID, early growth response factor 1, and nuclear hormone receptors), endonucleases, integrases, recombinases, methyltransferases, histone acetyltransferases, histone deacetylases etc. Activators and repressors include co-activators and co-repressors (see, e.g., Utley et al., Nature 394:498-502 (1998)). Alternatively, a ZFP can act alone, without a regulatory domain, to effect transcription modulation.

The term "operably linked" or "operatively linked" is used with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. An operatively linked transcriptional regulatory sequence is generally joined in cis with a coding sequence, but need not be directly adjacent to it. For example, an enhancer can constitute a transcriptional regulatory sequence that is operatively-linked to a coding sequence, even though they are not contiguous.

With respect to fusion polypeptides, the term "operably linked" or "operatively linked" can refer to the fact that each of the components performs the same function in linkage to the other component as it would if it were not so linked. For example, with respect to a fusion polypeptide in which a ZFP DNA-binding domain is fused to a transcriptional activation domain (or functional fragment thereof), the ZFP DNA-binding domain and the transcriptional activation domain (or functional fragment thereof) are in operative linkage if, in the fusion polypeptide, the ZFP DNA-binding domain portion is able to bind its target site and/or its binding site, while the transcriptional activation domain (or functional fragment thereof) is able to activate transcription.

The term "recombinant," when used with reference to a cell, indicates that the cell replicates an exogenous nucleic acid, or expresses a peptide or protein encoded by an exogenous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant expression cassette," "expression cassette" or "expression construct" is a nucleic acid construct, generated recombinantly or synthetically, that has control elements that are capable of effecting expression of a structural gene that is operatively linked to the control elements in hosts compatible with such sequences. Expression cassettes include at least promoters and optionally, transcription termination signals. Typically, the recombinant expression cassette includes at least a nucleic acid to be transcribed (e.g., a nucleic acid encoding a desired polypeptide) and a promoter. Additional factors necessary or helpful in effecting expression can also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

A "promoter" is defined as an array of nucleic acid control sequences that direct transcription. As used herein, a promoter typically includes necessary nucleic acid sequences near the start site of transcription, such as, in the case of certain RNA polymerase II type promoters, a TATA element, CCAAT box, SP-1 site, etc. As used herein, a promoter also optionally includes distal enhancer or repressor elements, which can be located as much as several thousand base pairs from the start site of transcription. The promoters often have an element that is responsive to transactivation by a DNA-binding moiety such as a polypeptide, e.g., a nuclear receptor, Gal4, the lac repressor and the like.

A "constitutive" promoter is a promoter that is active under most environmental and developmental conditions.

An "inducible" promoter is a promoter that is active under certain environmental or developmental conditions, for example, hypoxia-dependent promoters that contain hypoxia-response elements (HRE) (e.g., plasminogen activator inhibitor-1 (PAI-1) promoter (Fink et al. (2002) *Blood* 99(6):2077-83); an ADH2 promoter (Passoth et al. (2003) *Yeast* 20(1):39-51).

A "tissue-specific" promoter is a promoter that is active only in certain tissues. For instance, non-limiting examples of tumor-specific promoters include E2F-1, Survivin, cyclooxygenase-2 (COX-2), epithelial glycoprotein 2 (EGP-2), and TERT. Lu et al. (2005) *Gene Ther.* 12(4):330-338.

A "weak promoter" refers to a promoter having about the same activity as a wild type herpes simplex virus ("HSV") thymidine kinase ("tk") promoter or a mutated HSV tk promoter, as described in Eisenberg & McKnight, Mol. Cell. Biol. 5:1940-1947 (1985).

An "expression vector" is a nucleic acid construct, generated recombinantly or synthetically, with a series of specified nucleic acid elements that permit transcription of a particular nucleic acid in a host cell, and optionally integration or replication of the expression vector in a host cell. The expression vector can be part of a plasmid, virus, or nucleic acid fragment, of viral or non-viral origin. Typically, the expression vector includes an "expression cassette," which comprises a nucleic acid to be transcribed operably linked to a promoter. The term expression vector also encompasses naked DNA operably linked to a promoter.

By "host cell" is meant a cell that contains an expression vector or nucleic acid, either of which optionally encodes a ZFP or a ZFP fusion protein. The host cell typically supports the replication or expression of the expression vector. Host cells can be prokaryotic cells such as, for example, E. coli, or eukaryotic cells such as yeast, fungal, protozoal, higher plant, insect, or amphibian cells, or mammalian cells such as CHO, HeLa, 293, COS-1, and the like, e.g., cultured cells (in vitro), explants and primary cultures (in vitro and ex vivo), and cells in vivo.

The term "naturally occurring," as applied to an object, means that the object can be found in nature, as distinct from being artificially produced by humans.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins. The polypeptide sequences are displayed herein in the conventional N-terminal to C-terminal orientation.

A "subsequence" or "segment" when used in reference to a nucleic acid or polypeptide refers to a sequence of nucleotides or amino acids that comprise a part of a longer sequence of nucleotides or amino acids (e.g., a polypeptide), respectively.

"Angiogenesis" broadly refers to the process of developing new blood vessels. The process involves proliferation, migration and tissue infiltration of capillary endothelial cells from pre-existing blood vessels. Angiogenesis is important in normal physiological processes, including for example, follicular growth, embryonal development and wound healing and in pathological processes such as tumor growth and metastasis. The term "modulation" refers to a change in extent, duration, levels, or properties of a physiologic process. For example modulation of angiogenesis could comprise an increase in the formation of new blood vessels or a decrease in the formation of new blood vessels. Modulation of angiogenesis could also refer to the stimulation of the formation of nonpermeable or nonhyperpermeable blood vessels. Various assays for angiogenesis are described herein and in U.S. Patent Publication 20030021776, incorporated by reference in its entirety herein.

The term "neovascularization" refers generally to new blood vessel formation, particularly in abnormal tissue (e.g., neoplastic tissue) or in abnormal positions.

The term "malignancy" refers to a tumor that is capable of anaplasia (dedifferentiation), invasion and/or metastasis.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage.

By an "effective" amount (or "therapeutically effective" amount) of a pharmaceutical composition is meant a sufficient, but nontoxic amount of the agent to provide the desired effect. The term refers to an amount sufficient to treat a subject. Thus, the term therapeutic amount refers to an amount sufficient to remedy a disease state or symptoms, by preventing, hindering, retarding or reversing the progression of the disease or any other undesirable symptoms whatsoever. The term prophylactically effective amount refers to an amount given to a subject that does not yet have the disease, and thus is an amount effective to prevent, hinder or retard the onset of a disease.

Overview

Described herein are compositions, including proteins and polynucleotides encoding these proteins that modulate expression of a PEDF gene. Also described are a variety of methods for modulating angiogenesis; methods for the treatment of ocular neovascularization; and methods of the treatment of a malignancy. In certain embodiments, such methods involve contacting a cell or population of cells such as in an organism, with one or more compositions that bind to specific sequences in one or more PEDF genes. In certain methods, two or more such compositions are administered, wherein at least one ZFP is able to bind to a target site in a PEDF gene.

Thus, provided herein are a variety of compositions that are engineered to specifically recognize and bind to particular nucleic acid segments (target sites), thereby modulating the expression of one or more PEDF genes. The compositions may comprise zinc finger proteins, which may be linked to regulatory domains to create chimeric transcription factors to activate or repress transcription of PEDF genes. With such ZFPs, expression of PEDF gene(s) can be enhanced; with certain other ZFPs, expression can be repressed. In general, the target sites to which the ZFPs bind are sites that result in activation or repression of expression of PEDF gene. The target site can be adjacent to, upstream of, and/or downstream of the transcription start site (defined as nucleotide 0). As indicated above, some of the present ZFPs modulate the expression of a single PEDF gene. Other ZFPs modulate the expression of a plurality of PEDF genes.

By virtue of the ability of the ZFPs to bind to target sites and influence expression of PEDF genes, the ZFPs provided herein can be used in a wide variety of applications. In general, the ZFPs can be used to regulate the growth of a variety of endothelial cells, either by activating or repressing growth. In certain applications, the ZFPs can be used to activate expression of PEDF genes to repress harmful angiogenesis in cell populations, both in vitro and in vivo. Such activation can be utilized for example to inhibit the formation of new blood vessels and capillaries in treatments for conditions with abnormal vascularization. For instance, the ZFPs can be used to inhibit the development of collateral circulation in individuals having tumors that are excessively vascularized and/or in preventing proliferation of the microvascular system in pathologies such as diabetic retinopathy and pathological angiogenesis associated with arthritis.

The ZFPs can also be employed in applications other than therapeutic applications. For instance, the ZFPs can be used to screen for agents capable of countering either activation or repression of PEDF gene expression. Also described herein are nucleic acids that encode the zinc finger proteins. Additionally, agents identified through the screening methods, the nucleic acids encoding the ZFPs and/or the ZFPs themselves can be utilized in pharmaceutical compositions to treat a variety of disorders, such as those just described.

Zinc Finger Proteins

In a preferred aspect, the compositions described herein that are capable of modulating PEDF expression comprise a zinc finger protein. Thus, disclosed herein are zinc finger proteins (ZFPS) that can bind to DNA within a PEDF gene in a sequence-specific manner. As noted, these ZFPs can be used in a variety of applications, including modulating angiogenesis and in treatments for undesirable neovascularization and malignancies. An exemplary motif characterizing one class of these proteins, the C2H2 class, is -Cys-(X)2-4-Cys-(X)12-His-(X)3-5-His (where X is any amino acid) (SEQ ID NO:1). Several structural studies have demonstrated that the finger domain contains an alpha helix containing the two invariant histidine residues and two invariant cysteine residues in a beta turn coordinated through zinc. However, the ZFPs provided herein are not limited to this particular class. Additional classes of zinc finger proteins are known and can also be used in the methods and compositions disclosed herein (see, e.g., Rhodes, et al. (1993) Scientific American 268:56-65). In certain ZFPs, a single finger domain is about 30 amino acids in length. Zinc finger domains are involved not only in DNA-recognition, but also in RNA binding and in protein-protein binding.

The x-ray crystal structure of Zif268, a three-finger domain from a murine transcription factor, has been solved in complex with a cognate DNA-sequence and shows that each finger can be superimposed on the next by a periodic rotation. The structure suggests that each finger interacts independently with DNA over 3 base-pair intervals, with side-chains at positions −1,2,3 and 6 on each recognition helix making contacts with their respective DNA triplet subsites. The amino terminus of Zif268 is situated at the 3' end of the DNA strand with which it makes most contacts. Some zinc fingers can bind to a fourth base in a target segment. If the strand with which a zinc finger protein makes most contacts is designated the target strand, some zinc finger proteins bind to a three base triplet in the target strand and a fourth base on the nontarget strand. The fourth base is complementary to the base immediately 3' of the three base subsite.

The target sites can be located upstream or downstream of the transcriptional start site (defined as nucleotide 0) of the target gene (PEDF) and, indeed, may be significantly upstream of downstream of the start site. Some of the target sites include 9 nucleotides, whereas other sites include 18 nucleotides (see Table 3). One feature of these target sites is that binding of a ZFP, or a fusion protein including a ZFP and one or more regulatory domains, to the target site can affect the level of expression of one or more PEDF genes. Target sites may be unique to a particular PEDF gene or, alternatively, may occur in multiple PEDF genes or multiple places in a single PEDF gene.

Zinc finger proteins are formed from zinc finger components. For example, zinc finger proteins can have one to thirty-seven fingers, commonly having 2, 3, 4, 5 or 6 fingers. A zinc finger protein recognizes and binds to a target site (sometimes referred to as a target segment) that represents a relatively small subsequence within a target gene. Each component finger of a zinc finger protein can bind to a subsite within the target site. The subsite includes a triplet of three contiguous bases all on the same strand (sometimes referred to as the target strand). The subsite may or may not also include a fourth base on the opposite strand that is the complement of the base immediately 3' of the three contiguous bases on the target strand. In many zinc finger proteins, a zinc finger binds to its triplet subsite substantially independently of other fingers in the same zinc finger protein. Accordingly, the binding specificity of zinc finger protein containing multiple fingers is usually approximately the aggregate of the specificities of its component fingers. For example, if a zinc finger protein is formed from first, second and third fingers that individually bind to triplets XXX, YYY, and ZZZ, the binding specificity of the zinc finger protein is 3'XXX YYY ZZZ5'.

The relative order of fingers in a zinc finger protein from N-terminal to C-terminal determines the relative order of triplets in the 3' to 5' direction in the target. See Berg & Shi, Science 271, 1081-1086 (1996). The assessment of binding properties of a zinc finger protein as the aggregate of its component fingers may, in some cases, be influenced by context-dependent interactions of multiple fingers binding in the same protein.

Two or more zinc finger proteins can be linked to have a target specificity that is the aggregate of that of the component zinc finger proteins (see e.g., Kim & Pabo, Proc. Natl. Acad. Sci. U.S.A. 95, 2812-2817 (1998)). For example, a first zinc finger protein having first, second and third component fingers that respectively bind to XXX, YYY and ZZZ can be linked to a second zinc finger protein having first, second and third component fingers with binding specificities, AAA, BBB and CCC. The binding specificity of the combined first and second proteins is thus 3'XXXYYYZZ-Z_AAABBBCCC5', where the underline indicates a short intervening region (typically 0-5 bases of any type). In this situation, the target site can be viewed as comprising two target segments separated by an intervening segment.

Linkage can be accomplished using any of the following peptide linkers: TGEKP (SEQ ID NO:2) (Liu et al., 1997, supra.); (G4S)n (SEQ ID NO:3) (Kim et al., Proc. Natl. Acad. Sci. U.S.A. 93:1156-1160 (1996.); GGRRGGGS; (SEQ ID NO:4) LRQRDGERP; (SEQ ID NO:5) LRQKDGGGSERP; (SEQ ID NO:6) LRQKD(G3S)2ERP (SEQ ID NO:7) Alternatively, flexible linkers can be rationally designed using computer programs capable of modeling both DNA-binding sites and the peptides themselves or by phage display methods. In a further variation, noncovalent linkage can be achieved by fusing two zinc finger proteins with domains promoting heterodimer formation of the two zinc finger proteins. For example, one zinc finger protein can be fused with fos and the other with jun (see Barbas et al., WO 95/119431).

ZFPs may be designed or selected by any suitable method. In certain embodiments, and as described in U.S. Patent Publication 20030021776, incorporated by reference herein in its entirety, ZFPs may be designed by defining and substituting nonconserved positions of a ZFP framework (i.e., positions −1 to +6 of ZFPs such as Sp-1 or TFIIIA) so as to confer a desired binding specificity. A number of substitution rules that assist rational design of zinc finger proteins are described, for example, in International Patent Publications WO 00/42219; WO 00/41566, WO 95/19431, WO 98/54311, WO 96/06166, WO 00/23464 and WO 00/27878; U.S. Pat. Nos. 5,789,538; 6,007,408; 6,013,453; 6,140,081; and 6,140, 466; Desjarlais & Berg, PNAS 90, 2256-2260 (1993); Choo & Klug, PNAS 91, 11163-11167 (1994); Desjarlais & Berg, PNAS 89, 7345-7349 (1992); Jamieson et al., Biochemistry 33:5689-5695 (1994); and Choo et al., WO 98/53057, WO 98/53058; WO 98/53059; WO 98/53060.

Furthermore, any suitable method known in the art can be used to design and construct nucleic acids encoding ZFPs, e.g., phage display, random mutagenesis, combinatorial libraries, computer/rational design, affinity selection, PCR, cloning from cDNA or genomic libraries, synthetic construction and the like. (see, e.g., U.S. Pat. No. 5,786,538; Wu et al., PNAS 92:344-348 (1995); Jamieson et al., Biochemistry 33:5689-5695 (1994); Rebar & Pabo, Science 263:671-673 (1994); Choo & Klug, PNAS 91:11163-11167 (1994); Choo & Klug, PNAS 91: 11168-11172 (1994); Desjarlais & Berg, PNAS 90:2256-2260 (1993); Desjarlais & Berg, PNAS 89:7345-7349 (1992); Pomerantz et al., Science 267:93-96 (1995); Pomerantz et al., PNAS 92:9752-9756 (1995); and Liu et al., PNAS 94:5525-5530 (1997); Griesman & Pabo, Science 275:657-661 (1997); Desjarlais & Berg, PNAS 91:11-99-11103 (1994)). See, also, U.S. Patent Publication 20030021776, incorporated by reference herein in its entirety.

Production of Zinc Finger Proteins

ZFP polypeptides and nucleic acids encoding the same can be made using routine techniques in the field of recombinant genetics. Basic texts disclosing general methods include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)). In addition, nucleic acids less than about 100 bases can be custom ordered from any of a variety of commercial sources, such as The Midland Certified Reagent Company (mcrc@oligos.com), The Great American Gene Company (http://www.genco.com), ExpressGen Inc. (www.expressgen.com), Operon Technologies Inc. (Alameda, Calif.). Similarly, peptides can be custom ordered from any of a variety of sources, such as PeptidoGenic (pkim@ccnet.com), HTI Bio-products, inc. (http://www.htibio.com), BMA Biomedicals Ltd (U.K.), Bio.Synthesis, Inc.

Oligonucleotides can be chemically synthesized according to the solid phase phosphoramidite triester method first described by Beaucage & Caruthers, Tetrahedron Letts. 22:1859-1862 (1981), using an automated synthesizer, as described in Van Devanter et al., Nucleic Acids Res. 12:6159-6168 (1984). Purification of oligonucleotides is by either denaturing polyacrylamide gel electrophoresis or by reverse phase HPLC. The sequence of the cloned genes and synthetic oligonucleotides can be verified after cloning using, e.g., the chain termination method for sequencing double-stranded templates of Wallace et al., Gene 16:21-26 (1981).

Two alternative methods are typically used to create the coding sequences required to express newly designed DNA-binding peptides. One protocol is a PCR-based assembly procedure that utilizes six overlapping oligonucleotides. Three oligonucleotides correspond to "universal" sequences that encode portions of the DNA-binding domain between the recognition helices. These oligonucleotides typically remain constant for all zinc finger constructs. The other three "specific" oligonucleotides are designed to encode the recognition helices. These oligonucleotides contain substitutions primarily at positions-1, 2, 3 and 6 on the recognition helices making them specific for each of the different DNA-binding domains.

The PCR synthesis is carried out in two steps. First, a double stranded DNA template is created by combining the six oligonucleotides (three universal, three specific) in a four cycle PCR reaction with a low temperature annealing step, thereby annealing the oligonucleotides to form a DNA "scaffold." The gaps in the scaffold are filled in by high-fidelity thermostable polymerase, the combination of Taq and Pfu polymerases also suffices. In the second phase of construction, the zinc finger template is amplified by external primers designed to incorporate restriction sites at either end for cloning into a shuttle vector or directly into an expression vector.

An alternative method of cloning the newly designed DNA-binding proteins relies on annealing complementary oligonucleotides encoding the specific regions of the desired ZFP. This particular application requires that the oligonucleotides be phosphorylated prior to the final ligation step. This is usually performed before setting up the annealing reactions. In brief, the "universal" oligonucleotides encoding the constant regions of the proteins (oligos 1, 2 and 3 of above) are annealed with their complementary oligonucleotides. Additionally, the "specific" oligonucleotides encoding the finger recognition helices are annealed with their respective complementary oligonucleotides. These complementary oligos are designed to fill in the region that was previously filled in by polymerase in the above-mentioned protocol. Oligonucleotides complementary to oligos 1 and 6 are engineered to leave overhanging sequences specific for the restriction sites used in cloning into the vector of choice in the following step. The second assembly protocol differs from the initial protocol in the following aspects: the "scaffold" encoding the newly designed ZFP is composed entirely of synthetic DNA thereby eliminating the polymerase fill-in step, additionally the fragment to be cloned into the vector does not require amplification. Lastly, the design of leaving sequence-specific overhangs eliminates the need for restriction enzyme digests of the inserting fragment. Alternatively, changes to ZFP recognition helices can be created using conventional site-directed mutagenesis methods.

Both assembly methods require that the resulting fragment encoding the newly designed ZFP be ligated into a vector. Ultimately, the ZFP-encoding sequence is cloned into an expression vector. Expression vectors that are commonly utilized include, but are not limited to, a modified pMAL-c2 bacterial expression vector (New England BioLabs, Beverly, Mass.) or an eukaryotic expression vector, pcDNA (Promega, Madison, Wis.). The final constructs are verified by sequence analysis.

Any suitable method of protein purification known to those of skill in the art can be used to purify ZFPs (see, Ausubel, supra, Sambrook, supra). In addition, any suitable host can be used for expression, e.g., bacterial cells, insect cells, yeast cells, mammalian cells, and the like.

Expression of a zinc finger protein fused to a maltose binding protein (MBP-ZFP) in bacterial strain JM109 allows for straightforward purification through an amylose column (New England BioLabs, Beverly, Mass.). High expression levels of the zinc finger chimeric protein can be obtained by induction with IPTG since the MBP-ZFP fusion in the pMal-c2 expression plasmid is under the control of the tac promoter (New England BioLabs, Beverly, Mass.). Bacteria containing the MBP-ZFP fusion plasmids are inoculated into 2xYT medium containing 10 µM ZnCl2, 0.02% glucose, plus 50 µg/ml ampicillin and shaken at 37° C. At mid-exponential growth IPTG is added to 0.3 mM and the cultures are allowed to shake. After 3 hours the bacteria are harvested by centrifugation, disrupted by sonication or by passage through a french pressure cell or through the use of lysozyme, and insoluble material is removed by centrifugation. The MBP-ZFP proteins are captured on an amylose-bound resin, washed extensively with buffer containing 20 mM Tris-HCl (pH 7.5), 200 mM NaCl, 5 mM DTT and 50 µM $ZnCl_2$, then eluted with maltose in essentially the same buffer (purification is based on a standard protocol from New England BioLabs. Purified proteins are quantitated and stored for biochemical analysis.

The dissociation constant of a purified protein, e.g., Kd, is typically characterized via electrophoretic mobility shift assays (EMSA) (Buratowski & Chodosh, in Current Protocols in Molecular Biology pp. 12.2.1-12.2.7 (Ausubel ed., 1996)). Affinity is measured by titrating purified protein against a fixed amount of labeled double-stranded oligonucleotide target. The target typically comprises the natural binding site sequence flanked by the 3 bp found in the natural sequence and additional, constant flanking sequences. The natural binding site is typically 9 bp for a three-finger protein and 2.times.9 bp+intervening bases for a six finger ZFP. The annealed oligonucleotide targets possess a 1 base 5' overhang that allows for efficient labeling of the target with T4 phage polynucleotide kinase. For the assay the target is added at a concentration of 1 nM or lower (the actual concentration is kept at least 10-fold lower than the expected dissociation constant), purified ZFPs are added at various concentrations, and the reaction is allowed to equilibrate for at least 45 min. In addition the reaction mixture also contains 10 mM Tris (pH 7.5), 100 mM KCl, 1 mM $MgCl_2$, 0.1 mM $ZnCl_2$, 5 mM DTT, 10% glycerol, 0.02% BSA.

The equilibrated reactions are loaded onto a 10% polyacrylamide gel, which has been pre-run for 45 min in Tris/glycine buffer, then bound and unbound labeled target is resolved by electrophoresis at 150V. Alternatively, 10-20% gradient Tris-HCl gels, containing a 4% polyacrylamide stacking gel, can be used. The dried gels are visualized by autoradiography or phosphorimaging and the apparent Kd is determined by calculating the protein concentration that yields half-maximal binding.

The assays can also include a determination of the active fraction in the protein preparations. Active fraction is determined by stoichiometric gel shifts in which protein is titrated against a high concentration of target DNA. Titrations are done at 100, 50, and 25% of target (usually at micromolar levels).

The technique of phage display provides a largely empirical means of generating zinc finger proteins with a desired target specificity (see e.g., Rebar, U.S. Pat. No. 5,789,538; Choo et al., WO 96/06166; Barbas et al., WO 95/19431 and WO 98/543111; Jamieson et al., supra). The method can be used in conjunction with, or as an alternative to rational design. The method involves the generation of diverse libraries of mutagenized zinc finger proteins, followed by the isolation of proteins with desired DNA-binding properties using affinity selection methods.

Regulatory Domains

In certain embodiments, the compositions and methods disclosed herein involve fusions between a DNA-binding domain specifically targeted to one or more regulatory regions of a PEDF gene and a functional (e.g., repression or activation) domain (or a polynucleotide encoding such a fusion). In this way, the repression or activation domain is brought into proximity with a sequence in the PEDF gene that is bound by the DNA-binding domain. The transcriptional regulatory function of the functional domain is then able to act on PEDF regulatory sequences.

Accordingly, zinc finger proteins are often expressed with an exogenous domain (or functional fragment thereof) as fusion proteins. Common domains for addition to the ZFP include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases) and their associated factors and modifiers. A preferred domain for fusing with a ZFP when the ZFP is to be used for repressing expression of a target gene is a KRAB repression domain from the human KOX-1 protein (Thiesen et al., New Biologist 2, 363-374 (1990); Margolin et al., Proc. Natl. Acad. Sci. USA 91, 4509-4513 (1994); Pengue et al., Nucl. Acids Res. 22:2908-2914 (1994); Witzgall et al., Proc. Natl. Acad. Sci. USA 91, 4514-4518 (1994). Preferred domains for achieving activation include the HSV VP 16 activation domain (see, e.g., Hagmann et al., J. Virol. 71, 5952-5962 (1997)) nuclear hormone receptors (see, e.g., Torchia et al., Curr. Opin. Cell. Biol. 10:373-383 (1998)); the p65 subunit of nuclear factor kappa B (Bitko & Barik, J. Virol. 72:5610-5618 (1998) and Doyle & Hunt, Neuroreport 8:2937-2942 (1997)); Liu et al., Cancer Gene Ther. 5:3-28 (1998)), or artificial chimeric functional domains such as VP64 (Seifpal et al., EMBO J. 11, 4961-4968 (1992)).

Fusion molecules are constructed by methods of cloning and biochemical conjugation that are well-known to those of skill in the art. Fusion molecules comprise a DNA-binding domain and a functional domain (e.g., a transcriptional activation or repression domain). Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion.

Fusions between a polypeptide component of a functional domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, Ill.) Catalogue. Methods and compositions for making fusions between a minor groove binder and a polypeptide have been described. Mapp et al. (2000) Proc. Natl. Acad. Sci. USA 97:3930-3935.

The fusion molecules disclosed herein comprise a DNA-binding domain that binds to a target site in a PEDF gene. In certain embodiments, the target site is present in an accessible region of cellular chromatin. Accessible regions can be determined as described, for example, in co-owned WO 01/83732. If the target site is not present in an accessible region of cellular chromatin, one or more accessible regions can be generated as described in International Application WO 01/83793. In additional embodiments, the DNA-binding domain of a fusion molecule is capable of binding to cellular chromatin regardless of whether its target site is in an accessible region or not. For example, such DNA-binding domains are capable of binding to linker DNA and/or nucleosomal DNA. Examples of this type of "pioneer" DNA binding domain are found in certain steroid receptor and in hepatocyte nuclear factor 3 (HNF3). Cordingley et al. (1987) Cell 48:261-270; Pina et al. (1990) Cell 60:719-731; and Cirillo et al. (1998) EMBO J. 17:244-254.

For such applications, the fusion molecule is typically formulated with a pharmaceutically acceptable carrier, as is known to those of skill in the art. See, for example, Remington's Pharmaceutical Sciences, 17th ed., 1985; and co-owned WO 00/42219.

The functional component/domain of a fusion molecule can be selected from any of a variety of different components capable of influencing transcription of a gene once the fusion molecule binds to a target sequence via its DNA binding domain. Hence, the functional component can include, but is not limited to, various transcription factor domains, such as activators, repressors, co-activators, co-repressors, and silencers.

An exemplary functional domain for fusing with a DNA-binding domain such as, for example, a ZFP, to be used for repressing expression of a gene is a KRAB repression domain from the human KOX-1 protein (see, e.g., Thiesen et al., New Biologist 2, 363-374 (1990); Margolin et al., Proc. Natl. Acad. Sci. USA 91, 4509-4513 (1994); Pengue et al., Nucl. Acids Res. 22:2908-2914 (1994); Witzgall et al., Proc. Natl.

Acad. Sci. USA 91, 4514-4518 (1994). Another suitable repression domain is methyl binding domain protein 2B (MBD-2B) (see, also Hendrich et al. (1999) Mamm Genome 10:906-912 for description of MBD proteins). Another useful repression domain is that associated with the v-ErbA protein. See, for example, Damm, et al. (1989) Nature 339:593-597; Evans (1989) Int. J. Cancer Suppl. 4:26-28; Pain et al. (1990) New Biol. 2:284-294; Sap et al. (1989) Nature 340:242-244; Zenke et al. (1988) Cell 52:107-119; and Zenke et al. (1990) Cell 61:1035-1049.

Suitable domains for achieving activation include the HSV VP16 activation domain (see, e.g., Hagmann et al., J. Virol. 71, 5952-5962 (1997)) nuclear hormone receptors (see, e.g., Torchia et al., Curr. Opin. Cell. Biol. 10:373-383 (1998)); the p65 subunit of nuclear factor kappa B (Bitko & Barik, J. Virol. 72:5610-5618 (1998) and Doyle & Hunt, Neuroreport 8:2937-2942 (1997)); Liu et al., Cancer Gene Ther. 5:3-28 (1998)), or artificial chimeric functional domains such as VP64 (Seifpal et al., EMBO J. 11, 4961-4968 (1992)).

Additional exemplary activation domains include, but are not limited to, VP16, VP64, p300, CBP, PCAF, SRC1 PvALF, AtHD2A and ERF-2. See, for example, Robyr et al. (2000) Mol. Endocrinol. 14:329-347; Collingwood et al. (1999) J. Mol. Endocrinol. 23:255-275; Leo et al. (2000) Gene 245:1-11; Manteuffel-Cymborowska (1999) Acta Biochim. Pol. 46:77-89; McKenna et al. (1999) J. Steroid Biochem. Mol. Biol. 69:3-12; Malik et al. (2000) Trends Biochem. Sci. 25:277-283; and Lemon et al. (1999) Curr. Opin. Genet. Dev. 9:499-504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) Gene 245:21-29; Okanami et al. (1996) Genes Cells 1:87-99; Goff et al. (1991) Genes Dev. 5:298-309; Cho et al. (1999) Plant Mol. Biol. 40:419-429; Ulmason et al. (1999) Proc. Natl. Acad. Sci. USA 96:5844-5849; Sprenger-Haussels et al. (2000) Plant J. 22:1-8; Gong et al. (1999) Plant Mol. Biol. 41:33-44; and Hobo et al. (1999) Proc. Natl. Acad. Sci. USA 96:15,348-15,353.

Additional exemplary repression domains include, but are not limited to, KRAB, SID, MBD2, MBD3, members of the DNMT family (e.g., DNMT1, DNMT3A, DNMT3B), Rb, and MeCP2. See, for example, Bird et al. (1999) Cell 99:451-454; Tyler et al. (1999) Cell 99:443-446; Knoepfler et al. (1999) Cell 99:447-450; and Robertson et al. (2000) Nature Genet. 25:338-342. Additional exemplary repression domains include, but are not limited to, ROM2 and AtHD2A. See, for example, Chem et al. (1996) Plant Cell 8:305-321; and Wu et al. (2000) Plant J. 22:19-27.

Additional functional domains are disclosed, for example, in co-owned WO 00/41566.

Expression Vectors

The nucleic acid encoding the ZFP of choice is typically cloned into intermediate vectors for transformation into prokaryotic or eukaryotic cells for replication and/or expression, e.g., for determination of Kd. Intermediate vectors are typically prokaryote vectors, e.g., plasmids, or shuttle vectors, or insect vectors, for storage or manipulation of the nucleic acid encoding ZFP or production of protein. The nucleic acid encoding a ZFP is also typically cloned into an expression vector, for administration to a plant cell, animal cell, preferably a mammalian cell or a human cell, fungal cell, bacterial cell, or protozoal cell.

To obtain expression of a cloned gene or nucleic acid, a ZFP is typically subcloned into an expression vector that contains a promoter to direct transcription. Suitable bacterial and eukaryotic promoters are well known in the art and described, e.g., in Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994). Bacterial expression systems for expressing the ZFP are available in, e.g., E. coli, Bacillus sp., and Salmonella (Palva et al., Gene 22:229-235 (1983)). Kits for such expression systems are commercially available. Eukaryotic expression systems for mammalian cells, yeast, and insect cells are well known in the art and are also commercially available.

The promoter used to direct expression of a ZFP nucleic acid depends on the particular application. For example, a strong constitutive promoter is typically used for expression and purification of ZFP.

In contrast, when a ZFP is administered in vivo for gene regulation, either a constitutive or an inducible or tissue-specific promoter is used, depending on the particular use of the ZFP. In addition, a preferred promoter for administration of a ZFP can be a weak promoter, such as HSV TK or a promoter having similar activity. The promoter typically can also include elements that are responsive to transactivation, e.g., hypoxia response elements, Gal4 response elements, lac repressor response element, and small molecule control systems such as tet-regulated systems and the RU-486 system (see, e.g., Gossen & Bujard, PNAS 89:5547 (1992); Oligino et al., Gene Ther. 5:491-496 (1998); Wang et al., Gene Ther. 4:432-441 (1997); Neering et al., Blood 88:1147-1155 (1996); and Rendahl et al., Nat. Biotechnol. 16:757-761 (1998)).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the ZFP, and signals required, e.g., for efficient polyadenylation of the transcript, transcriptional termination, ribosome binding sites, or translation termination. Additional elements of the cassette may include, e.g., enhancers, and exogenous spliced intronic signals.

The particular expression vector used to transport the genetic information into the cell is selected with regard to the intended use of the ZFP. Standard bacterial expression vectors include plasmids such as pBR322 based plasmids, pSKF, pET23D, and commercially available fusion expression systems such as GST and LacZ. A preferred fusion protein is the maltose binding protein, "MBP." Such fusion proteins are used for purification of the ZFP. Epitope tags can also be added to recombinant proteins to provide convenient methods of isolation, for monitoring expression, and for monitoring cellular and subcellular localization, e.g., c-myc or FLAG.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with a ZFP encoding sequence under the direction of the polyhedrin promoter or other strong baculovirus promoters.

The elements that are typically included in expression vectors also include a replicon that functions in E. coli, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., J. Biol. Chem. 264:17619-17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132:349-351 (1977); Clark-Curtiss & Curtiss, Methods in Enzymology 101:347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, naked DNA, plasmid vectors, viral vectors, both episomal and integrative, and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

Assays

Once a ZFP has been designed and prepared according to the procedures just set forth, an initial assessment of the activity of the designed ZFP is undertaken. ZFP proteins showing the ability to modulate the expression of a gene of interest can then be further assayed for more specific activities depending upon the particular application for which the ZFPs have been designed. Thus, for example, the ZFPs provided herein can be initially assayed for their ability to modulate VEGF expression. More specific assays of the ability of the ZFP to modulate angiogenesis and/or to treat ischemia are then typically undertaken. A description of these more specific assays are set forth herein and in U.S. Patent Publication 20030021776.

The activity of a particular ZFP can be assessed using a variety of in vitro and in vivo assays, by measuring, e.g., protein or mRNA levels, product levels, enzyme activity, tumor growth; transcriptional activation or repression of a reporter gene; second messenger levels (e.g., cGMP, cAMP, IP3, DAG, Ca2+); cytokine and hormone production levels; and neovascularization, using, e.g., immunoassays (e.g., ELISA and immunohistochemical assays with antibodies), hybridization assays (e.g., RNase protection, Northerns, in situ hybridization, oligonucleotide array studies), calorimetric assays, amplification assays, enzyme activity assays, tumor growth assays, phenotypic assays, and the like.

ZFPs are typically first tested for activity in vitro using cultured cells, e.g., 293 cells, CHO cells, VERO cells, BHK cells, HeLa cells, COS cells, and the like. Preferably, human cells are used. The ZFP is often first tested using a transient expression system with a reporter gene, and then regulation of the target endogenous gene is tested in cells and in animals, both in vivo and ex vivo. The ZFP can be recombinantly expressed in a cell, recombinantly expressed in cells transplanted into an animal, or recombinantly expressed in a transgenic animal, as well as administered as a protein to an animal or cell using delivery vehicles described below. The cells can be immobilized, be in solution, be injected into an animal, or be naturally occurring in a transgenic or non-transgenic animal.

Modulation of gene expression is tested using one of the in vitro or in vivo assays described herein. Samples or assays are treated with a ZFP and compared to untreated control samples, to examine the extent of modulation. As described above, for regulation of endogenous gene expression, the ZFP typically has a Kd of 200 nM or less, more preferably 100 nM or less, more preferably 50 nM, most preferably 25 nM or less.

The effects of the ZFPs can be measured by examining any of the parameters described above. Any suitable gene expression, phenotypic, or physiological change can be used to assess the influence of a ZFP. When the functional consequences are determined using intact cells or animals, one can also measure a variety of effects such as tumor growth, wound healing, neovascularization, hormone release, transcriptional changes to both known and uncharacterized genetic markers (e.g., Northern blots or oligonucleotide array studies), changes in cell metabolism such as cell growth or pH changes, and changes in intracellular second messengers such as cGMP.

The effects of the ZFPs can be measured by examining any of the parameters described above. Any suitable gene expression, phenotypic, or physiological change can be used to assess the influence of a ZFP. When the functional consequences are determined using intact cells or animals, one can also measure a variety of effects such as tumor growth, wound healing, neovascularization, hormone release, transcriptional changes to both known and uncharacterized genetic markers (e.g., Northern blots or oligonucleotide array studies), changes in cell metabolism such as cell growth or pH changes, and changes in intracellular second messengers such as cGMP.

Preferred assays for ZFP regulation of endogenous gene expression can be performed in vitro. In one preferred in vitro assay format, ZFP regulation of endogenous gene expression in cultured cells is measured by examining protein production using an ELISA assay. The test sample is compared to control cells treated with a vector lacking ZFP-encoding sequences or a vector encoding an unrelated ZFP that is targeted to another gene.

In another embodiment, ZFP regulation of endogenous gene expression is determined in vitro by measuring the level of target gene mRNA expression. The level of gene expression is measured using amplification, e.g., using PCR, LCR, or hybridization assays, e.g., Northern hybridization, dot blotting and RNase protection. The use of quantitative RT-PCR techniques (i.e., the so-called TaqMan assays) can also be utilized to quantitate the level of transcript. The level of protein or mRNA is detected using directly or indirectly labeled detection agents, e.g., fluorescently or radioactively labeled nucleic acids, radioactively or enzymatically labeled antibodies, and the like, as described herein. Such methods are also described in U.S. Pat. No. 5,210,015 to Gelfand, U.S. Pat. No. 5,538,848 to Livak, et al., and U.S. Pat. No. 5,863,736 to Haaland, as well as Heid, C. A., et al., Genome Research, 6:986-994 (1996); Gibson, U. E. M, et al., Genome Research 6:995-1001 (1996); Holland, P. M., et al., Proc. Natl. Acad. Sci. USA 88:7276-7280, (1991); and Livak, K. J., et al., PCR Methods and Applications 357-362 (1995), each of which is incorporated by reference in its entirety.

Alternatively, a reporter gene system can be devised using a VEGF gene promoter operably linked to a reporter gene such as luciferase, green fluorescent protein, CAT, or β-gal.

The reporter construct is typically co-transfected into a cultured cell. After treatment with the ZFP of choice, the amount of reporter gene transcription, translation, or activity is measured according to standard techniques known to those of skill in the art.

Another example of a preferred assay format useful for monitoring ZFP regulation of endogenous gene expression is performed in vivo. This assay is particularly useful for examining genes such as VEGF involved in tumor support via neovascularization. In this assay, cultured tumor cells expressing the ZFP of choice are injected subcutaneously into an immune compromised mouse such as an athymic mouse, an irradiated mouse, or a SCID mouse. After a suitable length of time, preferably 4-8 weeks, tumor growth is measured, e.g., by volume or by its two largest dimensions, and compared to the control. Tumors that have statistically significant reduction (using, e.g., Student's T test) are said to have inhibited growth. Alternatively, the extent of tumor neovascularization can also be measured. Immunoassays using endothelial cell specific antibodies are used to stain for vascularization of the tumor and the number of vessels in the tumor. Tumors that have a statistically significant reduction in the number of vessels (using, e.g., Student's T test) are said to have inhibited neovascularization.

Transgenic and non-transgenic animals are also used for examining regulation of VEGF gene expression in vivo. Transgenic animals typically express the ZFP of choice. Alternatively, animals that transiently express the ZFP of choice, or to which the ZFP has been administered in a delivery vehicle, can be used. Regulation of endogenous gene expression is tested using any one of the assays described herein.

Pharmaceutical Compositions

The ZFPs provided herein, and more typically the nucleic acids encoding them, can optionally be formulated with a pharmaceutically acceptable carrier as a pharmaceutical composition. The compositions may include or encode multiple ZFPs which bind to and regulate the expression of one or more genes.

A. Nucleic Acid Based Compositions

Methods of non-viral delivery of nucleic acids encoding the ZFPs provided herein include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™. Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids encoding engineered ZFP take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs can include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vector that are able to transduce or infect non-dividing cells and typically produce high viral titers. Selection of a retroviral gene transfer system can therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731-2739 (1992); Johann et al., J. Virol. 66:1635-1640 (1992); Sommerfelt et al., Virol. 176:58-59 (1990); Wilson et al., J. Virol. 63:2374-2378 (1989); Miller et al., J. Virol. 65:2220-2224 (1991); PCT/US94/05700).

In applications where transient expression of the ZFP is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

In particular, at least six viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent.

pLASN and MFG-S are examples are retroviral vectors that have been used in clinical trials (Dunbar et al., Blood 85:3048-305 (1995); Kohn et al., Nat. Med. 1:1017-102 (1995); Malech et al., PNAS 94:22 12133-12138 (1997)). PA317/pLASN was the first therapeutic vector used in a gene therapy trial. (Blaese et al., Science 270:475-480 (1995)). Transduction efficiencies of 50% or greater have been observed for MFG-S packaged vectors. (Ellem et al., Immunol Immunother. 44(1):10-20 (1997); Dranoff et al., Hum. Gene Ther. 1:111-2 (1997).

Recombinant adeno-associated virus vectors (rAAV) is another alternative gene delivery system based on the defective and nonpathogenic parvovirus adeno-associated type 2 virus. Vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., Lancet 351:9117 1702-3 (1998), Kearns et al., Gene Ther. 9:748-55 (1996)).

Additional adeno-associated virus vehicles include AAA serotypes 1, 2, 5, 6, 7, 8 and 9; as well as chimeric AAV serotypes, e.g., AAV 2/1 and AAV 2/5. Both single-stranded and double-stranded (e.g., self-complementary) AAV vectors can be used.

Replication-deficient recombinant adenoviral vectors (Ad) are predominantly used for colon cancer gene therapy, because they can be produced at high titer and they readily infect a number of different cell types. Most adenovirus vectors are engineered such that a transgene replaces the Ad E1a, E1b, and E3 genes; subsequently the replication defector vector is propagated in human 293 cells that supply deleted gene function in trans. Ad vectors can transduce multiply types of tissues in vivo, including nondividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman et al., Hum. Gene Ther. 7:1083-9 (1998)). Additional examples of the use of adenovirus vectors for gene transfer in clinical trials include Rosenecker et al., Infection 24:15-10 (1996); Sterman et al., Hum. Gene Ther. 9:7 1083-1089 (1998); Welsh et al., Hum. Gene Ther. 2:205-18 (1995); Alvarez et al., Hum. Gene Ther. 5:597-613 (1997); Topf et al., Gene Ther. 5:507-513 (1998); Sterman et al., Hum. Gene Ther. 7:1083-1089 (1998).

Packaging cells are used to form virus particles that are capable of infecting a host cell. Such cells include 293 cells, which package adenovirus, and .psi.2 cells or PA317 cells, which package retrovirus. Viral vectors used in gene therapy are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., PNAS 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In some instances, cells are isolated from the subject organism, transfected with a ZFP nucleic acid (gene or cDNA), and re-infused back into the subject organism (e.g., patient). Various cell types suitable for ex vivo transfection are well known to those of skill in the art (see, e.g., Freshney et al., Culture of Animal Cells, A Manual of Basic Technique (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+cells in vitro into clinically important immune cell types using cytokines such a GM-CSF, IFN-Y and TNF-a are known (see Inaba et al., J. Exp. Med. 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panb cells), GR-1 (granulocytes), and Iad (differentiated antigen presenting cells) (see Inaba et al., J. Exp. Med. 176:1693-1702 (1992)).

Vectors (e.g., retroviruses, adenoviruses, liposomes, etc.) containing therapeutic ZFP nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions, as described below (see, e.g., Remington's Pharmaceutical Sciences, 17th ed., 1989).

B. Protein Compositions

An important factor in the administration of polypeptide compounds, such as the present ZFPs, is ensuring that the polypeptide has the ability to traverse the plasma membrane of a cell, or the membrane of an intra-cellular compartment such as the nucleus. Cellular membranes are composed of lipid-protein bilayers that are freely permeable to small, non-ionic lipophilic compounds and are inherently impermeable to polar compounds, macromolecules, and therapeutic or diagnostic agents. However, proteins and other compounds such as liposomes have been described, which have the ability to translocate polypeptides such as ZFPs across a cell membrane.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, Current Opinion in Neurobiology 6:629-634 (1996)). Another subsequence, the h (hydrophobic) domain of signal peptides, was found to have similar cell membrane translocation characteristics (see, e.g., Lin et al., J. Biol. Chem. 270:14255-14258 (1995)).

Examples of peptide sequences which can be linked to a ZFP, for facilitating uptake of ZFP into cells, include, but are not limited to: an 11 animo acid peptide of the tat protein of HIV; a 20 residue peptide sequence which corresponds to amino acids 84-103 of the p16 protein (see Fahraeus et al., Current Biology 6:84 (1996)); the third helix of the 60-amino acid long homeodomain of Antennapedia (Derossi et al., J. Biol. Chem. 269:10444 (1994)); the h region of a signal peptide such as the Kaposi fibroblast growth factor (K-FGF) h region (Lin et al., supra); or the VP22 translocation domain from HSV (Elliot & O'Hare, Cell 88:223-233 (1997)). Other suitable chemical moieties that provide enhanced cellular uptake may also be chemically linked to ZFPs.

Toxin molecules also have the ability to transport polypeptides across cell membranes. Often, such molecules are composed of at least two parts (called "binary toxins"): a translocation or binding domain or polypeptide and a separate toxin domain or polypeptide. Typically, the translocation domain or polypeptide binds to a cellular receptor, and then the toxin is transported into the cell. Several bacterial toxins, including *Clostridium perfringens* iota toxin, diphtheria toxin (DT), *Pseudomonas* exotoxin A (PE), pertussis toxin (PT), *Bacillus anthracis* toxin, and pertussis adenylate cyclase (CYA), have been used in attempts to deliver peptides to the cell cytosol as internal or amino-terminal fusions (Arora et al., J. Biol. Chem., 268:3334-3341 (1993); Perelle et al., Infect. Immun., 61:5147-5156 (1993); Stenmark et al., J. Cell Biol. 113:1025-1032 (1991); Donnelly et al., PNAS 90:3530-3534 (1993); Carbonetti et al., Abstr. Annu. Meet. Am. Soc. Microbiol. 95:295 (1995); Sebo et al., Infect. Immun. 63:3851-3857 (1995); Klimpel et al., PNAS U.S.A. 89:10277-10281 (1992); and Novak et al., J. Biol. Chem. 267:17186-17193 1992)).

Such subsequences can be used to translocate ZFPs across a cell membrane. ZFPs can be conveniently fused to or derivatized with such sequences. Typically, the translocation sequence is provided as part of a fusion protein. Optionally, a linker can be used to link the ZFP and the translocation sequence. Any suitable linker can be used, e.g., a peptide linker.

The ZFP can also be introduced into an animal cell, preferably a mammalian cell, via a liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell, i.e., a ZFP. The liposome fuses with the plasma membrane, thereby releasing the drug into the cytosol. Alternatively, the liposome is phagocytosed or taken up by the cell in a transport vesicle. Once in the endosome or phagosome, the liposome either degrades or fuses with the membrane of the transport vesicle and releases its contents.

In current methods of drug delivery via liposomes, the liposome ultimately becomes permeable and releases the encapsulated compound (in this case, a ZFP) at the target tissue or cell. For systemic or tissue specific delivery, this can be accomplished, for example, in a passive manner wherein the liposome bilayer degrades over time through the action of various agents in the body. Alternatively, active drug release involves using an agent to induce a permeability change in the liposome vesicle. Liposome membranes can be constructed so that they become destabilized when the environment becomes acidic near the liposome membrane (see, e.g., PNAS 84:7851 (1987); Biochemistry 28:908 (1989)). When liposomes are endocytosed by a target cell, for example, they become destabilized and release their contents. This destabilization is termed fusogenesis. Dioleoylphosphatidylethanolamine (DOPE) is the basis of many "fusogenic" systems.

Such liposomes typically comprise a ZFP and a lipid component, e.g., a neutral and/or cationic lipid, optionally including a receptor-recognition molecule such as an antibody that binds to a predetermined cell surface receptor or ligand (e.g., an antigen). A variety of methods are available for preparing liposomes as described in, e.g., Szoka et al., Ann. Rev. Biophys. Bioeng. 9:467 (1980), U.S. Pat. Nos. 4,186,183, 4,217, 344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91.backslash.17424, Deamer & Bangham, Biochim. Biophys. Acta 443:629-634 (1976); Fraley, et al., PNAS 76:3348-3352 (1979); Hope et al., Biochim. Biophys. Acta 812:55-65 (1985); Mayer et al., Biochim. Biophys. Acta 858: 161-168 (1986); Williams et al., PNAS 85:242-246 (1988); Liposomes (Ostro (ed.), 1983, Chapter 1); Hope et al., Chem. Phys. Lip. 40:89 (1986); Gregoriadis, Liposome Technology (1984) and Lasic, Liposomes: from Physics to Applications (1993)). Suitable methods include, for example, sonication, extrusion, high pressure/homogenization, microfluidization, detergent dialysis, calcium-induced fusion of small liposome vesicles and ether-fusion methods, all of which are well known in the art.

In some instances, liposomes are targeted using targeting moieties that are specific to a particular cell type, tissue, and the like. Targeting of liposomes using a variety of targeting moieties (e.g., ligands, receptors, and monoclonal antibodies) has been previously described (see, e.g., U.S. Pat. Nos. 4,957, 773 and 4,603,044).

Standard methods for coupling targeting agents to liposomes can be used. These methods generally involve incorporation into liposomes lipid components, e.g., phosphatidylethanolamine, which can be activated for attachment of targeting agents, or derivatized lipophilic compounds, such as lipid derivatized bleomycin. Antibody targeted liposomes can be constructed using, for instance, liposomes which incorporate protein A (see Renneisen et al., J. Biol. Chem., 265: 16337-16342 (1990) and Leonetti et al., PNAS 87:2448-2451 (1990).

C. Dosage

For therapeutic applications of ZFPs, the dose administered to a patient should be sufficient to effect a beneficial therapeutic response in the patient over time. The dose will be determined by the efficacy and Kd of the particular ZFP employed, the nuclear volume of the target cell, and the condition of the patient, as well as the body weight or surface area of the patient to be treated. The size of the dose also will be determined by the existence, nature, and extent of any adverse side-effects that accompany the administration of a particular compound or vector in a particular patient.

In determining the effective amount of the ZFP(s) to be administered in the treatment or prophylaxis of disease, the physician evaluates circulating plasma levels of the ZFP(s) or nucleic acid(s) encoding the ZFP(s), potential ZFP toxicities, progression of the disease, and the production of anti-ZFP antibodies. Administration can be accomplished via single or divided doses.

Administration

ZFPs and/or the nucleic acids encoding the ZFPs can be administered directly to a patient for modulation of gene expression and for therapeutic or prophylactic applications such as those described herein.

In general, and in view of the discussion herein, phrases referring to introducing a ZFP into an animal or patient can mean that a ZFP or ZFP fusion protein is introduced and/or that a nucleic acid encoding a ZFP of ZFP fusion protein is introduced in a form that can be expressed in the animal.

Administration of therapeutically effective amounts is by any of the routes normally used for introducing ZFP into ultimate contact with the tissue to be treated. The ZFPs are administered in any suitable manner, preferably with pharmaceutically acceptable carriers. Multiple ZFP-containing compositions may be administered concurrently or separately by the same or different routes. Suitable methods of administering such compositions are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there are a wide variety of suitable formulations of pharmaceutical compositions (see, e.g., Remington's Pharmaceutical Sciences, 17th ed. 1985)).

The ZFPs, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of the disclosed methods, compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described. A variety of delivery options are available for the delivery of the pharmaceutical compositions provided herein so as to modulate angiogenesis and thus, for example, the treatment of ischemic conditions. Depending upon the particular application, the compositions can be targeted to specific areas or tissues of a subject. Other treatments, in contrast, involve administering the composition in a general manner without seeking to target delivery to specific regions, for example the eye. For example, adeno-associated viral vectors transduce retinal epithelial cells and photoreceptor cells with high efficiency. See, e.g., Martin et al. (2002) *Methods* 28(2):267-75; Hansen et al. (2003) *Invest Opthalmol V is Sci.* 44(2):772-80.

Applications

ZFPs that regulate expression of the genes disclosed herein, and nucleic acids encoding them, can be utilized in wide variety of applications. As detailed below, certain methods are performed such that modulation involves activation of one or more PEDF genes. The ZFPs provided herein and the nucleic acids encoding them such as in the pharmaceutical compositions described supra can be utilized to activate expression of PEDF genes such that the resulting PEDF proteins can act to inhibit angiogenesis, both in cell cultures (i.e., in vitro applications) and in vivo, for example in the eye. Such activation can inhibit harmful angiogenesis. Hence, certain methods for inhibiting angiogenesis involve introducing a ZFP into an animal, e.g., a mammal, e.g., a human. Binding of the ZFP bearing an activation domain to a PEDF gene can enhance natural processes of anti-angiogenesis. For example, ocular diseases caused by increased vascularization (age-related macular degeneration, diabetic retinopathy and retinopathy of prematurity) often exhibit PEDF down-regulation, along with up-regulation of angiogenic factors.

Accordingly, PEDF-ZFP activators as described herein can advantageously be used, either alone or in combination with other therapeutic agents (e.g. inhibitors of VEGF/P1GF, ZFP repressors of VEGF/P1GF gene) to treat ocular diseases, for example by viral vector delivery directly to the eye. Physiologically relevant levels of PEDF can be produced to prevent the formation of new blood vessels, thereby stopping disease progression. Because PEDF also has neurotropic activity, it is predicted to offer protection to photoreceptor cells as well.

PEDF-ZFPs as described herein can also be used to modulate angiogenesis, including tumor growth. Increased angiogenesis is required for tumor progression and metastasis. Thus, ZFPs which activate PEDF expression can be advantageously used to inhibit angiogenesis in tumors, for example by targeting expression of the ZFP to tumors using tissue-specific promoters and/or by delivering a PEDF ZFP that represses angiogeneis via a viral vector (e.g. adenovirus) that selectively replicates in tumor cells. Such methods may also make use of additional molecules that inhibit tumor growth, for example, antibodies that inhibit tumor growth and/or ZFPs that upregulate expression of gene products involved in tumor inhibition, including but not limited to, cytokines such as GM-CSF.

The compositions described herein can also be used to repress PEDF expression, and, as such, increase angiogenesis. A variety of assays for assessing angiogenesis are known. For example, the ability of the ZFPs and/or nucleic acids to promote angiogenesis can be evaluated, for example, in chick chorioallantoic membrane, as discussed by Leung et al. (1989) Science 246:1306-1309. Another option is to conduct assays with rat corneas, as discussed by Rastinejad et al. (1989) Cell 56:345-355. Other assays are disclosed in U.S. Pat. No. 5,840,693.

The ZFPs can also be used for non-therapeutic applications such as in screening methods to identify agents that activate or repress expression of a PEDF gene or to detect target nucleic acids containing the target sequences.

Activation of PEDF Expression for Anti-Angiogenic Therapies

Since pigment epithelium-derived factor (PEDF) is an anti-angiogenic factor, increased production of PEDF protein by one or more cells of an organism can be used to treat conditions characterized by an abnormally high degree of vasculature and/or to block tumor growth by reducing the vascular supply to the tumor. Previous approaches to this type of anti-angiogenic therapy have involved introduction of PEDF protein, or cDNA encoding PEDF, into one or more cells of the organism to be treated. See, for example, U.S. Pat. Nos. 5,840,686; 6,288,024; 6,319,687; 6,391,850; 6,451,763; 6,573,092; 6,670,333 and 6,797,691.

The methods for anti-angiogenic therapy disclosed herein involve regulation of the expression of the endogenous cellular gene encoding PEDF by introducing, into one or more cells of an organism, a fusion protein that binds to the PEDF gene and activates its transcription, or a polynucleotide encoding such a protein. In certain embodiments, such a protein comprises a DNA-binding domain and a functional domain (e.g., a transcriptional activation domain or a transcriptional repression domain). The DNA-binding domain can be an engineered zinc finger binding domain as described, for example, in co-owned U.S. Pat. Nos. 6,453,242; 6,534,261; 6,607,882; 6,785,613; 6,794,136 and 6,824,978. See also, for example, U.S. Pat. Nos. 5,5,789,538; 6,007,988; 6,013,453; 6,140,466; 6,242,568; 6,410,248; 6,479,626; 6,746,838 and 6,790,941.

The DNA-binding domain can bind to any sequence, in the transcribed or non-transcribed region of the PEDF gene, or to any other sequence, as long as transcription of the PEDF gene is regulated. Methods for selecting target sites for binding by zinc finger proteins are disclosed in co-owned U.S. Pat. No. 6,453,242. In certain embodiments, the target site is in an accessible region of cellular chromatin as described, for example, in co-owned U.S. Patent Application Publication No. 2002/0064802 A1.

For those embodiments in which the DNA-binding domain is an engineered zinc finger binding domain, the zinc finger domain is engineered to bind a specific target site in the PEDF gene. The binding domain contains a plurality of zinc fingers (e.g., 2, 3, 4, 5, 6 or more zinc fingers). In general, an individual zinc finger binds a subsite of 3-4 nucleotides. The subsites can be adjacent in a target site (and are in some cases overlapping); alternatively any two or more subsites can be separated by gaps of one, two three or more nucleotides. See, for example, US 2003/0119023 (Jun. 26, 2003).

Exemplary target sites in the human PEDF gene (Gen Bank Accession No. U29953) and mouse PEDF gene (Gen Bank Accession No. NT-039515) are shown in Table 1.

Exemplary zinc finger binding domains that bind to target sites in the human and mouse PEDF genes are shown in Table 2.

TABLE 1

ZFP Target Sites in Human and Mouse PEDF genes

| ZFP No. | Target site[1] | Species and Location[2] |
|---|---|---|
| 6961 | GGATGGtGGTGCAGCAGTG (SEQ ID NO:8) | Human -75 |
| 6981 | GGCGTAaTGGATGGTGGTG (SEQ ID NO:9) | Human -83 |
| 6078 | GTGGTGgGAGAGGAGGGTG (SEQ ID NO:10) | Mouse -209 |
| 6969 | GATGTGGTGGGAGAGGAG (SEQ ID NO:11) | Mouse -213 |
| 7923 | GGATGGtGGTGCAGCAGTG (SEQ ID NO:12) | Human -75 |
| 7929 | ATGGTGGTGCAGCAGTGG (SEQ ID NO:13) | Human -74 |

[1]Nucleotides in uppercase represent those present in subsites bound by individual zinc fingers; those in lowercase represent nucleotides not present in a subsite
[2]Negative numbers refer to the distance, in nucleotides, between the near edge of the target sequence and the major transcription initiation site

TABLE 2

Amino acid sequences of recognition regions of PEDF gene-targeted ZFPs

| ZFP No. | F1 | F2 | F3 | F4 | F5 | F6 |
|---|---|---|---|---|---|---|
| 6961 | RSDALSR (SEQ ID NO:14) | QSGDLTR (SEQ ID NO:15) | QSGDLTR (SEQ ID NO:15) | TSGHLSR (SEQ ID NO:16) | RSDHLSN (SEQ ID NO:17) | QSATRIT (SEQ ID NO:18) |
| 6981 | RSDALSR (SEQ ID NO:14) | RSDALSR (SEQ ID NO:14) | RSDVLSQ (SEQ ID NO:19) | RNDHRIA (SEQ ID NO:20) | QSGALAR (SEQ ID NO:21) | DRSHLAR (SEQ ID NO:22) |
| 6078 | RSDVLSA (SEQ ID NO:23) | RSHHRIN (SEQ ID NO:24) | RSDHLSQ (SEQ ID NO:25) | RKDTRTN (SEQ ID NO:26) | RSDSLSR (SEQ ID NO:27) | RKDARIT (SEQ ID NO:28) |
| 6969 | RSDNLSR (SEQ ID NO:29) | DNNARIN (SEQ ID NO:30) | QSGHLQR (SEQ ID NO:31) | RSDALAR (SEQ ID NO:32) | RSDALAR (SEQ ID NO:32) | TSANLSR (SEQ ID NO:33) |

TABLE 2-continued

Amino acid sequences of recognition regions of PEDF gene-targeted ZFPs

| ZFP No. | F1 | F2 | F3 | F4 | F5 | F6 |
|---|---|---|---|---|---|---|
| 7923 | RSDVLSK (SEQ ID NO:34) | QNATRIK (SEQ ID NO:35) | QSGDLTR (SEQ ID NO:15) | TSGHLSR (SEQ ID NO:16) | RSDHLST (SEQ ID NO:36) | QSGHLSR (SEQ ID NO:37) |
| 7929 | RSDHLSQ (SEQ ID NO:25) | TSANRTT (SEQ ID NO:38) | RSDNLSE (SEQ ID NO:39) | RSAALAR (SEQ ID NO:40) | RSDTLSN (SEQ ID NO:41) | RKDVRIT (SEQ ID NO:42) |

Note:
The seven-residue amino acid sequences represent residues −1 thorough +6, with respect to the start of the helical portion of the zinc finger The optional functional domain of such molecules can be a transcriptional activation domain such as, for example, the Herpes simplex virus VP16 activation domain, the synthetic VP64 activation domain (i.e., four tandem copies of the VP16 domain) and/or the p65 activation domain from the NF-κB regulatory factor. More than one functional domain can be present in a fusion protein and, in these cases, multiple copies of the same functional domain can be present (e.g., two copies of a p65 activation domain). Alternatively, a plurality of different functional domains, in single or multiple copies, can be present in a single fusion protein.

Additional domains, such as epitope tags (e.g., FLAG, hemagglutinin, myc) and nuclear localization signals can also be present in a fusion protein as disclosed herein.

Treatment of Neovascularization

In another aspect, the compositions that modulate expression of PEDF as described herein are used in the treatment of conditions characterized by neovascularization. A non-limiting example of a condition characterized by neovascularization is age-related macular degeneration (AMD). Additional conditions include diabetic retinopathy and rheumatoid arthritis.

In certain embodiments, treatment of conditions characterized by neovascularization involves administration of a composition as described herein that activates expression of a PEDF gene and administration of a second composition that represses expression of a VEGF gene. The compositions may be administered sequentially in any order or concurrently. In certain embodiments, both compositions comprise ZFPs. In other embodiments, both compositions comprise polynucleotides encoding ZFPs. In still further embodiments, one composition comprises a polynucleotide encoding a ZFP and the other comprises a ZFP in protein form. In embodiments in which the ZFPs are administered as polynucleotides, a single nucleotide (e.g., expression vector) can be used that encodes both ZFPs.

Zinc finger proteins the bind to target sites in one or more VEGF genes have been described, for example, in U.S. Patent Publication 20030021776, incorporated herein by reference in its entirety. These ZFPs may comprise 2, 3, 4, 5, 6 or even more fingers and may also comprise functional domains such as repression domains as described above. For example, in one embodiment, the engineered ZFP that may be used in combination with the compositions described herein comprises three zinc fingers and the amino acid sequence of the recognition region of each zinc finger is as a follows: F1: DRSNLTR (SEQ ID NO:83); F2: TSGHLSR (SEQ ID NO:16); F3: RSDHLSR (SEQ ID NO:84). This ZFP recognizes the target site GGGGGTGAC (SEQ ID NO:85).

As noted above, treatment of conditions characterized by neovascularization typically involves the use of ZFPs that activate PEDF expression and, optionally, the use of ZFPs that repress VEGF expression. Accordingly, the ZFPs preferably include suitable functional domains, namely an activation domain for the PEDF-targeted ZFP(s) and a repressor domain for the VEGF-targeted ZFP(s).

Treatment of Malignancies

In additional embodiments, the compositions described herein are useful in treating tumors, particularly malignant tumors. Thus, PEDF-ZFP activators can be administered to a subject having a malignancy in order to inhibit growth and/or metastasis of a malignant tumor.

The PEDF ZFP activator can be delivered via a viral delivery vehicle (e.g. adenovirus) that selectively replicates in tumor cells; or via a replication-defective viral vector that uses a tumor-specific promoter to control the expression of the ZFP. Examples of tumor-specific promoters include: E2F-1, Survivin, cyclooxygenase-2 (COX-2), epithelial glycoprotein 2 (EGP-2), and TERT (amongst others). Selective expression of the ZFP can also be achieved using tissue specific promoters such as those of the prostate, or hypoxia-dependent promoters, described above. Many malignancies can be advantageously treated using ZFPs that acts as PEDF activators. In addition, because PEDF differentiates neurons, this treatment may be particularly useful in tumors of neuronal origin, by both repressing angiogenesis and inducing differentiation that can potentially render the tumors less aggressive.

The PEDF ZFP activators described herein can be used alone. Alternatively, these ZFPs may be used in combination with other treatments that target different aspects of tumorigenesis (e.g., immune stimulation). One non-limiting example of such a combination therapy involves the use of a PEDF ZFP activator in combination with a ZFP transcription factor that activates the transcription of a cytokine, e.g., granulocyte macrophage colony stimulating factor (GM-CSF). GM-CSF inhibits tumor progression by stimulating the immune response to tumor specific antigens, while PEDF activation inhibits the angiogenesis that is required for tumor expansion. Together, ZFPs that activate PEDF and GM-CSF transcription have the potential to effectively kill existing tumor cells and prevent tumor progression. Moreover, both PEDF and GM-CSF are secreted and thus have the potential to exert "bystander" effects on cells in which the PEDF and/or GM-CSF genes are not activated.

Exemplary target sites in the human GM-CSF gene (Gen Bank Accession No. M13207) and mouse GM-CSF gene (Gen Bank Accession No. X03020) are shown in Table 3.

Exemplary zinc finger binding domains that bind to target sites in the human and mouse GM-CSF genes are shown in Table 4.

TABLE 3

ZFP Target Sites in Human and Mouse GM-CSF genes

| ZFP No. | Target site[1] | Species and Location[2] |
|---|---|---|
| Rac4a | GTGGCTGAT (SEQ ID NO:43) | Human −119 |
| Lcu6a | GCAGGGGTC (SEQ ID NO:44) | Human −557 |
| 5925 | GTGGCTGATn₄₂₉GCAGGGGTC (SEQ ID NO:45) | Human −119 and −557 |
| NN11.2 | GTGGCTGATAAGGGCCAG (SEQ ID NO:46) | Human −119 |
| 7606 | GTGGCTGATAAGGGCCAG (SEQ ID NO:46) | Human −119 |
| 7608 | GTGGCTGATAAGGGCCAG (SEQ ID NO:46) | Human −119 |
| 7779 | GATAATGAGGTGGACTTG (SEQ ID NO:47) | Mouse −502 |
| 7780 | GAGGTGGACTTGtGAGAAG (SEQ ID NO:48) | Mouse −496 |
| 7905 | GTGGCTGATAAGGGCCAG (SEQ ID NO:46) | Human −119 |
| 7906 | GTGGCTGATAAGGGCCAG (SEQ ID NO:46) | Human −119 |

[1]Nucleotides in uppercase represent those present in subsites bound by individual zinc fingers; those in lowercase represent nucleotides not present in a subsite
[2]Negative numbers refer to the distance, in nucleotides, between the 5'-most nucleotide in the target sequence and the major transcription initiation site

TABLE 4

Amino acid sequences of recognition regions of GM-CSF gene-targeted ZFPs*

| ZFP No. | F1 | F2 | F3 | F4 | F5 | F6 |
|---|---|---|---|---|---|---|
| Rac4a | QSGNLAR (SEQ ID NO:49) | QSSDLTR (SEQ ID NO:50) | RSDALTR (SEQ ID NO:51) | | | |
| Lcu6a | DRSALAR (SEQ ID NO:52) | RSDHLTR (SEQ ID NO:53) | QSGDLTR (SEQ ID NO:15) | | | |
| 5925[†] | DRSALAR (SEQ ID NO:52) | RSDHLTR (SEQ ID NO:53) | QSGDLTR (SEQ ID NO:15) | QSGNLAR (SEQ ID NO:49) | QSSDLTR (SEQ ID NO:50) | RSDALTR (SEQ ID NO:51) |
| NN11.2 | DRSNLTA (SEQ ID NO:54) | DRSHLSR (SEQ ID NO:55) | RSDNLTQ (SEQ ID NO:56) | TSGNLTR (SEQ ID NO:57) | QSSDLSR (SEQ ID NO:58) | RSDALAR (SEQ ID NO:32) |
| 7606 | RSDALSV (SEQ ID NO:59) | DSSHRTR (SEQ ID NO:60) | RSDHLSA (SEQ ID NO:61) | ANSNRIK (SEQ ID NO:62) | QSSDLSR (SEQ ID NO:58) | RSDALAR (SEQ ID NO:32) |
| 7608 | RSDNLSE (SEQ ID NO:39) | DRSHLAR (SEQ ID NO:22) | RSDHLSA (SEQ ID NO:61) | ANSNRIK (SEQ ID NO:62) | QSSDLSR (SEQ ID NO:58) | RSDALAR (SEQ ID NO:32) |
| 7779 | RSDVLSA (SEQ ID NO:23) | DRSNRIK (SEQ ID NO:63) | RSDALSR (SEQ ID NO:14) | RSDNLTR (SEQ ID NO:64) | DRSTLIE (SEQ ID NO:86) | SSSNLSR (SEQ ID NO:66) |
| 7780 | RSDNLSV (SEQ ID NO:67) | RSANLTR (SEQ ID NO:68) | RSDVLSA (SEQ ID NO:23) | DRSNRIK (SEQ ID NO:69) | RSDALSR (SEQ ID NO:14) | RSDNLTR (SEQ ID NO:64) |
| 7905 | RSDALSE (SEQ ID NO:65) | DSSHRTR (SEQ ID NO:60) | RSDHLSA (SEQ ID NO:61) | ANSNRIK (SEQ ID NO:62) | QSSDLSR (SEQ ID NO:58) | RSDALAR (SEQ ID NO:32) |
| 7906 | RSDNLSE (SEQ ID NO:39) | DSSHRTR (SEQ ID NO:60) | RSDHLSA (SEQ ID NO:61) | ANSNIRIK (SEQ ID NO:62) | QSSDLSR (SEQ ID NO:58) | RSDALAR (SEQ ID NO:32) |

*The seven-residue amino acid sequences represent residues −1 thorough +6, with respect to the start of the helical portion of the zinc finger
[†]The 5925 protein contains two three-finger zinc finger binding domains separated by a linker sequence of 22 amino acids The ZFPs which activate PEDF and/or GM-CSF may be used ex vivo, for example with isolated mesenchymal stem cells. When mesenchymal stem cells are returned to the body, they target to the sites of tumor growth and, accordingly, target the PEDF activating ZFPs to these sites. Studeny et al. (2004) *J Natl Cancer Inst.* 96(21):1593-603.

In other embodiments, the PEDF ZFP activators described herein are used in combination with other angiogenesis inhibitors. Non-limiting examples of such inhibitors include antibodies that bind to VEGF (e.g., bevacizumab, manufactured as Avastin™ by Genentech, Inc, South San Francisco, Calif. and/or anti-CTLA4 antibodies as described, for example, in Hanahan et al. (2003) *Cancer Res.* 63(11):3005-8.)

EXAMPLES

The following examples are presented as illustrative of, but not limiting, the claimed subject matter.

Example 1

Design of ZFPs that Bind to PEDF

Four six fingered ZFPs were designed to target human and mouse PEDF genes as shown in Table 1 above. In particular, ZFP Nos. 6961 and 6981 are targeted to the human PEDF promoter, while ZFP Nos. 6078 and 6969 are targeted to the mouse PEDF promoter. The target sequences for these ZFPs are shown in Table 1. ZFP Nos 6961, 6981, 6078 and 6969 are each six finger ZFPs that can be linked to either a transcriptional activation domain (e.g. the activation domain of VP16, the activation domain of NF-κB p65) or a transcriptional repression domain (e.g. the KRAB-AB box repression domain of the KOX1 protein), depending on whether activation or repression of PEDF is desired.

These ZFPs may also include a nuclear localization sequence (NLS), for example as described in Example 2 below.

The amino acid sequence for ZFP No. 6961 linked to 2 copies of the NF-κB p65 activation domain is shown below:

```
                                          (SEQ ID NO:70)
MAPKKKRKVGIHGVPAAMAERPFQCRICMRNFSRSDALSRHIIRT

HTGEKPFACDICGRKFAQSGDLTRHTKIHTGGQRPFQCRICMRNFSQSGD

LTRHIRTHTGEKPFACDICGRKFATSGHLSRHTKIHTGGGSQKPFQCRI

CMRNFSRSDHLSNHIRTHTGEKPFACDICGKKFAQSATRITHTKIHLRQK

DAARGSMEFQYLPDTDDRHRIEEKRKRTYETFKSIMKKSPFSGPTDPRPP

PRIAVPSRSSASVPKPAPQPYPFTSSLSTINYDEFPTMVFPSGQISQASA

LAPAPPQVLPQAPAPAPAPAMVSALAQAPAPVPVLAPGPPQAVAPPAPKP

TQAGEGTLSEALLQLQFDDEDLGALLGNSTDPAVFTDLASVDNSEFQQLL

NQGIPVAPHTTEPMLMEYPEAITRLVTGAQRPPDPAPAPLGAPGLPNGLL

SGDEDFSSIADMDFSALLSQISSRSMEFQYLPDTDDRHRIEEKRKRTYET

FKSIMKKSPFSGPTDPRPPPRRIAVPSRSSASVPKPAPQPYPFTSSLSTI

NYDEFPTMVFPSGQISQASALAPAPPQVLPQAPAPAPAMVSALAQAPA

PVPVLAPGPPQAVAPPAPKPTQAGEGTLSEALLQLQFDDEDLGALLGNST

DPAVFTDLASVDNSEFQQLLNQGIPVAPHTTEPMLMEYPEAITRLVTGAQ
```

```
                                          -continued
RPPDPAPAPLGAPGLPNGLLSGDEDFSSIADMDFSALLSQISSGSDYKDD

DDK
```

The amino acid sequence for 6078 linked to a single copy of the NF-κB p65 activation domain is:

```
                                          (SEQ ID NO:71)
MAPKKKRKVGIHGVPAAMAERPFQCRICMRNFSRSDVLSAHIRTHTGEKP

FACDICGKKFARSHHRINHTKIHTGGQRPFQCRICMRNFSRSDHLSQHIR

THTGEKPFACDICGRKFARKDTRTNHTKIHTGGVGSQKPFQCRICMRNFS

RSDSLSRHIRTHTGEKPFACDICGKKFARKDARITHTKIHLRQKDAARGS

GHRGMEFQYLPDTDDRHRIEEKRKRTYETFKSIMKKSPFSGPTDPRPPPR

RIAVPSRSSASVPKPAPQPYPFTSSLSTINYDEFPTMVFPSGQISQASAL

APAPPQVLPQAPAPAPAPAMVSALAQAPAPVPVLAPGPPQAVAPPAPKPT

QAGEGTLSEALLQLQFDDEDLGALLGNSTDPAVFTDLASVDNSEFQQLLN

QGIPVAPHTTEPMLMEYPEAITRLVTGAQRPPDPAPAPLGAPGLPNGLLS

GDEDFSSIADMDFSALLSQISSGSDYKDDDDK
```

Example 2

Construction of PEDF-Binding ZFPs

Polynucleotides encoding the ZFPs described in Example 1 and Table 1 were prepared and inserted into expression cassettes using standard molecular biological techniques.

Briefly, ZFPs were assembled from an archive of in-vitro-selected modules as described. Moore et al. (2001) *Proc. Natl. Acad. Sci. USA* 98:437-1441; Isalan and Choo (2001) *Methods Enzymol.* 340:593-609. Assembled ZFPs were cloned into pcDNA 3.1 (Invitrogen) as in-frame NH$_2$-terminal fusions to the functional domain (e.g. the activation domain of NF-κB p65).

Retroviral and adenoviral vectors are also prepared. Briefly, all ZFP constructs contained an N-terminal nuclear localization signal (Pro-Lys-Lys-Lys-Arg-Lys-Val) (SEQ ID NO:72) from SV40 largeT antigen, a Zinc Finger DNA-binding domain, an activation domain from amino acid 413 to 490, and a FLAG peptide (Asp-Tyr-Lys-Asp-Asp-Asp-Asp-Lys) (SEQ ID NO:73). Retroviral vectors are produced in the 293 AMPHO-PAK™ cell line. Virus-containing supernatant is collected 48 hr after transfection, filtered through 0.45-mm-pore-size filter and used fresh for transduction of target cells or aliquoted and stored at −80° C. Similarly, recombinant adenovirus vectors are prepared using the Ad-Easy system. T. C. He, et al. (1998) *Proc. Natl. Acad. Sci. U.S.A.* 95:2509-2514.

Example 3

Activation of PEDF

Cell culture and transfection: Mouse Neuro2a cells were cultured in DMEM with 10% FBS. Human HEK293 cells were cultured in DMEM supplemented with 10% FBS. Human ARPE-19 cells (denoted "RPE" infra) were cultured in DMEM/F12 (50-50 mix) supplemented with 10% FBS. Cells were seeded into 6-well plates at the density of ~1.5× 10$^5$ cells/well 16 to 24 hours prior to transfection. Duplicate transfections were performed for each construct using Lipofectamine™ 2000 (Invitrogen, Carlsbad, Calif.). 1 µg of the ZFP-TF expression plasmid or control plasmid were transfected into each well using 3 µl of Lipofectamine 2000 reagent. Transfection reagent-containing media was removed after 8 hours and fresh media was added. Cells were harvested 48 to 72 hours post-transfection for RNA isolation and Taqman analysis. Culture media were collected for analyzing secreted PEDF by Western blot.

Taqman Analysis: RNA was isolated using High Pure RNA Isolation Kit (Roche, Indianapolis, Ind.). Taqman assays were performed as previously described (J. Biol. Chem. 275 33850). In brief, TaqMan was performed in 96-well plate format on ABI 7700 SDS machine (Perkin Elmer, Boston, Mass.) and analyzed with SDS version 1.6.3 software. RNA samples (25 ng) were mixed with 0.1 µM of probe and optimal amount of each primer, 5.5 mM $MgCl_2$ and 0.3 mM (each) dNTP, 0.625 unit of AmpliTaq Gold DNA Polymerase, 6.25 units of MultiScribe Reverse Transcriptase, and 5 units of RNase Inhibitor in 1× TaqMan buffer A from PE. The reverse transcription reactions were performed at 48° C. for 30 minutes. After denaturing at 95° C. for 10 minutes, PCR amplification reactions were conducted for 40 cycles at 95° C. for 15 seconds and at 60° C. for 1 minute. The levels of PEDF (human or mouse) and 18S RNA were quantified using standard curves spanning a 125-fold concentration range (1 to 125 ng total RNA per reaction). Each RNA sample was assayed in duplicate Taqman reactions. The ratio of PEDF/18S was used to determine the relative levels of PEDF expression in various samples. Sequences and concentrations of primers and probes are provided in Table 5.

Western blot analysis: Culture media from Neuro2A, HEK293 and ARPE-19 cells that were transfected with ZFP-encoding plasmids or empty vectors were collected 48-72 hours post transfection. 30 µl of media and 10 µl LDS sample buffer (Invitrogen, Carlsbad, Calif.) were mixed, heated at 75° C. for 10 minutes and loaded onto 4-12% Bis-Tris NuPAGE gels (Invitrogen, Carlsbad, Calif.). After 1 hour of electrophoresis at 150v, proteins were transferred to nitrocellulose membrane for 2 hours at 30v, using an XCell transfer module (Invitrogen, Carlsbad, Calif.). Membranes were blocked with 4% dry milk in TBST (TBS with 0.1% Tween 20) for 1 hour at room temperature, then incubated with a polyclonal anti-PEDF antibody (Bioproducts MD, Middletown, Md., 1:1000 dilution) in 4% milk in TBST for 1 hour at room temperature; membranes were then washed 3 times (10 minutes each) in 4% dry milk in TBST, incubated with an HRP-conjugated anti-rabbit antibody (Pierce Biotechnology, Rockford, Ill., 1:2000 dilution) in 4% milk in TBST, washed 3 times (10 minutes each) in TBST, and incubated with Super-Signal West Femto reagent (Pierce Biotechnology, Rockford, Ill.) for 5 minutes and exposed to X-ray films.

Results

Figure 2:
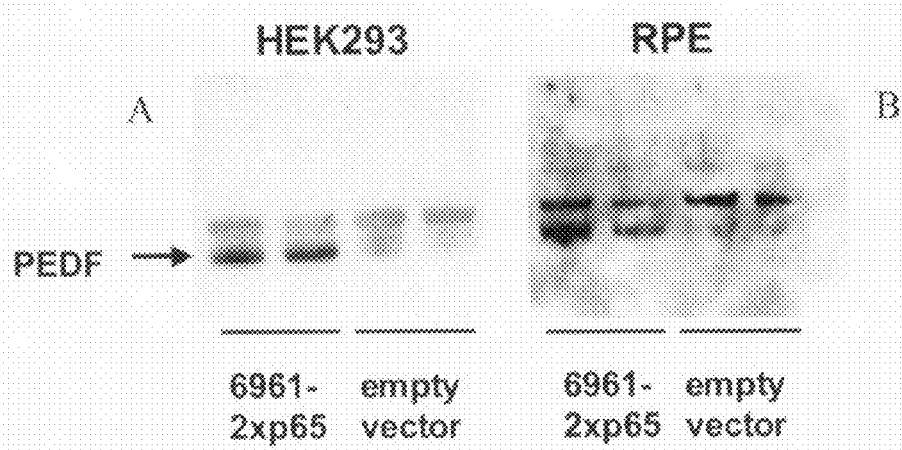
FIGS. 2A and 2B are reproductions of protein blots and depict levels of secreted PEDF in cells whose RNA analysis is shown in FIG. 1. ZFP No. 6961 increased levels of PEDF in HEK293 cells (FIG. 2A) and in RPE cells (FIG. 2B), as compared to controls.

Results, as shown in FIGS. 1, 2 and 3, demonstrate ZFPs as described herein activate PEDF transcription and increase PEDF secretion. FIGS. 1A and 1B show that expression of a p65/ZFP 6961 fusion protein in the human cell lines HEK293 (FIG. 1A) and RPE (FIG. 1B) resulted in increased PEDF RNA levels compared to control cells transfected with an empty vector. FIG. 3A shows increased PEDF levels in mouse Neuro2A cells transfected with an expression vector encoding a p65/ZFP 6078 fusion.

FIGS. 2A, 2B and 4 show protein blot analysis of PEDF secretion from human HEK293 cells transfected with a vector encoding a 2xp65/ZFP 6961 fusion (i.e., two copies of the p65 activation domain fused to the 6961 ZFP; FIG. 2A), human RPE cells transfected with a vector encoding a 2xp65/ZFP 6961 fusion (FIG. 2B) and mouse Neuro2A cells transfected with a vector encoding a p65/ZFP 6078 fusion (FIG. 4). The PEDF band is marked with an arrow.

Additional experiments showed that a p65/ZFP 6961 fusion activated PEDF transcription in the human tumor cell lines U87MG, SCC9 and HLAC.

Because hypoxia destabilizes the PEDF protein, transfection of cells cultured under hypoxic conditions with vectors encoding PEDF-targeted ZFP activators provides a stringent test of the ability of PEDF-targeted ZFPs to activate PEDF transcription and increase the production of PEDF protein. When such an experiment was conducted, expressing a p65/ZFP 6078 fusion in mouse Neuro2A cells, levels of secreted PEDF were observed to be similar in cells cultured under both normoxic and hypoxic conditions.

Example 4

Preparation of Adeno-Associated Virus (AAV) Vectors Encoding ZFPs Targeted to the PEDF Gene Sequences encoding either (1) the 6078 ZFP fused to a p65 transcriptional activation domain or (2) green fluorescent protein (GFP) were cloned into the AAV-TetO2-MCS vector, which was constructed by inserting 2 copies of the Tet opera-

TABLE 5

TAQMAN REAGENTS

| Gene Target | Oligonucleotide name | 5' --> 3' Sequence (SEQ ID NO) | uM/reaction |
|---|---|---|---|
| Human PEDF | hPEDF-753F | TTCCCGATGAGATCAGCATTC (74) | 0.3 |
| | hPEDF-819R | AACTTTGTTACCCACTGCCCC (75) | 0.9 |
| | hPEDF-775T** | CCTTCTCGGTGTGGCGCACTTCA (76) | 0.1 |
| mouse PEDF | mPEDF-1045F | GAATCACCCGACTTCAGCAAG (77) | 0.9 |
| | mPEDF-1119R | CTCGAAAGCAGCCCTGTGTT (78) | 0.9 |
| | mPEDF-1074T** | CAAACCCGTGAAGCTCACCCAAGTG (79) | 0.1 |
| 18S rRNA | 18s-For1 | TTCCGATAACGAACGAGACTCT (80) | 0.1 |
| | 18s-Rev1 | TGGCTGAACGCCACTTGTC (81) | 0.1 |
| | 18s-Pro1** | TAACTAGTTACGCGACCCCCGAG (82) | 0.1 |

Note:
Asterisks (**) denote probes. Probe ends are labeled with: 5' -- 6FAM; and 3' -- BHQ1 ("Black Hole Quencher 1" -- Biosearch).

tor sequence 3' to the CMV promoter of the AAV-MCS vector (Stratagene, La Jolla, Calif.). The HEK293-TRex cell line (Invitrogen, Carlsbad, Calif.) was used as the packaging cell line for AAV; it constitutively expresses the Tet repressor, which represses the expression of 6078-p65 during AAV production and improves virus titer. Cotransfection of the AAV constructs with helper plasmids (pRC and pHelper), AAV purification and virus genome quantification were performed using a method similar to that described in Gene Therapy 5:938-945.

Example 5

In Vivo Activation of PEDF Gene Expression in Mouse Eyes

Figure 5:
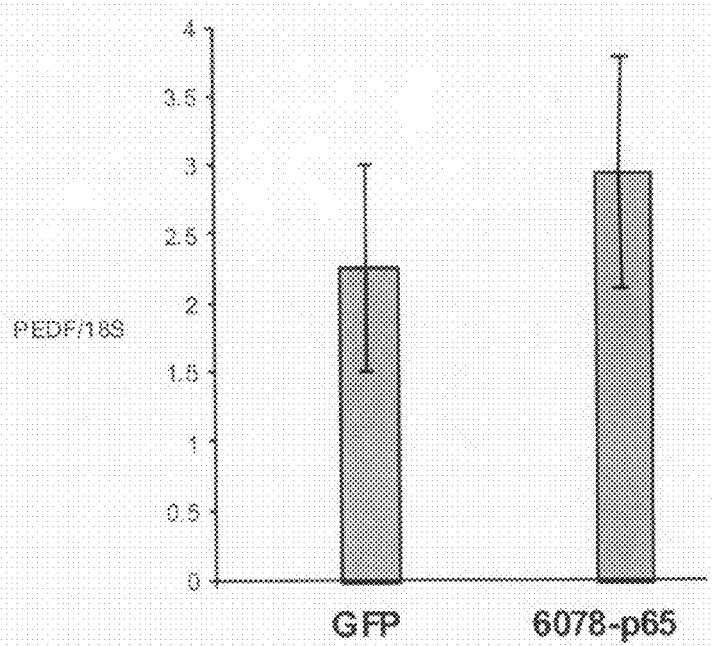
FIG. 5 shows levels of PEDF mRNA (normalized to 18S RNA levels) in mouse eyes that had been injected with AAV2 vectors encoding either GFP (left) or a PEDF-targeted ZFP (6078) fused to the p65 transcriptional activation domain (right).

AAV2-6078p65 and AAV2-GFP (as described in Example 4) were used in these experiments. Subretinal injection was performed with 1 ul of either the GFP or ZFP virus (~5×10$^8$ vector genomes). At 6 weeks post injection, RNA was isolated from posterior eye cups (3 eyes for AAV2-GFP injection and 5 eyes for AAV2-6078p65 injection) using Trizol reagent (Invitrogen, Carlsbad, Calif.). Taqman assays were performed as previously described (J. Biol. Chem. 275:33850). The levels of mouse PEDF and 18S RNA were quantified using standard curves spanning a 125-fold concentration range (1 to 125 ng total RNA per reaction). Each RNA sample was assayed in duplicate Taqman reactions. The ratios of PEDF/18S were used to determine the relative levels of PEDF expression. FIG. 5 shows a trend toward higher levels of PEDF mRNA in eyes injected with the 6078-p65 virus, compared to eyes injected with the control GFP-encoding virus.

Example 6

Reduction of Laser-Induced Choroidal Neovascularization in Mice

Figure 6:
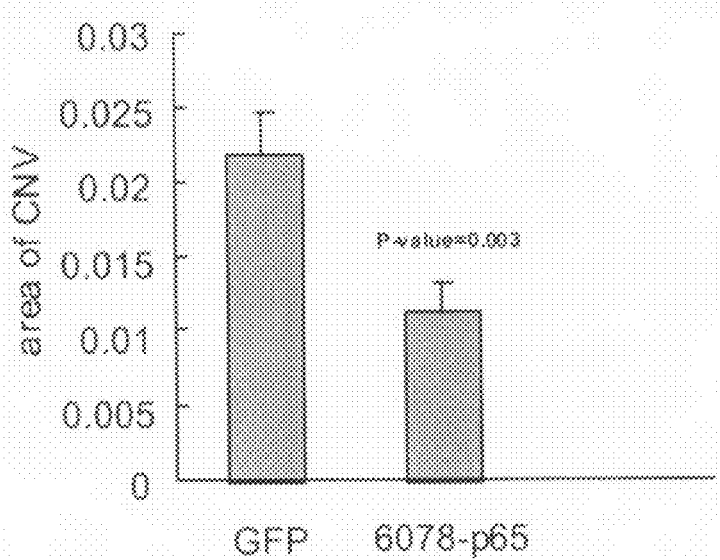
FIG. 6 shows areas of choroidal neovascularization in mouse eyes that had been injected with AAV2 vectors encoding either GFP (left) or a PEDF-targeted ZFP (6078) fused to the p65 transcriptional activation domain (right).

In a separate group of mice that also received subretinal injection of AAV2-GFP (5 eyes) and AAV2-6078p65 (5 eyes), Bruch's membrane was ruptured by laser irradiation at four locations per eye, at six weeks post-injection. This induces choroidal neovascularization (CNV), which closely mimics the neovascularization associated with age-related macular degeneration (AMD). Two weeks after the laser injury, mice were perfused with fluorescein-labeled dextran, and the sizes of CNV lesions (areas of hyperfluorescence) were measured in choroidal flat mounts. Visual observation of the mounts indicated that eyes that were injected with the PEDF activator virus contained smaller lesions than the eyes injected with control GFP virus, indicative of reduced CNV. The results were quantitated and shown to be statistically significant, as shown in FIG. 6.

Example 7

Dual PEDF activator/VEGF Repressor Constructs

Human- and mouse-specific vectors were constructed that encode two zinc finger fusion proteins: one a PEDF activator and the other a VEGF repressor. A 2A peptide sequence was placed between the sequences encoding the two zinc finger proteins. The general structure of the constructs was: NH$_2$-VEGF repressor-2A peptide sequence-PEDF activator-COOH. The identities of the VEGF repressors, PEDF activators and functional domains are given in Table 6.

TABLE 6

| | VEGF represser | | PEDF activator | |
|---|---|---|---|---|
| Construct | ZFP domain | Functional domain | ZFP domain | Functional domain |
| Mouse | 32E* | v-erbA | 6078[†] | single p65 |
| Human | 32E* | v-erbA | 6961[#] | tandem p65 |

*See US2003/0021776 (incorporated by reference) at Table 3 for the relevant recognition region amino acid sequences of the 32E protein, identified therein as VOP 32-E
[†]See Table 2 supra for recognition region sequences
[#]See Table 2 supra for recognition region sequences Both constructs were shown capable of activating PEDF expression in the appropriate (human or mouse) cell type.

Example 8

Coordinated Activation of PEDF and GM-CSF Genes in Human Cells using an Adenovirus Delivery Vehicle Sequences encoding a PEDF activator and a GM-CSF activator were inserted into a hybrid Adenovirus delivery vehicle. The virus was derived from Ad5, but contained Ad35 fiber. This virus was used to infect two human cell lines: the A2058 melanoma line and the SCC9 squamous cell carcinoma line.

The PEDF activator comprised the 6961 ZFP domain (Table 2 supra) and two tandem p65 activation domains. The GM-CSF activator comprised the 7905 ZFP domain (Table 4 supra) and a VP64 activation domain (i.e., four tandem VP16 activation domains).

This dual activator construct, delivered by infection with the Ad5/35 virus described above, was capable of activating transcription of both PEDF and GM-CSF genes in both A2058 and SCC9 cells.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

SEQUENCE LISTING

<160> NUMBER OF SEQ ID NOS: 86

<210> SEQ ID NO 1
<211> LENGTH: 25

```
<212> TYPE: PRT
<213> ORGANISM: Artificial Sequence
<220> FEATURE:
<223> OTHER INFORMATION: A motif characterizing the C2H2 class of
      proteins
<220> FEATURE:
<221> NAME/KEY: misc_feature
<222> LOCATION: (2)..(5)
<223> OTHER INFORMATION: Xaa can be any naturally occurring amino acid
      and up to 2 residues may be absent
<220> FEATURE:
<221> NAME/KEY: misc_feature
<222> LOCATION: (7)..(18)
<223> OTHER INFORMATION: Xaa can be any naturally occurring amino acid
<220> FEATURE:
<221> NAME/KEY: misc_feature
<222> LOCATION: (20)..(24)
<223> OTHER INFORMATION: Xaa can be any naturally occurring amino acid
      and up to 2 residues may be absent

<400> SEQUENCE: 1

Cys Xaa Xaa Xaa Xaa Cys Xaa Xaa Xaa Xaa Xaa Xaa Xaa Xaa Xaa
1               5                   10                  15

Xaa Xaa His Xaa Xaa Xaa Xaa Xaa His
            20                  25

<210> SEQ ID NO 2
<211> LENGTH: 5
<212> TYPE: PRT
<213> ORGANISM: Artificial Sequence
<220> FEATURE:
<223> OTHER INFORMATION: Peptide used to link zinc finger proteins

<400> SEQUENCE: 2

Thr Gly Glu Lys Pro
1               5

<210> SEQ ID NO 3
<211> LENGTH: 5
<212> TYPE: PRT
<213> ORGANISM: Artificial Sequence
<220> FEATURE:
<223> OTHER INFORMATION: Peptide used to link zinc finger proteins

<400> SEQUENCE: 3

Gly Gly Gly Gly Ser
1               5

<210> SEQ ID NO 4
<211> LENGTH: 8
<212> TYPE: PRT
<213> ORGANISM: Artificial Sequence
<220> FEATURE:
<223> OTHER INFORMATION: Peptide used to link zinc finger proteins

<400> SEQUENCE: 4

Gly Gly Arg Arg Gly Gly Gly Ser
1               5

<210> SEQ ID NO 5
<211> LENGTH: 9
<212> TYPE: PRT
<213> ORGANISM: Artificial Sequence
<220> FEATURE:
<223> OTHER INFORMATION: Peptide used to link zinc finger proteins

<400> SEQUENCE: 5

Leu Arg Gln Arg Asp Gly Glu Arg Pro
1               5
```

```
<210> SEQ ID NO 6
<211> LENGTH: 12
<212> TYPE: PRT
<213> ORGANISM: Artificial Sequence
<220> FEATURE:
<223> OTHER INFORMATION: Peptide used to link zinc finger proteins

<400> SEQUENCE: 6

Leu Arg Gln Lys Asp Gly Gly Gly Ser Glu Arg Pro
1               5                   10

<210> SEQ ID NO 7
<211> LENGTH: 16
<212> TYPE: PRT
<213> ORGANISM: Artificial Sequence
<220> FEATURE:
<223> OTHER INFORMATION: Peptide used to link zinc finger proteins

<400> SEQUENCE: 7

Leu Arg Gln Lys Asp Gly Gly Gly Ser Gly Gly Gly Ser Glu Arg Pro
1               5                   10                  15

<210> SEQ ID NO 8
<211> LENGTH: 19
<212> TYPE: DNA
<213> ORGANISM: Homo sapiens

<400> SEQUENCE: 8
ggatggtggt gcagcagtg                                              19

<210> SEQ ID NO 9
<211> LENGTH: 19
<212> TYPE: DNA
<213> ORGANISM: Homo sapiens

<400> SEQUENCE: 9
ggcgtaatgg atggtggtg                                              19

<210> SEQ ID NO 10
<211> LENGTH: 19
<212> TYPE: DNA
<213> ORGANISM: Mouse

<400> SEQUENCE: 10
gtggtgggag aggagggtg                                              19

<210> SEQ ID NO 11
<211> LENGTH: 18
<212> TYPE: DNA
<213> ORGANISM: Mouse

<400> SEQUENCE: 11
gatgtggtgg gagaggag                                               18

<210> SEQ ID NO 12
<211> LENGTH: 19
<212> TYPE: DNA
<213> ORGANISM: Homo sapiens

<400> SEQUENCE: 12
ggatggtggt gcagcagtg                                              19

<210> SEQ ID NO 13
```

```
<211> LENGTH: 18
<212> TYPE: DNA
<213> ORGANISM: Homo sapiens

<400> SEQUENCE: 13
atggtggtgc agcagtgg                                                    18

<210> SEQ ID NO 14
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene and the GM-CSF gene

<400> SEQUENCE: 14

Arg Ser Asp Ala Leu Ser Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene and the GM-CSF gene

<400> SEQUENCE: 15

Gln Ser Gly Asp Leu Thr Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene

<400> SEQUENCE: 16

Thr Ser Gly His Leu Ser Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene

<400> SEQUENCE: 17

Arg Ser Asp His Leu Ser Asn
1               5

<210> SEQ ID NO 18
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene

<400> SEQUENCE: 18

Gln Ser Ala Thr Arg Ile Thr
1               5
```

```
<210> SEQ ID NO 19
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene

<400> SEQUENCE: 19

Arg Ser Asp Val Leu Ser Gln
1               5

<210> SEQ ID NO 20
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene

<400> SEQUENCE: 20

Arg Asn Asp His Arg Ile Ala
1               5

<210> SEQ ID NO 21
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene

<400> SEQUENCE: 21

Gln Ser Gly Ala Leu Ala Arg
1               5

<210> SEQ ID NO 22
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene and the GM-CSF gene

<400> SEQUENCE: 22

Asp Arg Ser His Leu Ala Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene and the GM-CSF gene

<400> SEQUENCE: 23

Arg Ser Asp Val Leu Ser Ala
1               5

<210> SEQ ID NO 24
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene

<400> SEQUENCE: 24
```

-continued

Arg Ser His His Arg Ile Asn
1               5

<210> SEQ ID NO 25
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene

<400> SEQUENCE: 25

Arg Ser Asp His Leu Ser Gln
1               5

<210> SEQ ID NO 26
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene

<400> SEQUENCE: 26

Arg Lys Asp Thr Arg Thr Asn
1               5

<210> SEQ ID NO 27
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene

<400> SEQUENCE: 27

Arg Ser Asp Ser Leu Ser Arg
1               5

<210> SEQ ID NO 28
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene

<400> SEQUENCE: 28

Arg Lys Asp Ala Arg Ile Thr
1               5

<210> SEQ ID NO 29
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene

<400> SEQUENCE: 29

Arg Ser Asp Asn Leu Ser Arg
1               5

<210> SEQ ID NO 30
<211> LENGTH: 7
<212> TYPE: PRT
<213> ORGANISM: Artificial Sequence

```
<220> FEATURE:
<223> OTHER INFORMATION: Engineered zinc finger protein that binds to
      and regulates expression of the PEDF gene

<400> SEQUENCE: 30

Asp Asn Asn Ala Arg Ile Asn
1               5

<210> SEQ ID NO 31
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene

<400> SEQUENCE: 31

Gln Ser Gly His Leu Gln Arg
1               5

<210> SEQ ID NO 32
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene and the GM-CSF gene

<400> SEQUENCE: 32

Arg Ser Asp Ala Leu Ala Arg
1               5

<210> SEQ ID NO 33
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene

<400> SEQUENCE: 33

Thr Ser Ala Asn Leu Ser Arg
1               5

<210> SEQ ID NO 34
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene

<400> SEQUENCE: 34

Arg Ser Asp Val Leu Ser Lys
1               5

<210> SEQ ID NO 35
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene

<400> SEQUENCE: 35

Gln Asn Ala Thr Arg Ile Lys
1               5
```

```
<210> SEQ ID NO 36
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene

<400> SEQUENCE: 36

Arg Ser Asp His Leu Ser Thr
1               5

<210> SEQ ID NO 37
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene

<400> SEQUENCE: 37

Gln Ser Gly His Leu Ser Arg
1               5

<210> SEQ ID NO 38
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene

<400> SEQUENCE: 38

Thr Ser Ala Asn Arg Thr Thr
1               5

<210> SEQ ID NO 39
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene and the GM-CSF gene

<400> SEQUENCE: 39

Arg Ser Asp Asn Leu Ser Glu
1               5

<210> SEQ ID NO 40
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene

<400> SEQUENCE: 40

Arg Ser Ala Ala Leu Ala Arg
1               5

<210> SEQ ID NO 41
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene
```

```
<400> SEQUENCE: 41

Arg Ser Asp Thr Leu Ser Asn
1               5

<210> SEQ ID NO 42
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene

<400> SEQUENCE: 42

Arg Lys Asp Val Arg Ile Thr
1               5

<210> SEQ ID NO 43
<211> LENGTH: 9
<212> TYPE: DNA
<213> ORGANISM: Homo sapiens

<400> SEQUENCE: 43 gtggctgat                                                               9

<210> SEQ ID NO 44
<211> LENGTH: 9
<212> TYPE: DNA
<213> ORGANISM: Homo sapiens

<400> SEQUENCE: 44 gcagggtc                                                                9

<210> SEQ ID NO 45
<211> LENGTH: 19
<212> TYPE: DNA
<213> ORGANISM: Homo sapiens
<220> FEATURE:
<221> NAME/KEY: misc_feature
<222> LOCATION: (10)..(10)
<223> OTHER INFORMATION: n is a, c, g, or t

<400> SEQUENCE: 45
gtggctgatn gcagggtc                                                    19

<210> SEQ ID NO 46
<211> LENGTH: 18
<212> TYPE: DNA
<213> ORGANISM: Homo sapiens

<400> SEQUENCE: 46
gtggctgata agggccag                                                    18

<210> SEQ ID NO 47
<211> LENGTH: 18
<212> TYPE: DNA
<213> ORGANISM: Mouse

<400> SEQUENCE: 47
gataatgagg tggacttg                                                    18

<210> SEQ ID NO 48
<211> LENGTH: 19
<212> TYPE: DNA
<213> ORGANISM: Mouse
```

-continued

```
<400> SEQUENCE: 48
gaggtggact tgtgagaag                                                  19

<210> SEQ ID NO 49
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the GM-CSF gene

<400> SEQUENCE: 49

Gln Ser Gly Asn Leu Ala Arg
1               5

<210> SEQ ID NO 50
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the GM-CSF gene

<400> SEQUENCE: 50

Gln Ser Ser Asp Leu Thr Arg
1               5

<210> SEQ ID NO 51
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the GM-CSF gene

<400> SEQUENCE: 51

Arg Ser Asp Ala Leu Thr Arg
1               5

<210> SEQ ID NO 52
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the GM-CSF gene

<400> SEQUENCE: 52

Asp Arg Ser Ala Leu Ala Arg
1               5

<210> SEQ ID NO 53
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the GM-CSF gene

<400> SEQUENCE: 53

Arg Ser Asp His Leu Thr Arg
1               5

<210> SEQ ID NO 54
<211> LENGTH: 7
<212> TYPE: PRT
<213> ORGANISM: Artificial Sequence
```

```
<220> FEATURE:
<223> OTHER INFORMATION: Engineered zinc finger protein that binds to
      and regulates expression of the GM-CSF gene

<400> SEQUENCE: 54

Asp Arg Ser Asn Leu Thr Ala
1               5

<210> SEQ ID NO 55
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the GM-CSF gene

<400> SEQUENCE: 55

Asp Arg Ser His Leu Ser Arg
1               5

<210> SEQ ID NO 56
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the GM-CSF gene

<400> SEQUENCE: 56

Arg Ser Asp Asn Leu Thr Gln
1               5

<210> SEQ ID NO 57
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the GM-CSF gene

<400> SEQUENCE: 57

Thr Ser Gly Asn Leu Thr Arg
1               5

<210> SEQ ID NO 58
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene and the GM-CSF gene

<400> SEQUENCE: 58

Gln Ser Ser Asp Leu Ser Arg
1               5

<210> SEQ ID NO 59
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the GM-CSF gene

<400> SEQUENCE: 59

Arg Ser Asp Ala Leu Ser Val
1               5
```

<210> SEQ ID NO 60
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene and the GM-CSF gene

<400> SEQUENCE: 60

Asp Ser Ser His Arg Thr Arg
1               5

<210> SEQ ID NO 61
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene and the GM-CSF gene

<400> SEQUENCE: 61

Arg Ser Asp His Leu Ser Ala
1               5

<210> SEQ ID NO 62
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene and the GM-CSF gene

<400> SEQUENCE: 62

Ala Asn Ser Asn Arg Ile Lys
1               5

<210> SEQ ID NO 63
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the GM-CSF gene

<400> SEQUENCE: 63

Asp Arg Ser Asn Arg Ile Lys
1               5

<210> SEQ ID NO 64
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the GM-CSF gene

<400> SEQUENCE: 64

Arg Ser Asp Asn Leu Thr Arg
1               5

<210> SEQ ID NO 65
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene and the GM-CSF gene -continued

```
<400> SEQUENCE: 65

Arg Ser Asp Ala Leu Ser Glu
1               5

<210> SEQ ID NO 66
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene and the GM-CSF gene

<400> SEQUENCE: 66

Ser Ser Ser Asn Leu Ser Arg
1               5

<210> SEQ ID NO 67
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene and the GM-CSF gene

<400> SEQUENCE: 67

Arg Ser Asp Asn Leu Ser Val
1               5

<210> SEQ ID NO 68
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the GM-CSF gene

<400> SEQUENCE: 68

Arg Ser Ala Asn Leu Thr Arg
1               5

<210> SEQ ID NO 69
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the GM-CSF gene

<400> SEQUENCE: 69

Asp Arg Ser Asn Arg Ile Lys
1               5

<210> SEQ ID NO 70
<211> LENGTH: 748
<212> TYPE: PRT
<213> ORGANISM: Artificial Sequence
<220> FEATURE:
<223> OTHER INFORMATION: Zinc finger protein no. 6961 linked to 2 copies
      of the NF-kB p65 activation domain

<400> SEQUENCE: 70

Met Ala Pro Lys Lys Lys Arg Lys Val Gly Ile His Gly Val Pro Ala
1               5                   10                  15

Ala Met Ala Glu Arg Pro Phe Gln Cys Arg Ile Cys Met Arg Asn Phe
            20                  25                  30

Ser Arg Ser Asp Ala Leu Ser Arg His Ile Arg Thr His Thr Gly Glu
```

-continued

```
            35                  40                  45
Lys Pro Phe Ala Cys Asp Ile Cys Gly Arg Lys Phe Ala Gln Ser Gly
 50                  55                  60

Asp Leu Thr Arg His Thr Lys Ile His Thr Gly Gly Gln Arg Pro Phe
 65                  70                  75                  80

Gln Cys Arg Ile Cys Met Arg Asn Phe Ser Gln Ser Gly Asp Leu Thr
                 85                  90                  95

Arg His Ile Arg Thr His Thr Gly Glu Lys Pro Phe Ala Cys Asp Ile
             100                 105                 110

Cys Gly Arg Lys Phe Ala Thr Ser Gly His Leu Ser Arg His Thr Lys
             115                 120                 125

Ile His Thr Gly Gly Gly Ser Gln Lys Pro Phe Gln Cys Arg Ile
 130                 135                 140

Cys Met Arg Asn Phe Ser Arg Ser Asp His Leu Ser Asn His Ile Arg
145                 150                 155                 160

Thr His Thr Gly Glu Lys Pro Phe Ala Cys Asp Ile Cys Gly Lys Lys
                 165                 170                 175

Phe Ala Gln Ser Ala Thr Arg Ile Thr His Thr Lys Ile His Leu Arg
             180                 185                 190

Gln Lys Asp Ala Ala Arg Gly Ser Met Glu Phe Gln Tyr Leu Pro Asp
             195                 200                 205

Thr Asp Asp Arg His Arg Ile Glu Glu Lys Arg Lys Arg Thr Tyr Glu
 210                 215                 220

Thr Phe Lys Ser Ile Met Lys Lys Ser Pro Phe Ser Gly Pro Thr Asp
225                 230                 235                 240

Pro Arg Pro Pro Arg Arg Ile Ala Val Pro Ser Arg Ser Ser Ala
                 245                 250                 255

Ser Val Pro Lys Pro Ala Pro Gln Pro Tyr Pro Phe Thr Ser Ser Leu
                 260                 265                 270

Ser Thr Ile Asn Tyr Asp Glu Phe Pro Thr Met Val Phe Pro Ser Gly
             275                 280                 285

Gln Ile Ser Gln Ala Ser Ala Leu Ala Pro Ala Pro Pro Gln Val Leu
 290                 295                 300

Pro Gln Ala Pro Ala Pro Ala Pro Ala Pro Ala Met Val Ser Ala Leu
305                 310                 315                 320

Ala Gln Ala Pro Ala Pro Val Pro Val Leu Ala Pro Gly Pro Pro Gln
                 325                 330                 335

Ala Val Ala Pro Pro Ala Pro Lys Pro Thr Gln Ala Gly Glu Gly Thr
             340                 345                 350

Leu Ser Glu Ala Leu Leu Gln Leu Gln Phe Asp Asp Glu Asp Leu Gly
             355                 360                 365

Ala Leu Leu Gly Asn Ser Thr Asp Pro Ala Val Phe Thr Asp Leu Ala
 370                 375                 380

Ser Val Asp Asn Ser Glu Phe Gln Gln Leu Leu Asn Gln Gly Ile Pro
385                 390                 395                 400

Val Ala Pro His Thr Thr Glu Pro Met Leu Met Glu Tyr Pro Glu Ala
                 405                 410                 415

Ile Thr Arg Leu Val Thr Gly Ala Gln Arg Pro Pro Asp Pro Ala Pro
             420                 425                 430

Ala Pro Leu Gly Ala Pro Gly Leu Pro Asn Gly Leu Leu Ser Gly Asp
             435                 440                 445

Glu Asp Phe Ser Ser Ile Ala Asp Met Asp Phe Ser Ala Leu Leu Ser
 450                 455                 460
```

-continued

```
Gln Ile Ser Ser Arg Ser Met Glu Phe Gln Tyr Leu Pro Asp Thr Asp
465                 470                 475                 480

Asp Arg His Arg Ile Glu Lys Arg Lys Arg Thr Tyr Glu Thr Phe
            485                 490                 495

Lys Ser Ile Met Lys Lys Ser Pro Phe Ser Gly Pro Thr Asp Pro Arg
            500                 505                 510

Pro Pro Pro Arg Ile Ala Val Pro Ser Arg Ser Ser Ala Ser Val
            515                 520                 525

Pro Lys Pro Ala Pro Gln Pro Tyr Pro Phe Thr Ser Ser Leu Ser Thr
            530                 535                 540

Ile Asn Tyr Asp Glu Phe Pro Thr Met Val Phe Pro Ser Gly Gln Ile
545                 550                 555                 560

Ser Gln Ala Ser Ala Leu Ala Pro Ala Pro Pro Gln Val Leu Pro Gln
            565                 570                 575

Ala Pro Ala Pro Ala Pro Ala Pro Ala Met Val Ser Ala Leu Ala Gln
            580                 585                 590

Ala Pro Ala Pro Val Pro Val Leu Ala Pro Gly Pro Pro Gln Ala Val
            595                 600                 605

Ala Pro Pro Ala Pro Lys Pro Thr Gln Ala Gly Glu Gly Thr Leu Ser
            610                 615                 620

Glu Ala Leu Leu Gln Leu Gln Phe Asp Asp Glu Asp Leu Gly Ala Leu
625                 630                 635                 640

Leu Gly Asn Ser Thr Asp Pro Ala Val Phe Thr Asp Leu Ala Ser Val
            645                 650                 655

Asp Asn Ser Glu Phe Gln Gln Leu Leu Asn Gln Gly Ile Pro Val Ala
            660                 665                 670

Pro His Thr Thr Glu Pro Met Leu Met Glu Tyr Pro Glu Ala Ile Thr
            675                 680                 685

Arg Leu Val Thr Gly Ala Gln Arg Pro Pro Asp Pro Ala Pro Ala Pro
690                 695                 700

Leu Gly Ala Pro Gly Leu Pro Asn Gly Leu Leu Ser Gly Asp Glu Asp
705                 710                 715                 720

Phe Ser Ser Ile Ala Asp Met Asp Phe Ser Ala Leu Leu Ser Gln Ile
            725                 730                 735

Ser Ser Gly Ser Asp Tyr Lys Asp Asp Asp Lys
            740                 745

<210> SEQ ID NO 71
<211> LENGTH: 482
<212> TYPE: PRT
<213> ORGANISM: Artificial Sequence
<220> FEATURE:
<223> OTHER INFORMATION: Zinc finger protein no. 6078 linked to a single
      copy of the NF-kB p65 activation domain

<400> SEQUENCE: 71

Met Ala Pro Lys Lys Lys Arg Lys Val Gly Ile His Gly Val Pro Ala
1               5                   10                  15

Ala Met Ala Glu Arg Pro Phe Gln Cys Arg Ile Cys Met Arg Asn Phe
            20                  25                  30

Ser Arg Ser Asp Val Leu Ser Ala His Ile Arg Thr His Thr Gly Glu
            35                  40                  45

Lys Pro Phe Ala Cys Asp Ile Cys Gly Lys Lys Phe Ala Arg Ser His
            50                  55                  60

His Arg Ile Asn His Thr Lys Ile His Thr Gly Gly Gln Arg Pro Phe
```

```
            65                  70                  75                  80
Gln Cys Arg Ile Cys Met Arg Asn Phe Ser Arg Ser Asp His Leu Ser
                85                  90                  95
Gln His Ile Arg Thr His Thr Gly Glu Lys Pro Phe Ala Cys Asp Ile
                100                 105                 110
Cys Gly Arg Lys Phe Ala Arg Lys Asp Thr Arg Thr Asn His Thr Lys
                115                 120                 125
Ile His Thr Gly Gly Val Gly Ser Gln Lys Pro Phe Gln Cys Arg Ile
                130                 135                 140
Cys Met Arg Asn Phe Ser Arg Ser Asp Ser Leu Ser Arg His Ile Arg
145                 150                 155                 160
Thr His Thr Gly Glu Lys Pro Phe Ala Cys Asp Ile Cys Gly Lys Lys
                165                 170                 175
Phe Ala Arg Lys Asp Ala Arg Ile Thr His Thr Lys Ile His Leu Arg
                180                 185                 190
Gln Lys Asp Ala Ala Arg Gly Ser Gly His Arg Gly Met Glu Phe Gln
                195                 200                 205
Tyr Leu Pro Asp Thr Asp Asp Arg His Arg Ile Glu Glu Lys Arg Lys
                210                 215                 220
Arg Thr Tyr Glu Thr Phe Lys Ser Ile Met Lys Lys Ser Pro Phe Ser
225                 230                 235                 240
Gly Pro Thr Asp Pro Arg Pro Pro Arg Ile Ala Val Pro Ser
                245                 250                 255
Arg Ser Ser Ala Ser Val Pro Lys Pro Ala Pro Gln Pro Tyr Pro Phe
                260                 265                 270
Thr Ser Ser Leu Ser Thr Ile Asn Tyr Asp Glu Phe Pro Thr Met Val
                275                 280                 285
Phe Pro Ser Gly Gln Ile Ser Gln Ala Ser Ala Leu Ala Pro Ala Pro
                290                 295                 300
Pro Gln Val Leu Pro Gln Ala Pro Ala Pro Ala Pro Ala Pro Ala Met
305                 310                 315                 320
Val Ser Ala Leu Ala Gln Ala Pro Ala Pro Val Pro Val Leu Ala Pro
                325                 330                 335
Gly Pro Pro Gln Ala Val Ala Pro Pro Ala Pro Lys Pro Thr Gln Ala
                340                 345                 350
Gly Glu Gly Thr Leu Ser Glu Ala Leu Leu Gln Leu Gln Phe Asp Asp
                355                 360                 365
Glu Asp Leu Gly Ala Leu Leu Gly Asn Ser Thr Asp Pro Ala Val Phe
                370                 375                 380
Thr Asp Leu Ala Ser Val Asp Asn Ser Glu Phe Gln Gln Leu Leu Asn
385                 390                 395                 400
Gln Gly Ile Pro Val Ala Pro His Thr Thr Glu Pro Met Leu Met Glu
                405                 410                 415
Tyr Pro Glu Ala Ile Thr Arg Leu Val Thr Gly Ala Gln Arg Pro Pro
                420                 425                 430
Asp Pro Ala Pro Ala Pro Leu Gly Ala Pro Gly Leu Pro Asn Gly Leu
                435                 440                 445
Leu Ser Gly Asp Glu Asp Phe Ser Ser Ile Ala Asp Met Asp Phe Ser
                450                 455                 460
Ala Leu Leu Ser Gln Ile Ser Ser Gly Ser Asp Tyr Lys Asp Asp Asp
465                 470                 475                 480
Asp Lys
```

```
<210> SEQ ID NO 72
<211> LENGTH: 7
<212> TYPE: PRT
<213> ORGANISM: Artificial Sequence
<220> FEATURE:
<223> OTHER INFORMATION: N-terminal nuclear localization signal from
      SV40 large T antigen

<400> SEQUENCE: 72

Pro Lys Lys Lys Arg Lys Val
1               5

<210> SEQ ID NO 73
<211> LENGTH: 8
<212> TYPE: PRT
<213> ORGANISM: Artificial Sequence
<220> FEATURE:
<223> OTHER INFORMATION: FLAG peptide

<400> SEQUENCE: 73

Asp Tyr Lys Asp Asp Asp Asp Lys
1               5

<210> SEQ ID NO 74
<211> LENGTH: 21
<212> TYPE: DNA
<213> ORGANISM: Artificial Sequence
<220> FEATURE:
<223> OTHER INFORMATION: hPEDF-753F primer targeted to Human PEDF gene

<400> SEQUENCE: 74
ttcccgatga gatcagcatt c                                             21

<210> SEQ ID NO 75
<211> LENGTH: 21
<212> TYPE: DNA
<213> ORGANISM: Artificial Sequence
<220> FEATURE:
<223> OTHER INFORMATION: hPEDF-819R primer targeted to Human PEDF gene

<400> SEQUENCE: 75
aactttgtta cccactgccc c                                             21

<210> SEQ ID NO 76
<211> LENGTH: 23
<212> TYPE: DNA
<213> ORGANISM: Artificial Sequence
<220> FEATURE:
<223> OTHER INFORMATION: hPEDF-775T probe used in TAQMAN analysis of
      Human PEDF gene

<400> SEQUENCE: 76
ccttctcggt gtggcgcact tca                                           23

<210> SEQ ID NO 77
<211> LENGTH: 21
<212> TYPE: DNA
<213> ORGANISM: Artificial Sequence
<220> FEATURE:
<223> OTHER INFORMATION: mPEDF-1045F primer targeted to mouse PEDF gene

<400> SEQUENCE: 77
gaatcacccg acttcagcaa g                                             21

<210> SEQ ID NO 78
<211> LENGTH: 20
```

```
<212> TYPE: DNA
<213> ORGANISM: Artificial Sequence
<220> FEATURE:
<223> OTHER INFORMATION: mPEDF-1119R primer targeted to mouse PEDF gene

<400> SEQUENCE: 78
ctcgaaagca gccctgtgtt                                              20

<210> SEQ ID NO 79
<211> LENGTH: 25
<212> TYPE: DNA
<213> ORGANISM: Artificial Sequence
<220> FEATURE:
<223> OTHER INFORMATION: mPEDF-1074T probe used in TAQMAN analysis of
      mouse PEDF gene

<400> SEQUENCE: 79
caaacccgtg aagctcaccc aagtg                                        25

<210> SEQ ID NO 80
<211> LENGTH: 22
<212> TYPE: DNA
<213> ORGANISM: Artificial Sequence
<220> FEATURE:
<223> OTHER INFORMATION: 18s-For1 primer targeted to 18S tRNA

<400> SEQUENCE: 80
ttccgataac gaacgagact ct                                           22

<210> SEQ ID NO 81
<211> LENGTH: 19
<212> TYPE: DNA
<213> ORGANISM: Artificial Sequence
<220> FEATURE:
<223> OTHER INFORMATION: 18s-Rev1 primer targeted to 18S tRNA

<400> SEQUENCE: 81
tggctgaacg ccacttgtc                                               19

<210> SEQ ID NO 82
<211> LENGTH: 23
<212> TYPE: DNA
<213> ORGANISM: Artificial Sequence
<220> FEATURE:
<223> OTHER INFORMATION: 18s-Pro1 probe used in TAQMAN analysis of 18S
      tRNA

<400> SEQUENCE: 82
taactagtta cgcgaccccc gag                                          23

<210> SEQ ID NO 83
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the PEDF gene

<400> SEQUENCE: 83

Asp Arg Ser Asn Leu Thr Arg
1               5

<210> SEQ ID NO 84
<211> LENGTH: 7
<212> TYPE: PRT
<213> ORGANISM: Artificial Sequence
<220> FEATURE:
```

```
<223> OTHER INFORMATION: Engineered zinc finger protein that binds to
      and regulates expression of the PEDF gene

<400> SEQUENCE: 84

Arg Ser Asp His Leu Ser Arg
1               5

<210> SEQ ID NO 85
<211> LENGTH: 9
<212> TYPE: DNA
<213> ORGANISM: Unknown
<220> FEATURE:
<223> OTHER INFORMATION: VEGF gene target site recognized by a zinc
      finger protein

<400> SEQUENCE: 85 gggggtgac                                                                9

<210> SEQ ID NO 86
<211> LENGTH: 7
<212> TYPE: PRT
<213> ORGANISM: Artificial Sequence
<220> FEATURE:
<223> OTHER INFORMATION: Engineered zinc finger protein that binds to
      and regulates expression of the GM-CSF gene

<400> SEQUENCE: 86

Asp Arg Ser Thr Leu Ile Glu
1               5
```

What is claimed is:

1. A method for the treatment of ocular neovascularization in a human or a mouse animal, the method comprising intraocularly introducing a fusion protein comprising a zinc finger protein and an activation domain into the human or mouse animal having a genome, the genome comprising a target site within a pigment epithelium derived factor (PEDF) gene, whereby the zinc finger protein binds to the target site and thereby modulates PEDF expression in the human or mouse animal such that ocular neovascularization is treated, and further wherein the zinc finger protein binds to a target site specified in Table 1 (SEQ ID NOs:8-13).

2. The method of claim 1, wherein the animal is a human and the zinc finger protein comprises six zinc fingers and the amino acid sequence of the recognition region of each of the zinc fingers is as follows:

| F1: | RSDALSR | (SEQ ID NO:14) |
| F2: | QSGDLTR | (SEQ ID NO:15) |
| F3: | QSGDLTR | (SEQ ID NO:15) |
| F4: | TSGHLSR | (SEQ ID NO:16) |
| F5: | RSDHLSN | (SEQ ID NO:17) |
| F6: | QSATRIT | (SEQ ID NO:18). |

3. The method of claim 1, wherein the activation domain is selected from the group consisting of the VP16 activation domain, the VP64 activation domain and the p65 activation domain.

4. The method of claim 3, wherein the protein comprises two p65 activation domains.

5. The method of claim 1, wherein the method further comprises inhibiting the expression of an endogenous gene encoding an angiogenic factor in one or more cells of the human or mouse animal.

6. The method of claim 5, wherein the angiogenic factor is a vascular endothelial growth factor (VEGF).

7. The method of claim 6, wherein the VEGF is vascular endothelial growth factor A (VEGF-A).

8. The method of claim 7, wherein expression of the endogenous VEGF-A gene is inhibited by binding of a zinc finger protein to a target site in the endogenous VEGF-A gene, wherein the zinc finger protein further comprises a repression domain.

9. The method of claim 8, wherein the animal is a human and the VEGF-A binding zinc finger protein comprises three zinc fingers and the amino acid sequence of the recognition region of each of the zinc fingers is as follows:

| F1: | DRSNLTR | (SEQ ID NO:83) |
| F2: | TSGHLSR | (SEQ ID NO:16) |
| F3: | RSDHLSR | (SEQ ID NO:84). |

10. The method of claim 9, wherein the repression domain is selected from the group consisting of the v-erbA repression domain and the KOX repression domain.

11. The method of claim 1, wherein the ocular neovascularization occurs in a disease selected from the group consisting of age-related macular degeneration (AMD), diabetic retinopathy (DR) and retinopathy of prematurity.

12. The method of claim 1, wherein the fusion protein is introduced intra-ocularly as a polynucleotide expression vector into one or more cells of the human or mouse animal.

13. The method of claim 9, wherein the fusion protein and the VEGF-binding zinc finger proteins are introduced intra-ocularly as a polynucleotide expression vector into one or more cells of the human.

14. The method of claim 12, in which the polynucleotide is introduced into one or more retinal epithelial cells.

15. The method of claim 12, in which the polynucleotide is encapsidated in a viral vector selected from the group consisting of adeno-associated virus (AAV), Adenovirus and lentivirus.

16. The method of claim 15, in which the viral vector is an adeno-associated virus (AAV).

17. The method of claim 16, in which the viral vector is AAV Type 2 or AAV Type 4.

\* \* \* \* \*